(12) United States Patent
West et al.

(10) Patent No.: US 7,445,772 B2
(45) Date of Patent: Nov. 4, 2008

(54) HETERODIMERIC FOUR HELIX BUNDLE CYTOKINES

(75) Inventors: James W. West, Seattle, WA (US); Stacey Tannheimer, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 11/675,890

(22) Filed: Feb. 16, 2007

(65) Prior Publication Data

US 2007/0167367 A1 Jul. 19, 2007

Related U.S. Application Data

(62) Division of application No. 11/486,758, filed on Jul. 14, 2006, now Pat. No. 7,196,172.

(60) Provisional application No. 60/700,550, filed on Jul. 19, 2005, provisional application No. 60/699,938, filed on Jul. 15, 2005.

(51) Int. Cl.
*A61K 38/19* (2006.01)
(52) U.S. Cl. .................. 424/85.1; 514/12; 514/885
(58) Field of Classification Search ............. None
See application file for complete search history.

(56) References Cited

U.S. PATENT DOCUMENTS

| 6,531,576 | B1 | 3/2003 | Piddington et al. ......... 530/350 |
| 2004/0059095 | A1 | 3/2004 | Piddington et al. | |

OTHER PUBLICATIONS

Incyte Pharmaceuticals, Inc. EST, INC1209538, 1996.
Incyte Pharmaceuticals, Inc. EST, INC1209224, 1996.
Genbank Acc. No. AA501097, EST1145727, 1997.
Incyte Pharmaceuticals, Inc. Library, BRAITUT24, date unknown.
Incyte Pharmaceuticals, Inc. EST, INC3347129, 1997.
Genbank Acc. No. AI045195, EST1784567, 1998.
Incyte Pharmaceuticals, Inc. Library, TESTNOT11, date unknown.
Incyte Pharmaceuticals, Inc. EST, INC4922572, 1998.
Incyte Pharmaceuticals, Inc. EST, INC4883838H2, 1998.
Incyte Pharmaceuticals, Inc. Library, LUNLTMT01, date unknown.
Incyte Pharmaceuticals, Inc. EST, INC4883096, 1998.
Genbank Acc. No. AW482402, EST3893275, 2000.
Incyte Pharmaceuticals, Inc. EST, INC7081907, 2000.
Bowie et al., "Deciphering the message in protein sequences: tolerance to amino acid substitutions," *Science* 247(4948):1306-1310, 1990.
Ngo et al., "In The Protein Folding Problem and Tertiary Structure Prediction," Merz and Le Grand (eds), Springer Verlag, pp. 433 and 492-1495, 1994.

*Primary Examiner*—Prema Mertz
(74) *Attorney, Agent, or Firm*—Deborah A. Sawislak

(57) ABSTRACT

Heterodimeric proteins comprising two helical bundle cytokines are disclosed. One of the polypeptides comprises zsig81 and a second polypeptide which comprises either p19 (aka IL-12A) or p35 (aka IL-12A). The proteins may be produced as fusion proteins or expressed as a single chain. The heterodimeric protein comprising zsig81 and p19 is designated zcyto33f2 and the heterodimeric protein comprising zsig81 and p35 is designated zcyto35f2. Zcyto33f2 and zcyto35f2 proteins are associated with epithelial cell types, including lung and gut epithelium, and may play a role in physiological conditions such as inflammation.

2 Claims, No Drawings

SEQUENCE LISTING

```
<160> NUMBER OF SEQ ID NOS: 70

<210> SEQ ID NO 1
<211> LENGTH: 1600
<212> TYPE: DNA
<213> ORGANISM: Homo sapiens
<220> FEATURE:
<221> NAME/KEY: CDS
<222> LOCATION: (134)...(655)
<220> FEATURE:
<221> NAME/KEY: sig_peptide
<222> LOCATION: (134)...(184)

<400> SEQUENCE: 1
gaattcggct cgaggcaaaa ggaagggagg gaagcactcc atcatctcac tggaagaac      60 ggcacgggca tacctgcagc tactgggggtt ccactgggct tgagggtcga tttttcacct    120
tttgaaggac aag atg cat tgg aag atg ttg ctg ctt ctg ctg ttg tat        169
            Met His Trp Lys Met Leu Leu Leu Leu Leu Tyr
                -15             -10 tac aat gct gag gct tct atg tgc cac agg tgg agc agg gct gtg ctc       217
Tyr Asn Ala Glu Ala Ser Met Cys His Arg Trp Ser Arg Ala Val Leu
 -5              1               5                   10 ttc cct gcc gcc cac cgg cca aag agg tcc tca tca ctg cca ttg aac       265
Phe Pro Ala Ala His Arg Pro Lys Arg Ser Ser Ser Leu Pro Leu Asn
                15                  20                  25 cca gtc ctg cag acc tcc ctg gag gag gtg gag ctg ctc tac gag ttc       313
Pro Val Leu Gln Thr Ser Leu Glu Glu Val Glu Leu Leu Tyr Glu Phe
            30                  35                  40 ctg ctg gcc gaa ctt gag atc agc cct gac ctg cag atc tcc atc aag       361
Leu Leu Ala Glu Leu Glu Ile Ser Pro Asp Leu Gln Ile Ser Ile Lys
        45                  50                  55 gac gag gag ctg gcc tcc ttg cgg aag gcc tca gac ttc cgc acc gtc       409
Asp Glu Glu Leu Ala Ser Leu Arg Lys Ala Ser Asp Phe Arg Thr Val
 60                  65                  70                  75 tgc aac aac gtc atc ccc aag agc atc cca gac atc cgc cgg ctc agc       457
Cys Asn Asn Val Ile Pro Lys Ser Ile Pro Asp Ile Arg Arg Leu Ser
```

```
                   80              85              90
gcc agc ctc tcc agc cac cct ggc atc ctc aag aaa gaa gac ttt gaa         505
Ala Ser Leu Ser Ser His Pro Gly Ile Leu Lys Lys Glu Asp Phe Glu
            95              100             105 agg aca gtg ctg acc ctg gcc tac aca gcc tac cgc aca gcc ctg tcc         553
Arg Thr Val Leu Thr Leu Ala Tyr Thr Ala Tyr Arg Thr Ala Leu Ser
        110             115             120 cac ggc cat cag aag gac atc tgg gcg cag tcc ctc gtt agc ctc ttc         601
His Gly His Gln Lys Asp Ile Trp Ala Gln Ser Leu Val Ser Leu Phe
    125             130             135 cag gcc ctg agg cac gac ttg atg cgc tcc tca cag ccg gga gta cct         649
Gln Ala Leu Arg His Asp Leu Met Arg Ser Ser Gln Pro Gly Val Pro
140             145             150             155 ccc tga gagactggcc cacaccagga cctcagagca gggaccagca cagtaatcca         705
Pro * gaaagtcttc attctctact ccatttacag agaccagcaa caaaacactt accgctgaca      765
cagagcagca gagatcaaac agtaacccg atgctctttt ctccttgtag tttcctggaa       825
gacacatctg attcatgcca tcatgtgacc tgggctggaa gaaagggctg aatggtcat       885 tcaagacgcc tccatgggca gaatggtttg cctatggcag gcagaattct gatatgcttc      945 aacccgagc agtggccaca cactcaagag tgagaacagg cgtgagccac cgtgcctggc      1005
ccaggatcta aaactttct aagtttcctc catcgttggc atcctcacag ctatctccaa      1065
tgtcactcaa gagacatcaa cagacattta actgctgcag acttcattgc tctgtcacct    1125
caccttgaat ctaacaaatc aaagtatttc tgcaggtcca atggtctaaa atcaaatgct    1185
tgttaaatga cttttacaa caccccttac tttcctaatc catttcaatc ttattttttt    1245
tattgtggta aaaacacat cacgtaaaat gtaccatctt aaccatttt aagcatatgg    1305 tacagcagtg ttaactccat gcatgttgtg aaacagaccc ccggaacttt ctcatcttgt    1365
aattctgaag ttctataccc accgaacaac tcctctttc ccttccccc tgcctgcccc    1425 agctcttggc accattattc tgctttctgt ttttgagagt ctgactactt aagatacctc    1485
atacaagcgg gatctggctt acatttcttg agcattgtat tctggaaaag tgtttccttc    1545
ctctgaaaaa tgggtagagt tctgaaggag aactactggt cttattgtac acttg         1600

<210> SEQ ID NO 2
<211> LENGTH: 173
<212> TYPE: PRT
<213> ORGANISM: Homo sapiens
<220> FEATURE:
<221> NAME/KEY: SIGNAL
<222> LOCATION: (1)...(17)

<400> SEQUENCE: 2

Met His Trp Lys Met Leu Leu Leu Leu Leu Tyr Tyr Asn Ala Glu
        -15             -10             -5

Ala Ser Met Cys His Arg Trp Ser Arg Ala Val Leu Phe Pro Ala Ala
    1               5               10              15

His Arg Pro Lys Arg Ser Ser Leu Pro Leu Asn Pro Val Leu Gln
                20              25              30

Thr Ser Leu Glu Glu Val Glu Leu Leu Tyr Glu Phe Leu Leu Ala Glu
            35              40              45

Leu Glu Ile Ser Pro Asp Leu Gln Ile Ser Ile Lys Asp Glu Glu Leu
        50              55              60

Ala Ser Leu Arg Lys Ala Ser Asp Phe Arg Thr Val Cys Asn Asn Val
65              70              75
```

```
Ile Pro Lys Ser Ile Pro Asp Ile Arg Arg Leu Ser Ala Ser Leu Ser
 80                  85                  90                  95

Ser His Pro Gly Ile Leu Lys Lys Glu Asp Phe Glu Arg Thr Val Leu
                100                 105                 110

Thr Leu Ala Tyr Thr Ala Tyr Arg Thr Ala Leu Ser His Gly His Gln
            115                 120                 125

Lys Asp Ile Trp Ala Gln Ser Leu Val Ser Leu Phe Gln Ala Leu Arg
        130                 135                 140

His Asp Leu Met Arg Ser Ser Gln Pro Gly Val Pro Pro
    145                 150                 155

<210> SEQ ID NO 3
<211> LENGTH: 1000
<212> TYPE: DNA
<213> ORGANISM: Homo sapiens
<220> FEATURE:
<221> NAME/KEY: CDS
<222> LOCATION: (125)...(694)

<400> SEQUENCE: 3
ggaaccaaac cagagacgcg ctgaacagag agaatcaggc tcaaagcaag tggaagtggg      60
cagagattcc accaggactg gtgcaaggcg cagagccagc cagatttgag aagaaggcaa     120 aaag atg ctg ggg agc aga gct gta atg ctg ctg ttg ctg ctg ccc tgg     169
     Met Leu Gly Ser Arg Ala Val Met Leu Leu Leu Leu Leu Pro Trp
     1               5                   10                  15 aca gct cag ggc aga gct gtg cct ggg ggc agc agc cct gcc tgg act     217
Thr Ala Gln Gly Arg Ala Val Pro Gly Gly Ser Ser Pro Ala Trp Thr
                20                  25                  30 cag tgc cag cag ctt tca cag aag ctc tgc aca ctg gcc tgg agt gca     265
Gln Cys Gln Gln Leu Ser Gln Lys Leu Cys Thr Leu Ala Trp Ser Ala
            35                  40                  45 cat cca cta gtg gga cac atg gat cta aga gaa gag gga gat gaa gag     313
His Pro Leu Val Gly His Met Asp Leu Arg Glu Glu Gly Asp Glu Glu
        50                  55                  60 act aca aat gat gtt ccc cat atc cag tgt gga gat ggc tgt gac ccc     361
Thr Thr Asn Asp Val Pro His Ile Gln Cys Gly Asp Gly Cys Asp Pro
    65                  70                  75 caa gga ctc agg gac aac agt cag ttc tgc ttg caa agg atc cac cag     409
Gln Gly Leu Arg Asp Asn Ser Gln Phe Cys Leu Gln Arg Ile His Gln
 80                  85                  90                  95 ggt ctg att ttt tat gag aag ctg cta gga tcg gat att ttc aca ggg     457
Gly Leu Ile Phe Tyr Glu Lys Leu Leu Gly Ser Asp Ile Phe Thr Gly
                100                 105                 110 gag cct tct ctg ctc cct gat agc cct gtg ggc cag ctt cat gcc tcc     505
Glu Pro Ser Leu Leu Pro Asp Ser Pro Val Gly Gln Leu His Ala Ser
            115                 120                 125 cta ctg ggc ctc agc caa ctc ctg cag cct gag ggt cac cac tgg gag     553
Leu Leu Gly Leu Ser Gln Leu Leu Gln Pro Glu Gly His His Trp Glu
        130                 135                 140 act cag cag att cca agc ctc agt ccc agc cag cca tgg cag cgt ctc     601
Thr Gln Gln Ile Pro Ser Leu Ser Pro Ser Gln Pro Trp Gln Arg Leu
    145                 150                 155 ctt ctc cgc ttc aaa atc ctt cgc agc ctc cag gcc ttt gtg gct gta     649
Leu Leu Arg Phe Lys Ile Leu Arg Ser Leu Gln Ala Phe Val Ala Val
160                 165                 170                 175 gcc gcc cgg gtc ttt gcc cat gga gca gca acc ctg agt ccc taa         694
Ala Ala Arg Val Phe Ala His Gly Ala Ala Thr Leu Ser Pro *
                180                 185
```

```
aggcagcagc tcaaggatgg cactcagatc tccatggccc agcaaggcca agataaatct     754
accaccccag gcacctgtga gccaacaggt taattagtcc attaatttta gtgggacctg     814
catatgttga aaattaccaa tactgactga catgtgatgc tgacctatga taaggttgag     874
tatttattag atgggaaggg aaatttgggg attatttatc ctcctgggga cagtttgggg     934
aggattattt attgtattta tattgaatta tgtactttt tcaataaagt cttatttttg     994
tggcta                                                                1000
```

<210> SEQ ID NO 4
<211> LENGTH: 189
<212> TYPE: PRT
<213> ORGANISM: Homo sapiens

<400> SEQUENCE: 4

```
Met Leu Gly Ser Arg Ala Val Met Leu Leu Leu Leu Pro Trp Thr
 1               5                  10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 5
<211> LENGTH: 923
<212> TYPE: DNA
<213> ORGANISM: Homo sapiens
<220> FEATURE:
<221> NAME/KEY: CDS
<222> LOCATION: (73)...(834)

<400> SEQUENCE: 5

```
cacagaagga gacagaaagc aagagaccag agtcccggga aagtcctgcc gcgcctcggg      60
acaattataa aa atg tgg ccc cct ggg tca gcc tcc cag cca ccg ccc tca    111
              Met Trp Pro Pro Gly Ser Ala Ser Gln Pro Pro Pro Ser
                1               5                  10 cct gcc gcg gcc aca ggt ctg cat cca gcg gct cgc cct gtg tcc ctg    159
Pro Ala Ala Ala Thr Gly Leu His Pro Ala Ala Arg Pro Val Ser Leu
     15                  20                  25 cag tgc cgg ctc agc atg tgt cca gcg cgc agc ctc ctc ctt gtg gct    207
Gln Cys Arg Leu Ser Met Cys Pro Ala Arg Ser Leu Leu Leu Val Ala
```

-continued

```
         30                  35                  40                  45
acc ctg gtc ctc ctg gac cac ctc agt ttg gcc aga aac ctc ccc gtg      255
Thr Leu Val Leu Leu Asp His Leu Ser Leu Ala Arg Asn Leu Pro Val
                50                  55                  60 gcc act cca gac cca gga atg ttc cca tgc ctt cac cac tcc caa aac      303
Ala Thr Pro Asp Pro Gly Met Phe Pro Cys Leu His His Ser Gln Asn
            65                  70                  75 ctg ctg agg gcc gtc agc aac atg ctc cag aag gcc aga caa act cta      351
Leu Leu Arg Ala Val Ser Asn Met Leu Gln Lys Ala Arg Gln Thr Leu
        80                  85                  90 gaa ttt tac cct tgc act tct gaa gag att gat cat gaa gat atc aca      399
Glu Phe Tyr Pro Cys Thr Ser Glu Glu Ile Asp His Glu Asp Ile Thr
    95                  100                 105 aaa gat aaa acc agc aca gtg gag gcc tgt tta cca ttg gaa tta acc      447
Lys Asp Lys Thr Ser Thr Val Glu Ala Cys Leu Pro Leu Glu Leu Thr
110                 115                 120                 125 aag aat gag agt tgc cta aat tcc aga gag acc tct ttc ata act aat      495
Lys Asn Glu Ser Cys Leu Asn Ser Arg Glu Thr Ser Phe Ile Thr Asn
                130                 135                 140 ggg agt tgc ctg gcc tcc aga aag acc tct ttt atg atg gcc ctg tgc      543
Gly Ser Cys Leu Ala Ser Arg Lys Thr Ser Phe Met Met Ala Leu Cys
            145                 150                 155 ctt agt agt att tat gaa gac ttg aag atg tac cag gtg gag ttc aag      591
Leu Ser Ser Ile Tyr Glu Asp Leu Lys Met Tyr Gln Val Glu Phe Lys
        160                 165                 170 acc atg aat gca aag ctt ctg atg gat cct aag agg cag atc ttt cta      639
Thr Met Asn Ala Lys Leu Leu Met Asp Pro Lys Arg Gln Ile Phe Leu
    175                 180                 185 gat caa aac atg ctg gca gtt att gat gag ctg atg cag gcc ctg aat      687
Asp Gln Asn Met Leu Ala Val Ile Asp Glu Leu Met Gln Ala Leu Asn
190                 195                 200                 205 ttc aac agt gag act gtg cca caa aaa tcc tcc ctt gaa gaa ccg gat      735
Phe Asn Ser Glu Thr Val Pro Gln Lys Ser Ser Leu Glu Glu Pro Asp
                210                 215                 220 ttt tat aaa act aaa atc aag ctc tgc ata ctt ctt cat gct ttc aga      783
Phe Tyr Lys Thr Lys Ile Lys Leu Cys Ile Leu Leu His Ala Phe Arg
            225                 230                 235 att cgg gca gtg act att gat aga gtg atg agc tat ctg aat gct tcc      831
Ile Arg Ala Val Thr Ile Asp Arg Val Met Ser Tyr Leu Asn Ala Ser
        240                 245                 250 taa aaagcgaggt ccctccaaac cgttgtcatt tttataaaac tttgaaatga          884
* ggaaactttg ataggatgtg gattaagaac tagggaggg                           923
```

<210> SEQ ID NO 6
<211> LENGTH: 253
<212> TYPE: PRT
<213> ORGANISM: Homo sapiens

<400> SEQUENCE: 6

```
Met Trp Pro Pro Gly Ser Ala Ser Gln Pro Pro Ser Pro Ala Ala
  1               5                  10                  15

Ala Thr Gly Leu His Pro Ala Ala Arg Pro Val Ser Leu Gln Cys Arg
             20                  25                  30

Leu Ser Met Cys Pro Ala Arg Ser Leu Leu Leu Val Ala Thr Leu Val
         35                  40                  45

Leu Leu Asp His Leu Ser Leu Ala Arg Asn Leu Pro Val Ala Thr Pro
     50                  55                  60
```

```
Asp Pro Gly Met Phe Pro Cys Leu His His Ser Gln Asn Leu Leu Arg
 65                  70                  75                  80

Ala Val Ser Asn Met Leu Gln Lys Ala Arg Gln Thr Leu Glu Phe Tyr
                 85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 7
<211> LENGTH: 39
<212> TYPE: DNA
<213> ORGANISM: Artificial Sequence
<220> FEATURE:
<223> OTHER INFORMATION: oligonucleotide primer ZC50071

<400> SEQUENCE: 7
ggtgtccagg gaattcgcaa gatgcattgg aagatgttg                    39

<210> SEQ ID NO 8
<211> LENGTH: 72
<212> TYPE: DNA
<213> ORGANISM: Artificial Sequence
<220> FEATURE:
<223> OTHER INFORMATION: oligonucleotide primer ZC50076

<400> SEQUENCE: 8
ctctagatta agatctcact tatcgtcatc gtccttatag tcgccaccgg atccgggagg    60
tactcccggc tg                                                       72

<210> SEQ ID NO 9
<211> LENGTH: 35
<212> TYPE: DNA
<213> ORGANISM: Artificial Sequence
<220> FEATURE:
<223> OTHER INFORMATION: oligonucleotide primer ZC50056

<400> SEQUENCE: 9
caggccaagt tgtattgttt gtctgccttt gtagc                        35

<210> SEQ ID NO 10
<211> LENGTH: 202
<212> TYPE: PRT
<213> ORGANISM: Homo sapiens
```

```
<400> SEQUENCE: 10

Met Lys Val Leu Ala Ala Gly Val Val Pro Leu Leu Leu Val Leu His
 1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Leu Gly Cys Gln Leu Leu Gly Lys Tyr Lys
            180                 185                 190

Gln Ile Ile Ala Val Leu Ala Gln Ala Phe
        195                 200

<210> SEQ ID NO 11
<211> LENGTH: 25
<212> TYPE: DNA
<213> ORGANISM: Artificial Sequence
<220> FEATURE:
<223> OTHER INFORMATION: oligonucleotide primer ZC41011

<400> SEQUENCE: 11
ctctccatcc ttatctttca tcaac                                  25

<210> SEQ ID NO 12
<211> LENGTH: 24
<212> TYPE: DNA
<213> ORGANISM: Artificial Sequence
<220> FEATURE:
<223> OTHER INFORMATION: oligonucleotide primer ZC41012

<400> SEQUENCE: 12
ctctctgctg gctaaacaaa acac                                   24

<210> SEQ ID NO 13
<211> LENGTH: 26
<212> TYPE: DNA
<213> ORGANISM: Artificial Sequence
<220> FEATURE:
<223> OTHER INFORMATION: oligonucleotide primer ZC42901

<400> SEQUENCE: 13
ctcatattgc tcaactgtgt gaaaag                                 26
```

```
<210> SEQ ID NO 14
<211> LENGTH: 25
<212> TYPE: DNA
<213> ORGANISM: Artificial Sequence
<220> FEATURE:
<223> OTHER INFORMATION: oligonucleotide primer ZC42902

<400> SEQUENCE: 14
tagaagccac ctgaacacaa atctg                                          25

<210> SEQ ID NO 15
<211> LENGTH: 25
<212> TYPE: DNA
<213> ORGANISM: Artificial Sequence
<220> FEATURE:
<223> OTHER INFORMATION: oligonucleotide primer ZC16909

<400> SEQUENCE: 15
cacagaagga gacagaaagc aagag                                          25

<210> SEQ ID NO 16
<211> LENGTH: 20
<212> TYPE: DNA
<213> ORGANISM: Artificial Sequence
<220> FEATURE:
<223> OTHER INFORMATION: oligonucleotide primer ZC45224

<400> SEQUENCE: 16
ggtgaaggca tgggaacatt                                                20

<210> SEQ ID NO 17
<211> LENGTH: 23
<212> TYPE: DNA
<213> ORGANISM: Artificial Sequence
<220> FEATURE:
<223> OTHER INFORMATION: oligonucleotide primer ZC49543

<400> SEQUENCE: 17
gccattcgct cctgctgctt cac                                            23

<210> SEQ ID NO 18
<211> LENGTH: 25
<212> TYPE: DNA
<213> ORGANISM: Artificial Sequence
<220> FEATURE:
<223> OTHER INFORMATION: oligonucleotide primer ZC49544

<400> SEQUENCE: 18
cctctgctgc ttttgacact gaatg                                          25

<210> SEQ ID NO 19
<211> LENGTH: 25
<212> TYPE: DNA
<213> ORGANISM: Artificial Sequence
<220> FEATURE:
<223> OTHER INFORMATION: oligonucleotide primer ZC49302

<400> SEQUENCE: 19
tctaagagaa gagggagatg aagag                                          25

<210> SEQ ID NO 20
<211> LENGTH: 24
<212> TYPE: DNA
<213> ORGANISM: Artificial Sequence
<220> FEATURE:
<223> OTHER INFORMATION: oligonucleotide primer ZC49303
```

```
<400> SEQUENCE: 20
tggaggctgc aaggattttt gaag                                      24

<210> SEQ ID NO 21
<211> LENGTH: 25
<212> TYPE: DNA
<213> ORGANISM: Artificial Sequence
<220> FEATURE:
<223> OTHER INFORMATION: oligonucleotide primer ZC16908

<400> SEQUENCE: 21
cagccatgac cccgcagctt ctcct                                     25

<210> SEQ ID NO 22
<211> LENGTH: 20
<212> TYPE: DNA
<213> ORGANISM: Artificial Sequence
<220> FEATURE:
<223> OTHER INFORMATION: oligonucleotide primer ZC44196

<400> SEQUENCE: 22
acattgagca cgtagggagc                                           20

<210> SEQ ID NO 23
<211> LENGTH: 19
<212> TYPE: DNA
<213> ORGANISM: Artificial Sequence
<220> FEATURE:
<223> OTHER INFORMATION: oligonucleotide primer ZC50352

<400> SEQUENCE: 23
tgccattgaa cccagtcct                                            19

<210> SEQ ID NO 24
<211> LENGTH: 18
<212> TYPE: DNA
<213> ORGANISM: Artificial Sequence
<220> FEATURE:
<223> OTHER INFORMATION: oligonucleotide primer ZC50354

<400> SEQUENCE: 24
taggccaggg tcagcact                                             18

<210> SEQ ID NO 25
<211> LENGTH: 22
<212> TYPE: DNA
<213> ORGANISM: Artificial Sequence
<220> FEATURE:
<223> OTHER INFORMATION: oligonucleotide primer ZC28200

<400> SEQUENCE: 25
gtccctcatc agcctattcc ag                                        22

<210> SEQ ID NO 26
<211> LENGTH: 23
<212> TYPE: DNA
<213> ORGANISM: Artificial Sequence
<220> FEATURE:
<223> OTHER INFORMATION: oligonucleotide primer ZC28757

<400> SEQUENCE: 26
gtagaggatg aaagttctag aag                                       23

<210> SEQ ID NO 27
<211> LENGTH: 20
```

```
<212> TYPE: DNA
<213> ORGANISM: Artificial Sequence
<220> FEATURE:
<223> OTHER INFORMATION: oligonucleotide primer ZC38398

<400> SEQUENCE: 27
gcagcgcatc gccttctatc                                                      20

<210> SEQ ID NO 28
<211> LENGTH: 82
<212> TYPE: DNA
<213> ORGANISM: Artificial Sequence
<220> FEATURE:
<223> OTHER INFORMATION: oligonucleotide primer ZC50131

<400> SEQUENCE: 28
gaaatccatg ccgagttgag acgcttccgt agacatcacc atcaccatca cggatctggt         60
ggaccaaaga ggtcctcatc ac                                                   82

<210> SEQ ID NO 29
<211> LENGTH: 72
<212> TYPE: DNA
<213> ORGANISM: Artificial Sequence
<220> FEATURE:
<223> OTHER INFORMATION: oligonucleotide primer ZC50080

<400> SEQUENCE: 29
tccggctcct ccgcttcctc cgcttccaga gccgcctcta ctactgccag atccggagg          60 tactcccggc tg                                                              72

<210> SEQ ID NO 30
<211> LENGTH: 60
<212> TYPE: DNA
<213> ORGANISM: Artificial Sequence
<220> FEATURE:
<223> OTHER INFORMATION: oligonucleotide primer ZC50085

<400> SEQUENCE: 30
ggctctggaa gcggaggaag cggaggagcc ggaagtaaac tgagagctgt gcctggggc          60

<210> SEQ ID NO 31
<211> LENGTH: 62
<212> TYPE: DNA
<213> ORGANISM: Artificial Sequence
<220> FEATURE:
<223> OTHER INFORMATION: oligonucleotide ZC50082

<400> SEQUENCE: 31
ggggtgggta caaccccaga gctgttttaa ggcgcgcctc tagattaggg actcagggtt         60
gc                                                                         62

<210> SEQ ID NO 32
<211> LENGTH: 63
<212> TYPE: DNA
<213> ORGANISM: Artificial Sequence
<220> FEATURE:
<223> OTHER INFORMATION: carboxy terminal linker
<220> FEATURE:
<221> NAME/KEY: CDS
<222> LOCATION: (1)...(63)

<400> SEQUENCE: 32 gga tct ggc agt agt aga ggc ggc tct gga agc gga gga agc gga gga          48
Gly Ser Gly Ser Ser Arg Gly Gly Ser Gly Ser Gly Gly Ser Gly Gly
1               5                   10                  15
```

```
gcc gga agt aaa ctg                                                 63
Ala Gly Ser Lys Leu
        20

<210> SEQ ID NO 33
<211> LENGTH: 21
<212> TYPE: PRT
<213> ORGANISM: Artificial Sequence
<220> FEATURE:
<223> OTHER INFORMATION: carboxy terminal linker

<400> SEQUENCE: 33

Gly Ser Gly Ser Ser Arg Gly Gly Ser Gly Ser Gly Gly Ser Gly Gly
 1               5                  10                  15

Ala Gly Ser Lys Leu
        20

<210> SEQ ID NO 34
<211> LENGTH: 77
<212> TYPE: DNA
<213> ORGANISM: Artificial Sequence
<220> FEATURE:
<223> OTHER INFORMATION: oligonucleotide ZC50765

<400> SEQUENCE: 34
agtagtagag gcggctctgg aagcggagga agcggaggag ccggaagtaa actgtggagc     60
agggctgtgc tcttccc                                                   77

<210> SEQ ID NO 35
<211> LENGTH: 77
<212> TYPE: DNA
<213> ORGANISM: Artificial Sequence
<220> FEATURE:
<223> OTHER INFORMATION: oligonucleotide ZC50766

<400> SEQUENCE: 35
agtagtagag gcggctctgg aagcggagga agcggaggag ccggaagtaa actgtcctca     60
tcactgccat tgaaccc                                                   77

<210> SEQ ID NO 36
<211> LENGTH: 64
<212> TYPE: DNA
<213> ORGANISM: Artificial Sequence
<220> FEATURE:
<223> OTHER INFORMATION: oligonucleotide ZC50768

<400> SEQUENCE: 36
ccccagagct gttttaaggc gcgcctctag attaagatct tcagtgatgg tgatggtgat     60
gtcc                                                                 64

<210> SEQ ID NO 37
<211> LENGTH: 63
<212> TYPE: DNA
<213> ORGANISM: Artificial Sequence
<220> FEATURE:
<223> OTHER INFORMATION: amino terminal linker
<220> FEATURE:
<221> NAME/KEY: CDS
<222> LOCATION: (1)...(63)

<400> SEQUENCE: 37 gga tct ggc agt agt aga ggc ggc tct gga agc gga gga agc gga gga     48
Gly Ser Gly Ser Ser Arg Gly Gly Ser Gly Ser Gly Gly Ser Gly Gly
 1               5                  10                  15
```

```
gcc gga agt aaa ctg                                              63
Ala Gly Ser Lys Leu
          20

<210> SEQ ID NO 38
<211> LENGTH: 21
<212> TYPE: PRT
<213> ORGANISM: Artificial Sequence
<220> FEATURE:
<223> OTHER INFORMATION: amino terminal linker

<400> SEQUENCE: 38

Gly Ser Gly Ser Ser Arg Gly Gly Ser Gly Ser Gly Gly Ser Gly Gly
 1               5                  10                  15

Ala Gly Ser Lys Leu
          20

<210> SEQ ID NO 39
<211> LENGTH: 65
<212> TYPE: DNA
<213> ORGANISM: Artificial Sequence
<220> FEATURE:
<223> OTHER INFORMATION: oligonucleotide ZC50767

<400> SEQUENCE: 39
tttctctcca caggtgtcca gggaattcat ataggccggc caccatgctg gggagcagag    60
ctgta                                                                65

<210> SEQ ID NO 40
<211> LENGTH: 75
<212> TYPE: DNA
<213> ORGANISM: Artificial Sequence
<220> FEATURE:
<223> OTHER INFORMATION: oligonucleotide ZC50769

<400> SEQUENCE: 40
tccggctcct ccgcttcctc cgcttccaga gccgcctcta ctactgccag atccgggact    60
cagggttgct gctcc                                                     75

<210> SEQ ID NO 41
<211> LENGTH: 60
<212> TYPE: DNA
<213> ORGANISM: Artificial Sequence
<220> FEATURE:
<223> OTHER INFORMATION: oligonucleotide ZC50660

<400> SEQUENCE: 41
caggaaatcc atgccgagtt gagacgcttc cgtagatctt tgtcactgcc attgaatcca    60

<210> SEQ ID NO 42
<211> LENGTH: 74
<212> TYPE: DNA
<213> ORGANISM: Artificial Sequence
<220> FEATURE:
<223> OTHER INFORMATION: oligonucleotide ZC50658

<400> SEQUENCE: 42
tccggctcct ccgcttcctc cgcttccaga gccgcctcta ctactgccag atccggatga    60
cacagcaggg ctcg                                                      74

<210> SEQ ID NO 43
<211> LENGTH: 72
<212> TYPE: DNA
```

```
<213> ORGANISM: Artificial Sequence
<220> FEATURE:
<223> OTHER INFORMATION: oligonucleotide ZC50659

<400> SEQUENCE: 43
agtagaggcg gctctggaag cggaggaagc ggaggagccg aagtaaaact ggtgcctagg     60
agtagcagtc ct                                                        72

<210> SEQ ID NO 44
<211> LENGTH: 88
<212> TYPE: DNA
<213> ORGANISM: Artificial Sequence
<220> FEATURE:
<223> OTHER INFORMATION: oligonucleotide ZC50657

<400> SEQUENCE: 44
ctggggtggg tacaacccca gagctgtttt aaggcgcgcc tctagattag tgatggtgat     60
ggtgatgagc tgttggcact aagggctc                                       88

<210> SEQ ID NO 45
<211> LENGTH: 79
<212> TYPE: DNA
<213> ORGANISM: Artificial Sequence
<220> FEATURE:
<223> OTHER INFORMATION: oligonucleotide ZC51016

<400> SEQUENCE: 45
acatccactt tgcctttctc tccacaggtg tccagggaat tcatataggc cgggcaagat     60
gtggccccct gggtcagcc                                                 79

<210> SEQ ID NO 46
<211> LENGTH: 76
<212> TYPE: DNA
<213> ORGANISM: Artificial Sequence
<220> FEATURE:
<223> OTHER INFORMATION: oligonucleotide ZC51017

<400> SEQUENCE: 46
tccggctcct ccgcttcctc cgcttccaga gccgcctcta ctactgccag atccggaagc     60
attcagatag ctcatc                                                    76

<210> SEQ ID NO 47
<211> LENGTH: 80
<212> TYPE: DNA
<213> ORGANISM: Artificial Sequence
<220> FEATURE:
<223> OTHER INFORMATION: oligonucleotide ZC51754

<400> SEQUENCE: 47
ctggcagtag tagaggcggc tctggaagcg gaggaagcgg aggagccgga agtaaactga     60
ggtggagcag ggccgcactg                                                80

<210> SEQ ID NO 48
<211> LENGTH: 93
<212> TYPE: DNA
<213> ORGANISM: Artificial Sequence
<220> FEATURE:
<223> OTHER INFORMATION: oligonucleotide ZC51759

<400> SEQUENCE: 48
tgggtacaac cccagagctg ttttaaggcg cgcctctaga ttagtgatgg tgatggtgat     60
gtccaccaga tccggatgac acagcagggc tcg                                 93
```

<210> SEQ ID NO 49
<211> LENGTH: 1116
<212> TYPE: DNA
<213> ORGANISM: Artificial Sequence
<220> FEATURE:
<223> OTHER INFORMATION: zcyto33f2cHIS (W23)
<220> FEATURE:
<221> NAME/KEY: CDS
<222> LOCATION: (1)...(1116)

<400> SEQUENCE: 49

| | | | | | | | | | | | | | | | | |
|---|---|---|---|---|---|---|---|---|---|---|---|---|---|---|---|---|
| atg | ctg | ggg | agc | aga | gct | gta | atg | ctg | ctg | ttg | ctg | ctg | ccc | tgg | aca | 48 |
| Met | Leu | Gly | Ser | Arg | Ala | Val | Met | Leu | Leu | Leu | Leu | Leu | Pro | Trp | Thr | |
| 1 | | | | 5 | | | | | 10 | | | | | 15 | | |
| gct | cag | ggc | aga | gct | gtg | cct | ggg | ggc | agc | agc | cct | gcc | tgg | act | cag | 96 |
| Ala | Gln | Gly | Arg | Ala | Val | Pro | Gly | Gly | Ser | Ser | Pro | Ala | Trp | Thr | Gln | |
| | | | 20 | | | | | 25 | | | | | 30 | | | |
| tgc | cag | cag | ctt | tca | cag | aag | ctc | tgc | aca | ctg | gcc | tgg | agt | gca | cat | 144 |
| Cys | Gln | Gln | Leu | Ser | Gln | Lys | Leu | Cys | Thr | Leu | Ala | Trp | Ser | Ala | His | |
| | 35 | | | | | 40 | | | | | 45 | | | | | |
| cca | cta | gtg | gga | cac | atg | gat | cta | aga | gaa | gag | gga | gat | gaa | gag | act | 192 |
| Pro | Leu | Val | Gly | His | Met | Asp | Leu | Arg | Glu | Glu | Gly | Asp | Glu | Glu | Thr | |
| 50 | | | | | 55 | | | | | 60 | | | | | | |
| aca | aat | gat | gtt | ccc | cat | atc | cag | tgt | gga | gat | ggc | tgt | gac | ccc | caa | 240 |
| Thr | Asn | Asp | Val | Pro | His | Ile | Gln | Cys | Gly | Asp | Gly | Cys | Asp | Pro | Gln | |
| 65 | | | | 70 | | | | | 75 | | | | | 80 | | |
| gga | ctc | agg | gac | aac | agt | cag | ttc | tgc | ttg | caa | agg | atc | cac | cag | ggt | 288 |
| Gly | Leu | Arg | Asp | Asn | Ser | Gln | Phe | Cys | Leu | Gln | Arg | Ile | His | Gln | Gly | |
| | | | | 85 | | | | | 90 | | | | | 95 | | |
| ctg | att | ttt | tat | gag | aag | ctg | cta | gga | tcg | gat | att | ttc | aca | ggg | gag | 336 |
| Leu | Ile | Phe | Tyr | Glu | Lys | Leu | Leu | Gly | Ser | Asp | Ile | Phe | Thr | Gly | Glu | |
| | | | 100 | | | | | 105 | | | | | 110 | | | |
| cct | tct | ctg | ctc | cct | gat | agc | cct | gtg | ggc | cag | ctt | cat | gcc | tcc | cta | 384 |
| Pro | Ser | Leu | Leu | Pro | Asp | Ser | Pro | Val | Gly | Gln | Leu | His | Ala | Ser | Leu | |
| | 115 | | | | | 120 | | | | | 125 | | | | | |
| ctg | ggc | ctc | agc | caa | ctc | ctg | cag | cct | gag | ggt | cac | cac | tgg | gag | act | 432 |
| Leu | Gly | Leu | Ser | Gln | Leu | Leu | Gln | Pro | Glu | Gly | His | His | Trp | Glu | Thr | |
| 130 | | | | | 135 | | | | | 140 | | | | | | |
| cag | cag | att | cca | agc | ctc | agt | ccc | agc | cag | cca | tgg | cag | cgt | ctc | ctt | 480 |
| Gln | Gln | Ile | Pro | Ser | Leu | Ser | Pro | Ser | Gln | Pro | Trp | Gln | Arg | Leu | Leu | |
| 145 | | | | | 150 | | | | | 155 | | | | | 160 | |
| ctc | cgc | ttc | aaa | atc | ctt | cgc | agc | ctc | cag | gcc | ttt | gtg | gct | gta | gcc | 528 |
| Leu | Arg | Phe | Lys | Ile | Leu | Arg | Ser | Leu | Gln | Ala | Phe | Val | Ala | Val | Ala | |
| | | | 165 | | | | | 170 | | | | | 175 | | | |
| gcc | cgg | gtc | ttt | gcc | cat | gga | gca | gca | acc | ctg | agt | ccc | gga | tct | ggc | 576 |
| Ala | Arg | Val | Phe | Ala | His | Gly | Ala | Ala | Thr | Leu | Ser | Pro | Gly | Ser | Gly | |
| | | 180 | | | | | 185 | | | | | 190 | | | | |
| agt | agt | aga | ggc | ggc | tct | gga | agc | gga | gga | agc | gga | gga | gcc | gga | agt | 624 |
| Ser | Ser | Arg | Gly | Gly | Ser | Gly | Ser | Gly | Gly | Ser | Gly | Gly | Ala | Gly | Ser | |
| | | 195 | | | | | 200 | | | | | 205 | | | | |
| aaa | ctg | tgg | agc | agg | gct | gtg | ctc | ttc | cct | gcc | gcc | cac | cgg | cca | aag | 672 |
| Lys | Leu | Trp | Ser | Arg | Ala | Val | Leu | Phe | Pro | Ala | Ala | His | Arg | Pro | Lys | |
| 210 | | | | | 215 | | | | | 220 | | | | | | |
| agg | tcc | tca | tca | ctg | cca | ttg | aac | cca | gtc | ctg | cag | acc | tcc | ctg | gag | 720 |
| Arg | Ser | Ser | Ser | Leu | Pro | Leu | Asn | Pro | Val | Leu | Gln | Thr | Ser | Leu | Glu | |
| 225 | | | | | 230 | | | | | 235 | | | | | 240 | |
| gag | gtg | gag | ctg | ctc | tac | gag | ttc | ctg | ctg | gcc | gaa | ctt | gag | atc | agc | 768 |
| Glu | Val | Glu | Leu | Leu | Tyr | Glu | Phe | Leu | Leu | Ala | Glu | Leu | Glu | Ile | Ser | |
| | | | | 245 | | | | | 250 | | | | | 255 | | |
| cct | gac | ctg | cag | atc | tcc | atc | aag | gac | gag | gag | ctg | gcc | tcc | ttg | cgg | 816 |
| | | | | | | | | | | | | | | | | |

| | | | | | | | | | | | | |
|---|---|---|---|---|---|---|---|---|---|---|---|---|
| Pro | Asp | Leu | Gln | Ile | Ser | Ile | Lys | Asp | Glu | Leu | Ala | Ser | Leu | Arg |
| | | | 260 | | | | | 265 | | | | 270 | | |

| aag | gcc | tca | gac | ttc | cgc | acc | gtc | tgc | aac | aac | gtc | atc | ccc | aag | agc | 864 |
|---|---|---|---|---|---|---|---|---|---|---|---|---|---|---|---|---|
| Lys | Ala | Ser | Asp | Phe | Arg | Thr | Val | Cys | Asn | Asn | Val | Ile | Pro | Lys | Ser | |
| | | 275 | | | | | 280 | | | | | 285 | | | | |

| atc | cca | gac | atc | cgc | cgg | ctc | agc | gcc | agc | ctc | tcc | agc | cac | cct | ggc | 912 |
|---|---|---|---|---|---|---|---|---|---|---|---|---|---|---|---|---|
| Ile | Pro | Asp | Ile | Arg | Arg | Leu | Ser | Ala | Ser | Leu | Ser | Ser | His | Pro | Gly | |
| 290 | | | | | 295 | | | | | 300 | | | | | | |

| atc | ctc | aag | aaa | gaa | gac | ttt | gaa | agg | aca | gtg | ctg | acc | ctg | gcc | tac | 960 |
|---|---|---|---|---|---|---|---|---|---|---|---|---|---|---|---|---|
| Ile | Leu | Lys | Lys | Glu | Asp | Phe | Glu | Arg | Thr | Val | Leu | Thr | Leu | Ala | Tyr | |
| 305 | | | | | 310 | | | | | 315 | | | | | 320 | |

| aca | gcc | tac | cgc | aca | gcc | ctg | tcc | cac | ggc | cat | cag | aag | gac | atc | tgg | 1008 |
|---|---|---|---|---|---|---|---|---|---|---|---|---|---|---|---|---|
| Thr | Ala | Tyr | Arg | Thr | Ala | Leu | Ser | His | Gly | His | Gln | Lys | Asp | Ile | Trp | |
| | | | 325 | | | | | 330 | | | | | 335 | | | |

| gcg | cag | tcc | ctc | gtt | agc | ctc | ttc | cag | gcc | ctg | agg | cac | gac | ttg | atg | 1056 |
|---|---|---|---|---|---|---|---|---|---|---|---|---|---|---|---|---|
| Ala | Gln | Ser | Leu | Val | Ser | Leu | Phe | Gln | Ala | Leu | Arg | His | Asp | Leu | Met | |
| | | 340 | | | | | 345 | | | | | 350 | | | | |

| cgc | tcc | tca | cag | ccg | gga | gta | cct | ccc | ggt | tct | gga | gga | cat | cac | cat | 1104 |
|---|---|---|---|---|---|---|---|---|---|---|---|---|---|---|---|---|
| Arg | Ser | Ser | Gln | Pro | Gly | Val | Pro | Pro | Gly | Ser | Gly | Gly | His | His | His | |
| | 355 | | | | | 360 | | | | | 365 | | | | | |

| cac | cat | cac | tga | 1116 |
|---|---|---|---|---|
| His | His | His | * | |
| 370 | | | | |

```
<210> SEQ ID NO 50
<211> LENGTH: 371
<212> TYPE: PRT
<213> ORGANISM: Artificial Sequence
<220> FEATURE:
<223> OTHER INFORMATION: zcyto33f2cHIS (W23)

<400> SEQUENCE: 50
```

| | | | | | | | | | | | | | | |
|---|---|---|---|---|---|---|---|---|---|---|---|---|---|---|
| Met | Leu | Gly | Ser | Arg | Ala | Val | Met | Leu | Leu | Leu | Leu | Pro | Trp | Thr |
| 1 | | | | 5 | | | | | 10 | | | | | 15 |
| Ala | Gln | Gly | Arg | Ala | Val | Pro | Gly | Gly | Ser | Ser | Pro | Ala | Trp | Thr | Gln |
| | | | 20 | | | | | 25 | | | | | 30 | | |
| Cys | Gln | Gln | Leu | Ser | Gln | Lys | Leu | Cys | Thr | Leu | Ala | Trp | Ser | Ala | His |
| | | 35 | | | | | 40 | | | | | 45 | | | |
| Pro | Leu | Val | Gly | His | Met | Asp | Leu | Arg | Glu | Glu | Gly | Asp | Glu | Glu | Thr |
| | 50 | | | | | 55 | | | | | 60 | | | | |
| Thr | Asn | Asp | Val | Pro | His | Ile | Gln | Cys | Gly | Asp | Gly | Cys | Asp | Pro | Gln |
| 65 | | | | | 70 | | | | | 75 | | | | | 80 |
| Gly | Leu | Arg | Asp | Asn | Ser | Gln | Phe | Cys | Leu | Gln | Arg | Ile | His | Gln | Gly |
| | | | | 85 | | | | | 90 | | | | | 95 | |
| Leu | Ile | Phe | Tyr | Glu | Lys | Leu | Leu | Gly | Ser | Asp | Ile | Phe | Thr | Gly | Glu |
| | | | 100 | | | | | 105 | | | | | 110 | | |
| Pro | Ser | Leu | Leu | Pro | Asp | Ser | Pro | Val | Gly | Gln | Leu | His | Ala | Ser | Leu |
| | | 115 | | | | | 120 | | | | | 125 | | | |
| Leu | Gly | Leu | Ser | Gln | Leu | Leu | Gln | Pro | Glu | Gly | His | His | Trp | Glu | Thr |
| | 130 | | | | | 135 | | | | | 140 | | | | |
| Gln | Gln | Ile | Pro | Ser | Leu | Ser | Pro | Ser | Gln | Pro | Trp | Gln | Arg | Leu | Leu |
| 145 | | | | | 150 | | | | | 155 | | | | | 160 |
| Leu | Arg | Phe | Lys | Ile | Leu | Arg | Ser | Leu | Gln | Ala | Phe | Val | Ala | Val | Ala |
| | | | | 165 | | | | | 170 | | | | | 175 | |
| Ala | Arg | Val | Phe | Ala | His | Gly | Ala | Ala | Thr | Leu | Ser | Pro | Gly | Ser | Gly |
| | | | 180 | | | | | 185 | | | | | 190 | | |
| Ser | Ser | Arg | Gly | Gly | Ser | Gly | Gly | Ser | Gly | Gly | Ala | Gly | Ser | | |
| | | 195 | | | | | 200 | | | | | 205 | | | |

```
Lys Leu Trp Ser Arg Ala Val Leu Phe Pro Ala Ala His Arg Pro Lys
    210                 215                 220

Arg Ser Ser Ser Leu Pro Leu Asn Pro Val Leu Gln Thr Ser Leu Glu
225                 230                 235                 240

Glu Val Glu Leu Leu Tyr Glu Phe Leu Leu Ala Glu Leu Glu Ile Ser
                245                 250                 255

Pro Asp Leu Gln Ile Ser Ile Lys Asp Glu Glu Leu Ala Ser Leu Arg
                260                 265                 270

Lys Ala Ser Asp Phe Arg Thr Val Cys Asn Asn Val Ile Pro Lys Ser
            275                 280                 285

Ile Pro Asp Ile Arg Arg Leu Ser Ala Ser Leu Ser Ser His Pro Gly
        290                 295                 300

Ile Leu Lys Lys Glu Asp Phe Glu Arg Thr Val Leu Thr Leu Ala Tyr
305                 310                 315                 320

Thr Ala Tyr Arg Thr Ala Leu Ser His Gly His Gln Lys Asp Ile Trp
                325                 330                 335

Ala Gln Ser Leu Val Ser Leu Phe Gln Ala Leu Arg His Asp Leu Met
            340                 345                 350

Arg Ser Ser Gln Pro Gly Val Pro Pro Gly Ser Gly His His His
        355                 360                 365

His His His
    370

<210> SEQ ID NO 51
<211> LENGTH: 1071
<212> TYPE: DNA
<213> ORGANISM: Artificial Sequence
<220> FEATURE:
<223> OTHER INFORMATION: zcyto33F2cHis (S38)
<220> FEATURE:
<221> NAME/KEY: CDS
<222> LOCATION: (1)...(1071)

<400> SEQUENCE: 51 atg ctg ggg agc aga gct gta atg ctg ctg ttg ctg ctg ccc tgg aca      48
Met Leu Gly Ser Arg Ala Val Met Leu Leu Leu Leu Leu Pro Trp Thr
 1               5                  10                  15 gct cag ggc aga gct gtg cct ggg ggc agc agc cct gcc tgg act cag      96
Ala Gln Gly Arg Ala Val Pro Gly Gly Ser Ser Pro Ala Trp Thr Gln
             20                  25                  30 tgc cag cag ctt tca cag aag ctc tgc aca ctg gcc tgg agt gca cat     144
Cys Gln Gln Leu Ser Gln Lys Leu Cys Thr Leu Ala Trp Ser Ala His
         35                  40                  45 cca cta gtg gga cac atg gat cta aga gaa gag gga gat gaa gag act     192
Pro Leu Val Gly His Met Asp Leu Arg Glu Glu Gly Asp Glu Glu Thr
     50                  55                  60 aca aat gat gtt ccc cat atc cag tgt gga gat ggc tgt gac ccc caa     240
Thr Asn Asp Val Pro His Ile Gln Cys Gly Asp Gly Cys Asp Pro Gln
 65                  70                  75                  80 gga ctc agg gac aac agt cag ttc tgc ttg caa agg atc cac cag ggt     288
Gly Leu Arg Asp Asn Ser Gln Phe Cys Leu Gln Arg Ile His Gln Gly
                 85                  90                  95 ctg att ttt tat gag aag ctg cta gga tcg gat att ttc aca ggg gag     336
Leu Ile Phe Tyr Glu Lys Leu Leu Gly Ser Asp Ile Phe Thr Gly Glu
            100                 105                 110 cct tct ctg ctc cct gat agc cct gtg ggc cag ctt cat gcc tcc cta     384
Pro Ser Leu Leu Pro Asp Ser Pro Val Gly Gln Leu His Ala Ser Leu
        115                 120                 125
```

```
ctg ggc ctc agc caa ctc ctg cag cct gag ggt cac cac tgg gag act    432
Leu Gly Leu Ser Gln Leu Leu Gln Pro Glu Gly His His Trp Glu Thr
    130                 135                 140 cag cag att cca agc ctc agt ccc agc cag cca tgg cag cgt ctc ctt    480
Gln Gln Ile Pro Ser Leu Ser Pro Ser Gln Pro Trp Gln Arg Leu Leu
145                 150                 155                 160 ctc cgc ttc aaa atc ctt cgc agc ctc cag gcc ttt gtg gct gta gcc    528
Leu Arg Phe Lys Ile Leu Arg Ser Leu Gln Ala Phe Val Ala Val Ala
                165                 170                 175 gcc cgg gtc ttt gcc cat gga gca gca acc ctg agt ccc gga tct ggc    576
Ala Arg Val Phe Ala His Gly Ala Ala Thr Leu Ser Pro Gly Ser Gly
        180                 185                 190 agt agt aga ggc ggc tct gga agc gga gga agc gga gga gcc gga agt    624
Ser Ser Arg Gly Gly Ser Gly Ser Gly Gly Ser Gly Gly Ala Gly Ser
    195                 200                 205 aaa ctg tcc tca tca ctg cca ttg aac cca gtc ctg cag acc tcc ctg    672
Lys Leu Ser Ser Ser Leu Pro Leu Asn Pro Val Leu Gln Thr Ser Leu
210                 215                 220 gag gag gtg gag ctg ctc tac gag ttc ctg ctg gcc gaa ctt gag atc    720
Glu Glu Val Glu Leu Leu Tyr Glu Phe Leu Leu Ala Glu Leu Glu Ile
225                 230                 235                 240 agc cct gac ctg cag atc tcc atc aag gac gag gag ctg gcc tcc ttg    768
Ser Pro Asp Leu Gln Ile Ser Ile Lys Asp Glu Glu Leu Ala Ser Leu
                245                 250                 255 cgg aag gcc tca gac ttc cgc acc gtc tgc aac aac gtc atc ccc aag    816
Arg Lys Ala Ser Asp Phe Arg Thr Val Cys Asn Asn Val Ile Pro Lys
            260                 265                 270 agc atc cca gac atc cgc cgg ctc agc gcc agc ctc tcc agc cac cct    864
Ser Ile Pro Asp Ile Arg Arg Leu Ser Ala Ser Leu Ser Ser His Pro
        275                 280                 285 ggc atc ctc aag aaa gaa gac ttt gaa agg aca gtg ctg acc ctg gcc    912
Gly Ile Leu Lys Lys Glu Asp Phe Glu Arg Thr Val Leu Thr Leu Ala
    290                 295                 300 tac aca gcc tac cgc aca gcc ctg tcc cac ggc cat cag aag gac atc    960
Tyr Thr Ala Tyr Arg Thr Ala Leu Ser His Gly His Gln Lys Asp Ile
305                 310                 315                 320 tgg gcg cag tcc ctc gtt agc ctc ttc cag gcc ctg agg cac gac ttg   1008
Trp Ala Gln Ser Leu Val Ser Leu Phe Gln Ala Leu Arg His Asp Leu
                325                 330                 335 atg cgc tcc tca cag ccg gga gta cct ccc ggt tct gga gga cat cac   1056
Met Arg Ser Ser Gln Pro Gly Val Pro Pro Gly Ser Gly Gly His His
            340                 345                 350 cat cac cat cac tga                                                1071
His His His His *
        355

<210> SEQ ID NO 52
<211> LENGTH: 356
<212> TYPE: PRT
<213> ORGANISM: Artificial Sequence
<220> FEATURE:
<223> OTHER INFORMATION: zcyto33F2cHis (S38)

<400> SEQUENCE: 52

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
        35                  40                  45
```

```
Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro Gly Ser Gly
            180                 185                 190

Ser Ser Arg Gly Gly Ser Gly Ser Gly Ser Gly Ala Gly Ser
        195                 200                 205

Lys Leu Ser Ser Ser Leu Pro Leu Asn Pro Val Leu Gln Thr Ser Leu
    210                 215                 220

Glu Glu Val Glu Leu Leu Tyr Glu Phe Leu Leu Ala Glu Leu Glu Ile
225                 230                 235                 240

Ser Pro Asp Leu Gln Ile Ser Ile Lys Asp Glu Leu Ala Ser Leu
                245                 250                 255

Arg Lys Ala Ser Asp Phe Arg Thr Val Cys Asn Asn Val Ile Pro Lys
            260                 265                 270

Ser Ile Pro Asp Ile Arg Arg Leu Ser Ala Ser Leu Ser Ser His Pro
        275                 280                 285

Gly Ile Leu Lys Lys Glu Asp Phe Glu Arg Thr Val Leu Thr Leu Ala
    290                 295                 300

Tyr Thr Ala Tyr Arg Thr Ala Leu Ser His Gly His Gln Lys Asp Ile
305                 310                 315                 320

Trp Ala Gln Ser Leu Val Ser Leu Phe Gln Ala Leu Arg His Asp Leu
                325                 330                 335

Met Arg Ser Ser Gln Pro Gly Val Pro Pro Gly Ser Gly Gly His His
            340                 345                 350

His His His His
        355

<210> SEQ ID NO 53
<211> LENGTH: 1122
<212> TYPE: DNA
<213> ORGANISM: Mus musculus
<220> FEATURE:
<221> NAME/KEY: CDS
<222> LOCATION: (1)...(1122)

<400> SEQUENCE: 53 atg gat gca atg aag aga ggg ctc tgc tgt gtg ctg ctg ctg tgt ggc         48
Met Asp Ala Met Lys Arg Gly Leu Cys Cys Val Leu Leu Leu Cys Gly
 1               5                  10                  15 gcc gtc ttc gtt tcg ctc agc cag gaa atc cat gcc gag ttg aga cgc         96
Ala Val Phe Val Ser Leu Ser Gln Glu Ile His Ala Glu Leu Arg Arg
             20                  25                  30
```

-continued

| | |
|---|---|
| ttc cgt aga tct ttg tca ctg cca ttg aat cca gtc ctg cag acc tcc<br>Phe Arg Arg Ser Leu Ser Leu Pro Leu Asn Pro Val Leu Gln Thr Ser<br>           35                  40                  45 | 144 |
| ctg gag gag gtg gaa ctg ctg tat gag ctc ttg cta gct gaa att gag<br>Leu Glu Glu Val Glu Leu Leu Tyr Glu Leu Leu Leu Ala Glu Ile Glu<br>50                  55                  60 | 192 |
| atc agc cca gac ctg gag atc tcc atc aag gac gag gag cta gct tcc<br>Ile Ser Pro Asp Leu Glu Ile Ser Ile Lys Asp Glu Glu Leu Ala Ser<br>65                  70                75                80 | 240 |
| ctg cgg aag gcc ttg agt ttc cac tca atc tgc aat aac ata atc ccc<br>Leu Arg Lys Ala Leu Ser Phe His Ser Ile Cys Asn Asn Ile Ile Pro<br>                  85                  90                  95 | 288 |
| aag cgt atc cca gat atc cga agg ctg agt gcc aac ctg gca aac cac<br>Lys Arg Ile Pro Asp Ile Arg Arg Leu Ser Ala Asn Leu Ala Asn His<br>                      100                  105              110 | 336 |
| cct gga atc ctc aag aaa gaa gac ttt gag agg ata aca tta acc ctg<br>Pro Gly Ile Leu Lys Lys Glu Asp Phe Glu Arg Ile Thr Leu Thr Leu<br>                  115                  120              125 | 384 |
| gcg tac aca gcc tat cgg aca gcc tta tct gaa ggg cat cag aag gac<br>Ala Tyr Thr Ala Tyr Arg Thr Ala Leu Ser Glu Gly His Gln Lys Asp<br>130                      135                  140 | 432 |
| atc tgg gct cag tcc ctc atc agc cta ttc cag gcc ctg agg cat gac<br>Ile Trp Ala Gln Ser Leu Ile Ser Leu Phe Gln Ala Leu Arg His Asp<br>145                  150                  155              160 | 480 |
| ttg atg cgg tcc tcg agc cct gct gtg tca tcc gga tct ggc agt agt<br>Leu Met Arg Ser Ser Ser Pro Ala Val Ser Ser Gly Ser Gly Ser Ser<br>                  165                  170              175 | 528 |
| aga ggc ggc tct gga agc gga gga agc gga gga gcc gga agt aaa ctg<br>Arg Gly Gly Ser Gly Ser Gly Gly Ser Gly Gly Ala Gly Ser Lys Leu<br>                    180                  185              190 | 576 |
| gtg cct agg agt agc agt cct gac tgg gct cag tgc cag cag ctc tct<br>Val Pro Arg Ser Ser Ser Pro Asp Trp Ala Gln Cys Gln Gln Leu Ser<br>                  195                  200              205 | 624 |
| cgg aat ctc tgc atg cta gcc tgg aac gca cat gca cca gcg gga cat<br>Arg Asn Leu Cys Met Leu Ala Trp Asn Ala His Ala Pro Ala Gly His<br>210                      215                  220 | 672 |
| atg aat cta cta aga gaa gaa gag gat gaa gag act aaa aat aat gtg<br>Met Asn Leu Leu Arg Glu Glu Glu Asp Glu Glu Thr Lys Asn Asn Val<br>225                  230                  235              240 | 720 |
| ccc cgt atc cag tgt gaa gat ggt tgt gac cca caa gga ctc aag gac<br>Pro Arg Ile Gln Cys Glu Asp Gly Cys Asp Pro Gln Gly Leu Lys Asp<br>                      245                  250              255 | 768 |
| aac agc cag ttc tgc ttg caa agg atc cgc caa ggt ctg gct ttt tat<br>Asn Ser Gln Phe Cys Leu Gln Arg Ile Arg Gln Gly Leu Ala Phe Tyr<br>                  260                  265              270 | 816 |
| aag cac ctg ctt gac tct gac atc ttc aaa ggg gag cct gct cta ctc<br>Lys His Leu Leu Asp Ser Asp Ile Phe Lys Gly Glu Pro Ala Leu Leu<br>275                      280                  285 | 864 |
| cct gat agc ccc atg gag caa ctt cac acc tcc cta cta gga ctc agc<br>Pro Asp Ser Pro Met Glu Gln Leu His Thr Ser Leu Leu Gly Leu Ser<br>     290                  295                  300 | 912 |
| caa ctc ctc cag cca gag gat cac ccc cgg gag acc caa cag atg ccc<br>Gln Leu Leu Gln Pro Glu Asp His Pro Arg Glu Thr Gln Gln Met Pro<br>305                  310                  315              320 | 960 |
| agc ctg agt tct agt cag cag tgg cag cgc ccc ctt ctc cgt tcc aag<br>Ser Leu Ser Ser Ser Gln Gln Trp Gln Arg Pro Leu Leu Arg Ser Lys<br>                      325                  330              335 | 1008 |
| atc ctt cga agc ctc cag gcc ttt ttg gcc ata gct gcc cgg gtc ttt<br>Ile Leu Arg Ser Leu Gln Ala Phe Leu Ala Ile Ala Ala Arg Val Phe<br>                  340                  345              350 | 1056 |

```
gcc cac gga gca gca act ctg act gag ccc tta gtg cca aca gct cat    1104
Ala His Gly Ala Ala Thr Leu Thr Glu Pro Leu Val Pro Thr Ala His
    355                 360                 365 cac cat cac cat cac taa                                            1122
His His His His His  *
    370
```

<210> SEQ ID NO 54
<211> LENGTH: 373
<212> TYPE: PRT
<213> ORGANISM: Mus musculus

<400> SEQUENCE: 54

```
Met Asp Ala Met Lys Arg Gly Leu Cys Cys Val Leu Leu Cys Gly
  1               5                  10                  15

Ala Val Phe Val Ser Leu Ser Gln Glu Ile His Ala Glu Leu Arg Arg
                 20                  25                  30

Phe Arg Arg Ser Leu Ser Leu Pro Leu Asn Pro Val Leu Gln Thr Ser
             35                  40                  45

Leu Glu Glu Val Glu Leu Leu Tyr Glu Leu Leu Leu Ala Glu Ile Glu
         50                  55                  60

Ile Ser Pro Asp Leu Glu Ile Ser Ile Lys Asp Glu Glu Leu Ala Ser
 65                  70                  75                  80

Leu Arg Lys Ala Leu Ser Phe His Ser Ile Cys Asn Asn Ile Ile Pro
                 85                  90                  95

Lys Arg Ile Pro Asp Ile Arg Arg Leu Ser Ala Asn Leu Ala Asn His
            100                 105                 110

Pro Gly Ile Leu Lys Lys Glu Asp Phe Glu Arg Ile Thr Leu Thr Leu
            115                 120                 125

Ala Tyr Thr Ala Tyr Arg Thr Ala Leu Ser Glu Gly His Gln Lys Asp
        130                 135                 140

Ile Trp Ala Gln Ser Leu Ile Ser Leu Phe Gln Ala Leu Arg His Asp
145                 150                 155                 160

Leu Met Arg Ser Ser Pro Ala Val Ser Ser Gly Ser Gly Ser Ser
                165                 170                 175

Arg Gly Gly Ser Gly Ser Gly Gly Ser Gly Gly Ala Gly Ser Lys Leu
            180                 185                 190

Val Pro Arg Ser Ser Ser Pro Asp Trp Ala Gln Cys Gln Gln Leu Ser
        195                 200                 205

Arg Asn Leu Cys Met Leu Ala Trp Asn Ala His Ala Pro Ala Gly His
    210                 215                 220

Met Asn Leu Leu Arg Glu Glu Glu Asp Glu Glu Thr Lys Asn Asn Val
225                 230                 235                 240

Pro Arg Ile Gln Cys Glu Asp Gly Cys Asp Pro Gln Gly Leu Lys Asp
                245                 250                 255

Asn Ser Gln Phe Cys Leu Gln Arg Ile Arg Gln Gly Leu Ala Phe Tyr
            260                 265                 270

Lys His Leu Leu Asp Ser Asp Ile Phe Lys Gly Glu Pro Ala Leu Leu
        275                 280                 285

Pro Asp Ser Pro Met Glu Gln Leu His Thr Ser Leu Leu Gly Leu Ser
    290                 295                 300

Gln Leu Leu Gln Pro Glu Asp His Pro Arg Glu Thr Gln Gln Met Pro
305                 310                 315                 320

Ser Leu Ser Ser Ser Gln Gln Trp Gln Arg Pro Leu Leu Arg Ser Lys
                325                 330                 335
```

Ile Leu Arg Ser Leu Gln Ala Phe Leu Ala Ile Ala Ala Arg Val Phe
        340                 345                 350

Ala His Gly Ala Ala Thr Leu Thr Glu Pro Leu Val Pro Thr Ala His
        355                 360                 365

His His His His His
        370

<210> SEQ ID NO 55
<211> LENGTH: 1308
<212> TYPE: DNA
<213> ORGANISM: Artificial Sequence
<220> FEATURE:
<223> OTHER INFORMATION: zcyto35f2cHis (W23)
<220> FEATURE:
<221> NAME/KEY: CDS
<222> LOCATION: (1)...(1308)

<400> SEQUENCE: 55

| | | |
|---|---|---|
| atg tgg ccc cct ggg tca gcc tcc cag cca ccg ccc tca cct gcc gcg<br>Met Trp Pro Pro Gly Ser Ala Ser Gln Pro Pro Ser Pro Ala Ala<br>1               5                   10                  15 | | 48 |
| gcc aca ggt ctg cat cca gcg gct cgc cct gtg tcc ctg cag tgc cgg<br>Ala Thr Gly Leu His Pro Ala Ala Arg Pro Val Ser Leu Gln Cys Arg<br>        20                  25                  30 | | 96 |
| ctc agc atg tgt cca gcg cgc agc ctc ctc ctt gtg gct acc ctg gtc<br>Leu Ser Met Cys Pro Ala Arg Ser Leu Leu Leu Val Ala Thr Leu Val<br>        35                  40                  45 | | 144 |
| ctc ctg gac cac ctc agt ttg gcc aga aac ctc ccc gtg gcc act cca<br>Leu Leu Asp His Leu Ser Leu Ala Arg Asn Leu Pro Val Ala Thr Pro<br>50                  55                  60 | | 192 |
| gac cca gga atg ttc cca tgc ctt cac cac tcc caa aac ctg ctg agg<br>Asp Pro Gly Met Phe Pro Cys Leu His His Ser Gln Asn Leu Leu Arg<br>65                  70                  75                  80 | | 240 |
| gcc gtc agc aac atg ctc cag aag gcc aga caa act cta gaa ttt tac<br>Ala Val Ser Asn Met Leu Gln Lys Ala Arg Gln Thr Leu Glu Phe Tyr<br>        85                  90                  95 | | 288 |
| cct tgc act tct gaa gag att gat cat gaa gat atc aca aaa gat aaa<br>Pro Cys Thr Ser Glu Glu Ile Asp His Glu Asp Ile Thr Lys Asp Lys<br>        100                 105                 110 | | 336 |
| acc agc aca gtg gag gcc tgt tta cca ttg gaa tta acc aag aat gag<br>Thr Ser Thr Val Glu Ala Cys Leu Pro Leu Glu Leu Thr Lys Asn Glu<br>        115                 120                 125 | | 384 |
| agt tgc cta aat tcc aga gag acc tct ttc ata act aat ggg agt tgc<br>Ser Cys Leu Asn Ser Arg Glu Thr Ser Phe Ile Thr Asn Gly Ser Cys<br>130                 135                 140 | | 432 |
| ctg gcc tcc aga aag acc tct ttt atg atg gcc ctg tgc ctt agt agt<br>Leu Ala Ser Arg Lys Thr Ser Phe Met Met Ala Leu Cys Leu Ser Ser<br>145                 150                 155                 160 | | 480 |
| att tat gaa gac ttg aag atg tac cag gtg gag ttc aag acc atg aat<br>Ile Tyr Glu Asp Leu Lys Met Tyr Gln Val Glu Phe Lys Thr Met Asn<br>        165                 170                 175 | | 528 |
| gca aag ctt ctg atg gat cct aag agg cag atc ttt cta gat caa aac<br>Ala Lys Leu Leu Met Asp Pro Lys Arg Gln Ile Phe Leu Asp Gln Asn<br>        180                 185                 190 | | 576 |
| atg ctg gca gtt att gat gag ctg atg cag gcc ctg aat ttc aac agt<br>Met Leu Ala Val Ile Asp Glu Leu Met Gln Ala Leu Asn Phe Asn Ser<br>        195                 200                 205 | | 624 |
| gag act gtg cca caa aaa tcc tcc ctt gaa gaa ccg gat ttt tat aaa<br>Glu Thr Val Pro Gln Lys Ser Ser Leu Glu Glu Pro Asp Phe Tyr Lys<br>        210                 215                 220 | | 672 |

```
act aaa atc aag ctc tgc ata ctt ctt cat gct ttc aga att cgg gca      720
Thr Lys Ile Lys Leu Cys Ile Leu Leu His Ala Phe Arg Ile Arg Ala
225                 230                 235                 240 gtg act att gat aga gtg atg agc tat ctg aat gct tcc gga tct ggc      768
Val Thr Ile Asp Arg Val Met Ser Tyr Leu Asn Ala Ser Gly Ser Gly
                245                 250                 255 agt agt aga ggc ggc tct gga agc gga gga agc gga gga gcc gga agt      816
Ser Ser Arg Gly Gly Ser Gly Ser Gly Gly Ser Gly Gly Ala Gly Ser
            260                 265                 270 aaa ctg tgg agc agg gct gtg ctc ttc cct gcc gcc cac cgg cca aag      864
Lys Leu Trp Ser Arg Ala Val Leu Phe Pro Ala Ala His Arg Pro Lys
        275                 280                 285 agg tcc tca tca ctg cca ttg aac cca gtc ctg cag acc tcc ctg gag      912
Arg Ser Ser Ser Leu Pro Leu Asn Pro Val Leu Gln Thr Ser Leu Glu
    290                 295                 300 gag gtg gag ctg ctc tac gag ttc ctg ctg gcc gaa ctt gag atc agc      960
Glu Val Glu Leu Leu Tyr Glu Phe Leu Leu Ala Glu Leu Glu Ile Ser
305                 310                 315                 320 cct gac ctg cag atc tcc atc aag gac gag gag ctg gcc tcc ttg cgg     1008
Pro Asp Leu Gln Ile Ser Ile Lys Asp Glu Glu Leu Ala Ser Leu Arg
                325                 330                 335 aag gcc tca gac ttc cgc acc gtc tgc aac aac gtc atc ccc aag agc     1056
Lys Ala Ser Asp Phe Arg Thr Val Cys Asn Asn Val Ile Pro Lys Ser
            340                 345                 350 atc cca gac atc cgc cgg ctc agc gcc agc ctc tcc agc cac cct ggc     1104
Ile Pro Asp Ile Arg Arg Leu Ser Ala Ser Leu Ser Ser His Pro Gly
        355                 360                 365 atc ctc aag aaa gaa gac ttt gaa agg aca gtg ctg acc ctg gcc tac     1152
Ile Leu Lys Lys Glu Asp Phe Glu Arg Thr Val Leu Thr Leu Ala Tyr
    370                 375                 380 aca gcc tac cgc aca gcc ctg tcc cac ggc cat cag aag gac atc tgg     1200
Thr Ala Tyr Arg Thr Ala Leu Ser His Gly His Gln Lys Asp Ile Trp
385                 390                 395                 400 gcg cag tcc ctc gtt agc ctc ttc cag gcc ctg agg cac gac ttg atg     1248
Ala Gln Ser Leu Val Ser Leu Phe Gln Ala Leu Arg His Asp Leu Met
                405                 410                 415 cgc tcc tca cag ccg gga gta cct ccc gga tcc ggt gga cat cac cat     1296
Arg Ser Ser Gln Pro Gly Val Pro Pro Gly Ser Gly Gly His His His
            420                 425                 430 cac cat cac taa                                                     1308
His His His *
        435

<210> SEQ ID NO 56
<211> LENGTH: 435
<212> TYPE: PRT
<213> ORGANISM: Artificial Sequence
<220> FEATURE:
<223> OTHER INFORMATION: zcyto35f2cHis (W23)

<400> SEQUENCE: 56

Met Trp Pro Pro Gly Ser Ala Ser Gln Pro Pro Ser Pro Ala Ala
 1               5                  10                  15

Ala Thr Gly Leu His Pro Ala Ala Pro Val Ser Leu Gln Cys Arg
                20                  25                  30

Leu Ser Met Cys Pro Ala Arg Ser Leu Leu Val Ala Thr Leu Val
            35                  40                  45

Leu Leu Asp His Leu Ser Leu Ala Arg Asn Leu Pro Val Ala Thr Pro
        50                  55                  60

Asp Pro Gly Met Phe Pro Cys Leu His His Ser Gln Asn Leu Leu Arg
```

65                  70                  75                  80
Ala Val Ser Asn Met Leu Gln Lys Ala Arg Gln Thr Leu Glu Phe Tyr
                        85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser Gly Ser Gly
                245                 250                 255

Ser Ser Arg Gly Gly Ser Gly Ser Gly Gly Ser Gly Gly Ala Gly Ser
            260                 265                 270

Lys Leu Trp Ser Arg Ala Val Leu Phe Pro Ala Ala His Arg Pro Lys
        275                 280                 285

Arg Ser Ser Ser Leu Pro Leu Asn Pro Val Leu Gln Thr Ser Leu Glu
    290                 295                 300

Glu Val Glu Leu Leu Tyr Glu Phe Leu Leu Ala Glu Leu Glu Ile Ser
305                 310                 315                 320

Pro Asp Leu Gln Ile Ser Ile Lys Asp Glu Glu Leu Ala Ser Leu Arg
                325                 330                 335

Lys Ala Ser Asp Phe Arg Thr Val Cys Asn Asn Val Ile Pro Lys Ser
            340                 345                 350

Ile Pro Asp Ile Arg Arg Leu Ser Ala Ser Leu Ser Ser His Pro Gly
        355                 360                 365

Ile Leu Lys Lys Glu Asp Phe Glu Arg Thr Val Leu Thr Leu Ala Tyr
    370                 375                 380

Thr Ala Tyr Arg Thr Ala Leu Ser His Gly His Gln Lys Asp Ile Trp
385                 390                 395                 400

Ala Gln Ser Leu Val Ser Leu Phe Gln Ala Leu Arg His Asp Leu Met
                405                 410                 415

Arg Ser Ser Gln Pro Gly Val Pro Pro Gly Ser Gly Gly His His
            420                 425                 430

His His His
        435

<210> SEQ ID NO 57
<211> LENGTH: 1263
<212> TYPE: DNA
<213> ORGANISM: Artificial Sequence
<220> FEATURE:
<223> OTHER INFORMATION: zcyto35f2cHis (S38)
<220> FEATURE:

```
<221> NAME/KEY: CDS
<222> LOCATION: (1)...(1263)

<400> SEQUENCE: 57 atg tgg ccc cct ggg tca gcc tcc cag cca ccg ccc tca cct gcc gcg        48
Met Trp Pro Pro Gly Ser Ala Ser Gln Pro Pro Pro Ser Pro Ala Ala
 1               5                  10                  15 gcc aca ggt ctg cat cca gcg gct cgc cct gtg tcc ctg cag tgc cgg        96
Ala Thr Gly Leu His Pro Ala Ala Arg Pro Val Ser Leu Gln Cys Arg
             20                  25                  30 ctc agc atg tgt cca gcg cgc agc ctc ctc ctt gtg gct acc ctg gtc       144
Leu Ser Met Cys Pro Ala Arg Ser Leu Leu Leu Val Ala Thr Leu Val
         35                  40                  45 ctc ctg gac cac ctc agt ttg gcc aga aac ctc ccc gtg gcc act cca       192
Leu Leu Asp His Leu Ser Leu Ala Arg Asn Leu Pro Val Ala Thr Pro
     50                  55                  60 gac cca gga atg ttc cca tgc ctt cac cac tcc caa aac ctg ctg agg       240
Asp Pro Gly Met Phe Pro Cys Leu His His Ser Gln Asn Leu Leu Arg
 65                  70                  75                  80 gcc gtc agc aac atg ctc cag aag gcc aga caa act cta gaa ttt tac       288
Ala Val Ser Asn Met Leu Gln Lys Ala Arg Gln Thr Leu Glu Phe Tyr
                 85                  90                  95 cct tgc act tct gaa gag att gat cat gaa gat atc aca aaa gat aaa       336
Pro Cys Thr Ser Glu Glu Ile Asp His Glu Asp Ile Thr Lys Asp Lys
            100                 105                 110 acc agc aca gtg gag gcc tgt tta cca ttg gaa tta acc aag aat gag       384
Thr Ser Thr Val Glu Ala Cys Leu Pro Leu Glu Leu Thr Lys Asn Glu
        115                 120                 125 agt tgc cta aat tcc aga gag acc tct ttc ata act aat ggg agt tgc       432
Ser Cys Leu Asn Ser Arg Glu Thr Ser Phe Ile Thr Asn Gly Ser Cys
    130                 135                 140 ctg gcc tcc aga aag acc tct ttt atg atg gcc ctg tgc ctt agt agt       480
Leu Ala Ser Arg Lys Thr Ser Phe Met Met Ala Leu Cys Leu Ser Ser
145                 150                 155                 160 att tat gaa gac ttg aag atg tac cag gtg gag ttc aag acc atg aat       528
Ile Tyr Glu Asp Leu Lys Met Tyr Gln Val Glu Phe Lys Thr Met Asn
                165                 170                 175 gca aag ctt ctg atg gat cct aag agg cag atc ttt cta gat caa aac       576
Ala Lys Leu Leu Met Asp Pro Lys Arg Gln Ile Phe Leu Asp Gln Asn
            180                 185                 190 atg ctg gca gtt att gat gag ctg atg cag gcc ctg aat ttc aac agt       624
Met Leu Ala Val Ile Asp Glu Leu Met Gln Ala Leu Asn Phe Asn Ser
        195                 200                 205 gag act gtg cca caa aaa tcc tcc ctt gaa gaa ccg gat ttt tat aaa       672
Glu Thr Val Pro Gln Lys Ser Ser Leu Glu Glu Pro Asp Phe Tyr Lys
    210                 215                 220 act aaa atc aag ctc tgc ata ctt ctt cat gct ttc aga att cgg gca       720
Thr Lys Ile Lys Leu Cys Ile Leu Leu His Ala Phe Arg Ile Arg Ala
225                 230                 235                 240 gtg act att gat aga gtg atg agc tat ctg aat gct tcc gga tct ggc       768
Val Thr Ile Asp Arg Val Met Ser Tyr Leu Asn Ala Ser Gly Ser Gly
                245                 250                 255 agt agt aga ggc ggc tct gga agc gga gga agc gga gga gcc gga agt       816
Ser Ser Arg Gly Gly Ser Gly Ser Gly Gly Ser Gly Gly Ala Gly Ser
            260                 265                 270 aaa ctg tcc tca tca ctg cca ttg aac cca gtc ctg cag acc tcc ctg       864
Lys Leu Ser Ser Ser Leu Pro Leu Asn Pro Val Leu Gln Thr Ser Leu
        275                 280                 285 gag gag gtg gag ctg ctc tac gag ttc ctg ctg gcc gaa ctt gag atc       912
Glu Glu Val Glu Leu Leu Tyr Glu Phe Leu Leu Ala Glu Leu Glu Ile
```

```
                    290                 295                 300
agc cct gac ctg cag atc tcc atc aag gac gag gag ctg gcc tcc ttg         960
Ser Pro Asp Leu Gln Ile Ser Ile Lys Asp Glu Glu Leu Ala Ser Leu
305                 310                 315                 320 cgg aag gcc tca gac ttc cgc acc gtc tgc aac aac gtc atc ccc aag        1008
Arg Lys Ala Ser Asp Phe Arg Thr Val Cys Asn Asn Val Ile Pro Lys
                325                 330                 335 agc atc cca gac atc cgc cgg ctc agc gcc agc ctc tcc agc cac cct        1056
Ser Ile Pro Asp Ile Arg Arg Leu Ser Ala Ser Leu Ser Ser His Pro
            340                 345                 350 ggc atc ctc aag aaa gaa gac ttt gaa agg aca gtg ctg acc ctg gcc        1104
Gly Ile Leu Lys Lys Glu Asp Phe Glu Arg Thr Val Leu Thr Leu Ala
        355                 360                 365 tac aca gcc tac cgc aca gcc ctg tcc cac ggc cat cag aag gac atc        1152
Tyr Thr Ala Tyr Arg Thr Ala Leu Ser His Gly His Gln Lys Asp Ile
370                 375                 380 tgg gcg cag tcc ctc gtt agc ctc ttc cag gcc ctg agg cac gac ttg        1200
Trp Ala Gln Ser Leu Val Ser Leu Phe Gln Ala Leu Arg His Asp Leu
385                 390                 395                 400 atg cgc tcc tca cag ccg gga gta cct ccc gga tcc ggt gga cat cac        1248
Met Arg Ser Ser Gln Pro Gly Val Pro Pro Gly Ser Gly Gly His His
                405                 410                 415 cat cac cat cac tga                                                    1263
His His His His *
            420

<210> SEQ ID NO 58
<211> LENGTH: 420
<212> TYPE: PRT
<213> ORGANISM: Artificial Sequence
<220> FEATURE:
<223> OTHER INFORMATION: zcyto35f2cHis (S38)

<400> SEQUENCE: 58

Met Trp Pro Pro Gly Ser Ala Ser Gln Pro Pro Ser Pro Ala Ala
 1               5                  10                  15

Ala Thr Gly Leu His Pro Ala Ala Arg Pro Val Ser Leu Gln Cys Arg
                20                  25                  30

Leu Ser Met Cys Pro Ala Arg Ser Leu Leu Val Ala Thr Leu Val
            35                  40                  45

Leu Leu Asp His Leu Ser Leu Ala Arg Asn Leu Pro Val Ala Thr Pro
50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
                100                 105                 110

Thr Ser Thr Val Glu Ala Cys Leu Pro Leu Glu Leu Thr Lys Asn Glu
            115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190
```

```
Met Leu Ala Val Ile Asp Glu Leu Met Gln Ala Leu Asn Phe Asn Ser
            195                 200                 205

Glu Thr Val Pro Gln Lys Ser Ser Leu Glu Glu Pro Asp Phe Tyr Lys
            210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser Gly Ser Gly
            245                 250                 255

Ser Ser Arg Gly Gly Ser Gly Gly Ser Gly Gly Ala Gly Ser
            260                 265                 270

Lys Leu Ser Ser Ser Leu Pro Leu Asn Pro Val Leu Gln Thr Ser Leu
            275                 280                 285

Glu Glu Val Glu Leu Leu Tyr Glu Phe Leu Leu Ala Glu Leu Glu Ile
            290                 295                 300

Ser Pro Asp Leu Gln Ile Ser Ile Lys Asp Glu Glu Leu Ala Ser Leu
305                 310                 315                 320

Arg Lys Ala Ser Asp Phe Arg Thr Val Cys Asn Asn Val Ile Pro Lys
            325                 330                 335

Ser Ile Pro Asp Ile Arg Arg Leu Ser Ala Ser Leu Ser Ser His Pro
            340                 345                 350

Gly Ile Leu Lys Lys Glu Asp Phe Glu Arg Thr Val Leu Thr Leu Ala
            355                 360                 365

Tyr Thr Ala Tyr Arg Thr Ala Leu Ser His Gly His Gln Lys Asp Ile
            370                 375                 380

Trp Ala Gln Ser Leu Val Ser Leu Phe Gln Ala Leu Arg His Asp Leu
385                 390                 395                 400

Met Arg Ser Ser Gln Pro Gly Val Pro Pro Gly Ser Gly Gly His His
            405                 410                 415

His His His His
        420

<210> SEQ ID NO 59
<211> LENGTH: 1197
<212> TYPE: DNA
<213> ORGANISM: Mus musculus
<220> FEATURE:
<221> NAME/KEY: CDS
<222> LOCATION: (1)...(1197)

<400> SEQUENCE: 59 atg tgt caa tca cgc tac ctc ctc ttt ttg gcc acc ctt gcc ctc cta         48
Met Cys Gln Ser Arg Tyr Leu Leu Phe Leu Ala Thr Leu Ala Leu Leu
1               5                   10                  15 aac cac ctc agt ttg gcc agg gtc att cca gtc tct gga cct gcc agg         96
Asn His Leu Ser Leu Ala Arg Val Ile Pro Val Ser Gly Pro Ala Arg
            20                  25                  30 tgt ctt agc cag tcc cga aac ctg ctg aag acc aca gat gac atg gtg        144
Cys Leu Ser Gln Ser Arg Asn Leu Leu Lys Thr Thr Asp Asp Met Val
        35                  40                  45 aag acg gcc aga gaa aaa ctg aaa cat tat tcc tgc act gct gaa gac        192
Lys Thr Ala Arg Glu Lys Leu Lys His Tyr Ser Cys Thr Ala Glu Asp
    50                  55                  60 atc gat cat gaa gac atc aca cgg gac caa acc agc aca ttg aag acc        240
Ile Asp His Glu Asp Ile Thr Arg Asp Gln Thr Ser Thr Leu Lys Thr
65                  70                  75                  80 tgt tta cca ctg gaa cta cac aag aac gag agt tgc ctg gct act aga        288
Cys Leu Pro Leu Glu Leu His Lys Asn Glu Ser Cys Leu Ala Thr Arg
```

-continued

| | | | | | | | | | | | | |
|---|---|---|---|---|---|---|---|---|---|---|---|---|
| | | 85 | | | | 90 | | | | 95 | | |
| gag | act | tct | tcc | aca | aca | aga | ggg | agc | tgc | ctg | ccc | cca cag aag acg | 336 |
| Glu | Thr | Ser | Ser | Thr | Thr | Arg | Gly | Ser | Cys | Leu | Pro | Pro Gln Lys Thr |
| | | | 100 | | | | | 105 | | | | 110 |

| tct | ttg | atg | atg | acc | ctg | tgc | ctt | ggt | agc | atc | tat | gag gac ttg aag | 384 |
|---|---|---|---|---|---|---|---|---|---|---|---|---|---|
| Ser | Leu | Met | Met | Thr | Leu | Cys | Leu | Gly | Ser | Ile | Tyr | Glu Asp Leu Lys |
| | | | | 115 | | | | | 120 | | | 125 |

| atg | tac | cag | aca | gag | ttc | cag | gcc | atc | aac | gca | gca | ctt cag aat cac | 432 |
|---|---|---|---|---|---|---|---|---|---|---|---|---|---|
| Met | Tyr | Gln | Thr | Glu | Phe | Gln | Ala | Ile | Asn | Ala | Ala | Leu Gln Asn His |
| | 130 | | | | | 135 | | | | | 140 | |

| aac | cat | cag | cag | atc | att | cta | gac | aag | ggc | atg | ctg | gtg gcc atc gat | 480 |
|---|---|---|---|---|---|---|---|---|---|---|---|---|---|
| Asn | His | Gln | Gln | Ile | Ile | Leu | Asp | Lys | Gly | Met | Leu | Val Ala Ile Asp |
| 145 | | | | | 150 | | | | | 155 | | | 160 |

| gag | ctg | atg | cag | tct | ctg | aat | cat | aat | ggc | gag | act | ctg cgc cag aaa | 528 |
|---|---|---|---|---|---|---|---|---|---|---|---|---|---|
| Glu | Leu | Met | Gln | Ser | Leu | Asn | His | Asn | Gly | Glu | Thr | Leu Arg Gln Lys |
| | | | | 165 | | | | | 170 | | | | 175 |

| cct | cct | gtg | gga | gaa | gca | gac | cct | tac | aga | gtg | aaa | atg aag ctc tgc | 576 |
|---|---|---|---|---|---|---|---|---|---|---|---|---|---|
| Pro | Pro | Val | Gly | Glu | Ala | Asp | Pro | Tyr | Arg | Val | Lys | Met Lys Leu Cys |
| | | | 180 | | | | | 185 | | | | 190 |

| atc | ctg | ctt | cac | gcc | ttc | agc | acc | cgc | gtc | gtg | acc | atc aac agg gtg | 624 |
|---|---|---|---|---|---|---|---|---|---|---|---|---|---|
| Ile | Leu | Leu | His | Ala | Phe | Ser | Thr | Arg | Val | Val | Thr | Ile Asn Arg Val |
| | | | | 195 | | | | | 200 | | | 205 |

| atg | ggc | tat | ctg | agc | tcc | gcc | gga | tct | ggc | agt | agt | aga ggc ggc tct | 672 |
|---|---|---|---|---|---|---|---|---|---|---|---|---|---|
| Met | Gly | Tyr | Leu | Ser | Ser | Ala | Gly | Ser | Gly | Ser | Ser | Arg Gly Gly Ser |
| | 210 | | | | | 215 | | | | | 220 | |

| gga | agc | gga | gga | agc | gga | gga | gcc | gga | agt | aaa | ctg | agg tgg agc agg | 720 |
|---|---|---|---|---|---|---|---|---|---|---|---|---|---|
| Gly | Ser | Gly | Gly | Ser | Gly | Gly | Ala | Gly | Ser | Lys | Leu | Arg Trp Ser Arg |
| 225 | | | | | 230 | | | | | 235 | | | 240 |

| gcc | gca | ctg | ttc | cca | gct | gcc | cat | cgg | cca | aag | agg | tcc ttg tca ctg | 768 |
|---|---|---|---|---|---|---|---|---|---|---|---|---|---|
| Ala | Ala | Leu | Phe | Pro | Ala | Ala | His | Arg | Pro | Lys | Arg | Ser Leu Ser Leu |
| | | | | 245 | | | | | 250 | | | | 255 |

| cca | ttg | aat | cca | gtc | ctg | cag | acc | tcc | ctg | gag | gag | gtg gaa ctg ctg | 816 |
|---|---|---|---|---|---|---|---|---|---|---|---|---|---|
| Pro | Leu | Asn | Pro | Val | Leu | Gln | Thr | Ser | Leu | Glu | Glu | Val Glu Leu Leu |
| | | | 260 | | | | | 265 | | | | 270 |

| tat | gag | ctc | ttg | cta | gct | gaa | att | gag | atc | agc | cca | gac ctg gag atc | 864 |
|---|---|---|---|---|---|---|---|---|---|---|---|---|---|
| Tyr | Glu | Leu | Leu | Leu | Ala | Glu | Ile | Glu | Ile | Ser | Pro | Asp Leu Glu Ile |
| | | 275 | | | | | 280 | | | | | 285 |

| tcc | atc | aag | gac | gag | gag | cta | gct | tcc | ctg | cgg | aag | gcc ttg agt ttc | 912 |
|---|---|---|---|---|---|---|---|---|---|---|---|---|---|
| Ser | Ile | Lys | Asp | Glu | Glu | Leu | Ala | Ser | Leu | Arg | Lys | Ala Leu Ser Phe |
| 290 | | | | | 295 | | | | | 300 | | | |

| cac | tca | atc | tgc | aat | aac | ata | atc | ccc | aag | cgt | atc | cca gat atc cga | 960 |
|---|---|---|---|---|---|---|---|---|---|---|---|---|---|
| His | Ser | Ile | Cys | Asn | Asn | Ile | Ile | Pro | Lys | Arg | Ile | Pro Asp Ile Arg |
| 305 | | | | | 310 | | | | | 315 | | | 320 |

| agg | ctg | agt | gcc | aac | ctg | gca | aac | cac | cct | gga | atc | ctc aag aaa gaa | 1008 |
|---|---|---|---|---|---|---|---|---|---|---|---|---|---|
| Arg | Leu | Ser | Ala | Asn | Leu | Ala | Asn | His | Pro | Gly | Ile | Leu Lys Lys Glu |
| | | | | 325 | | | | | 330 | | | | 335 |

| gac | ttt | gag | agg | ata | aca | tta | acc | ctg | gcg | tac | aca | gcc tat cgg aca | 1056 |
|---|---|---|---|---|---|---|---|---|---|---|---|---|---|
| Asp | Phe | Glu | Arg | Ile | Thr | Leu | Thr | Leu | Ala | Tyr | Thr | Ala Tyr Arg Thr |
| | | | 340 | | | | | 345 | | | | 350 |

| gcc | tta | tct | gaa | ggg | cat | cag | aag | gac | atc | tgg | gct | cag tcc ctc atc | 1104 |
|---|---|---|---|---|---|---|---|---|---|---|---|---|---|
| Ala | Leu | Ser | Glu | Gly | His | Gln | Lys | Asp | Ile | Trp | Ala | Gln Ser Leu Ile |
| | | 355 | | | | | 360 | | | | | 365 |

| agc | cta | ttc | cag | gcc | ctg | agg | cat | gac | ttg | atg | cgg | tcc tcg agc cct | 1152 |
|---|---|---|---|---|---|---|---|---|---|---|---|---|---|
| Ser | Leu | Phe | Gln | Ala | Leu | Arg | His | Asp | Leu | Met | Arg | Ser Ser Ser Pro |
| 370 | | | | | 375 | | | | | 380 | | | |

| gct | gtg | tca | tcc | gga | tct | ggt | gga | cat | cac | cat | cac | cat cac taa | 1197 |
|---|---|---|---|---|---|---|---|---|---|---|---|---|---|
| Ala | Val | Ser | Ser | Gly | Ser | Gly | Gly | His | His | His | His | His His * |
| 385 | | | | | 390 | | | | | 395 | | | |

```
<210> SEQ ID NO 60
<211> LENGTH: 398
<212> TYPE: PRT
<213> ORGANISM: Mus musculus

<400> SEQUENCE: 60

Met Cys Gln Ser Arg Tyr Leu Leu Phe Leu Ala Thr Leu Ala Leu Leu
  1               5                  10                  15

Asn His Leu Ser Leu Ala Arg Val Ile Pro Val Ser Gly Pro Ala Arg
                 20                  25                  30

Cys Leu Ser Gln Ser Arg Asn Leu Leu Lys Thr Thr Asp Asp Met Val
             35                  40                  45

Lys Thr Ala Arg Glu Lys Leu Lys His Tyr Ser Cys Thr Ala Glu Asp
 50                  55                  60

Ile Asp His Glu Asp Ile Thr Arg Asp Gln Thr Ser Thr Leu Lys Thr
 65                  70                  75                  80

Cys Leu Pro Leu Glu Leu His Lys Asn Glu Ser Cys Leu Ala Thr Arg
                 85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
            115                 120                 125

Met Tyr Gln Thr Glu Phe Gln Ala Ile Asn Ala Ala Leu Gln Asn His
130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
            195                 200                 205

Met Gly Tyr Leu Ser Ser Ala Gly Ser Gly Ser Ser Arg Gly Gly Ser
210                 215                 220

Gly Ser Gly Gly Ser Gly Gly Ala Gly Ser Lys Leu Arg Trp Ser Arg
225                 230                 235                 240

Ala Ala Leu Phe Pro Ala Ala His Arg Pro Lys Arg Ser Leu Ser Leu
                245                 250                 255

Pro Leu Asn Pro Val Leu Gln Thr Ser Leu Glu Glu Val Glu Leu Leu
            260                 265                 270

Tyr Glu Leu Leu Leu Ala Glu Ile Glu Ile Ser Pro Asp Leu Glu Ile
            275                 280                 285

Ser Ile Lys Asp Glu Glu Leu Ala Ser Leu Arg Lys Ala Leu Ser Phe
290                 295                 300

His Ser Ile Cys Asn Asn Ile Ile Pro Lys Arg Ile Pro Asp Ile Arg
305                 310                 315                 320

Arg Leu Ser Ala Asn Leu Ala Asn His Pro Gly Ile Leu Lys Lys Glu
                325                 330                 335

Asp Phe Glu Arg Ile Thr Leu Thr Leu Ala Tyr Thr Ala Tyr Arg Thr
            340                 345                 350

Ala Leu Ser Glu Gly His Gln Lys Asp Ile Trp Ala Gln Ser Leu Ile
            355                 360                 365

Ser Leu Phe Gln Ala Leu Arg His Asp Leu Met Arg Ser Ser Ser Pro
370                 375                 380
```

```
Ala Val Ser Ser Gly Ser Gly His His His His His
385                 390             395

<210> SEQ ID NO 61
<211> LENGTH: 1498
<212> TYPE: DNA
<213> ORGANISM: Mus musculus
<220> FEATURE:
<221> NAME/KEY: CDS
<222> LOCATION: (197)...(718)

<400> SEQUENCE: 61
gagaggtacc aacttctgtc ccacccaaga ggctgcatcc gcctccatcc tgtggagcca      60
gggagaggcc cttgctttcc ttatagacaa gaaagggcag taagaactct gtcctctcgc     120
tgagaagagc aggggtccac ctgcagcccc tggggtcccg caggaataga aggtcagctt     180
gtctccctcc tggaag atg tcc tgg aag gcg ctg acg att ctg ctg gta ttc    232
               Met Ser Trp Lys Ala Leu Thr Ile Leu Leu Val Phe
                 1               5                  10 tcc agc acc cag gcc act gcg tcc tgc agg tgg agc agg gcc gca ctg       280
Ser Ser Thr Gln Ala Thr Ala Ser Cys Arg Trp Ser Arg Ala Ala Leu
             15                  20                  25 ttc cca gct gcc cat cgg cca aag agg tcc ttg tca ctg cca ttg aat       328
Phe Pro Ala Ala His Arg Pro Lys Arg Ser Leu Ser Leu Pro Leu Asn
         30                  35                  40 cca gtc ctg cag acc tcc ctg gag gag gtg gaa ctg ctg tat gag ctc       376
Pro Val Leu Gln Thr Ser Leu Glu Glu Val Glu Leu Leu Tyr Glu Leu
 45                  50                  55                  60 ttg cta gct gaa att gag atc agc cca gac ctg gag atc tcc atc aag       424
Leu Leu Ala Glu Ile Glu Ile Ser Pro Asp Leu Glu Ile Ser Ile Lys
                 65                  70                  75 gac gag gag cta gct tcc ctg cgg aag gcc ttg agt ttc cac tca atc       472
Asp Glu Glu Leu Ala Ser Leu Arg Lys Ala Leu Ser Phe His Ser Ile
             80                  85                  90 tgc aat aac ata atc ccc aag cgt atc cca gat atc cga agg ctg agt       520
Cys Asn Asn Ile Ile Pro Lys Arg Ile Pro Asp Ile Arg Arg Leu Ser
         95                  100                 105 gcc aac ctg gca aac cac cct gga atc ctc aag aaa gaa gac ttt gag       568
Ala Asn Leu Ala Asn His Pro Gly Ile Leu Lys Lys Glu Asp Phe Glu
 110                 115                 120 agg ata aca tta acc ctg gcg tac aca gcc tat cgg aca gcc tta tct       616
Arg Ile Thr Leu Thr Leu Ala Tyr Thr Ala Tyr Arg Thr Ala Leu Ser
125                 130                 135                 140 gaa ggg cat cag aag gac atc tgg gct cag tcc ctc atc agc cta ttc       664
Glu Gly His Gln Lys Asp Ile Trp Ala Gln Ser Leu Ile Ser Leu Phe
                 145                 150                 155 cag gcc ctg agg cat gac ttg atg cgg tcc tcg agc cct gct gtg tca       712
Gln Ala Leu Arg His Asp Leu Met Arg Ser Ser Ser Pro Ala Val Ser
             160                 165                 170 tcc tga gagaatggct catgctagaa ctttgaagca ggaacaggca cacacagtct        768
Ser * tctagaactt tcatcctcta ctgcactttc agagaaaagt atatacttcc cacacagaat     828
agcaaagata aatgagtcac cccaatattt tttgtccctt gttgcttcca gacagacata     888
tccgacctat gttataatgt tacctgagaa aaggctagac tggactttca agatgcctcc     948
agaggccaac tggtctacct ggtaatgagc agacttctga gatatactta cacacatacc    1008
caagagtagg gactgaggat ggagtctgag catggcagga ggatggtggg cagattcctt    1068
tggttctaag ggatctgtgt tgaatgaata ttttctggca ggttctatgg taaatataaa    1128
```

```
aaaggcagag atgcattcaa attaatatgc tattagccaa gaaggatata cttggcttgc    1188
cccaaagcca tgaagaagac tctgtatttt ggtgacctac ttgacttggt ggaaatgcta    1248
gcagtccacc catgccctat catttcaatg tagaagccag gctaaagcat agtgccttcc    1308
taatgaaaga ggtaacacca ctatgcgtgt ttttcctaaa ataccatagc actgtcagcg    1368
acttgggtgc tcctaaaaaa attcgctttc agatgacaga ttgtttacct ttcaaatgct    1428 gattttttt ctttcaaaat gttagtttga tatctgttca ttatttatat taaatactgg    1488
ttgatattta                                                           1498
```

<210> SEQ ID NO 62
<211> LENGTH: 173
<212> TYPE: PRT
<213> ORGANISM: Mus musculus

<400> SEQUENCE: 62

```
Met Ser Trp Lys Ala Leu Thr Ile Leu Leu Val Phe Ser Ser Thr Gln
 1               5                  10                  15

Ala Thr Ala Ser Cys Arg Trp Ser Arg Ala Ala Leu Phe Pro Ala Ala
             20                  25                  30

His Arg Pro Lys Arg Ser Leu Ser Leu Pro Leu Asn Pro Val Leu Gln
         35                  40                  45

Thr Ser Leu Glu Glu Val Glu Leu Leu Tyr Glu Leu Leu Leu Ala Glu
     50                  55                  60

Ile Glu Ile Ser Pro Asp Leu Glu Ile Ser Ile Lys Asp Glu Glu Leu
 65                  70                  75                  80

Ala Ser Leu Arg Lys Ala Leu Ser Phe His Ser Ile Cys Asn Asn Ile
                 85                  90                  95

Ile Pro Lys Arg Ile Pro Asp Ile Arg Arg Leu Ser Ala Asn Leu Ala
            100                 105                 110

Asn His Pro Gly Ile Leu Lys Lys Glu Asp Phe Glu Arg Ile Thr Leu
        115                 120                 125

Thr Leu Ala Tyr Thr Ala Tyr Arg Thr Ala Leu Ser Glu Gly His Gln
    130                 135                 140

Lys Asp Ile Trp Ala Gln Ser Leu Ile Ser Leu Phe Gln Ala Leu Arg
145                 150                 155                 160

His Asp Leu Met Arg Ser Ser Ser Pro Ala Val Ser Ser
                165                 170
```

<210> SEQ ID NO 63
<211> LENGTH: 8
<212> TYPE: PRT
<213> ORGANISM: Artificial Sequence
<220> FEATURE:
<223> OTHER INFORMATION: FLAG tag

<400> SEQUENCE: 63

```
Asp Tyr Lys Asp Asp Asp Asp Lys
 1               5
```

<210> SEQ ID NO 64
<211> LENGTH: 10
<212> TYPE: PRT
<213> ORGANISM: Artificial Sequence
<220> FEATURE:
<223> OTHER INFORMATION: His tag

<400> SEQUENCE: 64

```
Gly Ser Gly Gly His His His His His His
```

<210> SEQ ID NO 65
<211> LENGTH: 1128
<212> TYPE: DNA
<213> ORGANISM: Artificial Sequence
<220> FEATURE:
<223> OTHER INFORMATION: zcyto33f2NHis
<220> FEATURE:
<221> NAME/KEY: CDS
<222> LOCATION: (1)...(1128)

<400> SEQUENCE: 65

```
atg gat gca atg aag aga ggg ctc tgc tgt gtg ctg ctg ctg tgt ggc      48
Met Asp Ala Met Lys Arg Gly Leu Cys Cys Val Leu Leu Leu Cys Gly
 1               5                  10                  15 gcc gtc ttc gtt tcg ctc agc cag gaa atc cat gcc gag ttg aga cgc      96
Ala Val Phe Val Ser Leu Ser Gln Glu Ile His Ala Glu Leu Arg Arg
             20                  25                  30 ttc cgt aga cat cac cat cac cat cac gga tct ggt gga cca aag agg     144
Phe Arg Arg His His His His His His Gly Ser Gly Gly Pro Lys Arg
         35                  40                  45 tcc tca tca ctg cca ttg aac cca gtc ctg cag acc tcc ctg gag gag     192
Ser Ser Ser Leu Pro Leu Asn Pro Val Leu Gln Thr Ser Leu Glu Glu
 50                  55                  60 gtg gag ctg ctc tac gag ttc ctg ctg gcc gaa ctt gag atc agc cct     240
Val Glu Leu Leu Tyr Glu Phe Leu Leu Ala Glu Leu Glu Ile Ser Pro
 65                  70                  75                  80 gac ctg cag atc tcc atc aag gac gag gag ctg gcc tcc ttg cgg aag     288
Asp Leu Gln Ile Ser Ile Lys Asp Glu Glu Leu Ala Ser Leu Arg Lys
                 85                  90                  95 gcc tca gac ttc cgc acc gtc tgc aac aac gtc atc ccc aag agc atc     336
Ala Ser Asp Phe Arg Thr Val Cys Asn Asn Val Ile Pro Lys Ser Ile
            100                 105                 110 cca gac atc cgc cgg ctc agc gcc agc ctc tcc agc cac cct ggc atc     384
Pro Asp Ile Arg Arg Leu Ser Ala Ser Leu Ser Ser His Pro Gly Ile
        115                 120                 125 ctc aag aaa gaa gac ttt gaa agg aca gtg ctg acc ctg gcc tac aca     432
Leu Lys Lys Glu Asp Phe Glu Arg Thr Val Leu Thr Leu Ala Tyr Thr
    130                 135                 140 gcc tac cgc aca gcc ctg tcc cac ggc cat cag aag gac atc tgg gcg     480
Ala Tyr Arg Thr Ala Leu Ser His Gly His Gln Lys Asp Ile Trp Ala
145                 150                 155                 160 cag tcc ctc gtt agc ctc ttc cag gcc ctg agg cac gac ttg atg cgc     528
Gln Ser Leu Val Ser Leu Phe Gln Ala Leu Arg His Asp Leu Met Arg
                165                 170                 175 tcc tca cag ccg gga gta cct ccc gga tct ggc agt agt aga ggc ggc     576
Ser Ser Gln Pro Gly Val Pro Pro Gly Ser Gly Ser Ser Arg Gly Gly
            180                 185                 190 tct gga agc gga gga agc gga gga gcc gga agt aaa ctg aga gct gtg     624
Ser Gly Ser Gly Gly Ser Gly Gly Ala Gly Ser Lys Leu Arg Ala Val
        195                 200                 205 cct ggg ggc agc agc cct gcc tgg act cag tgc cag cag ctt tca cag     672
Pro Gly Gly Ser Ser Pro Ala Trp Thr Gln Cys Gln Gln Leu Ser Gln
    210                 215                 220 aag ctc tgc aca ctg gcc tgg agt gca cat cca cta gtg gga cac atg     720
Lys Leu Cys Thr Leu Ala Trp Ser Ala His Pro Leu Val Gly His Met
225                 230                 235                 240 gat cta aga gaa gag gga gat gaa gag act aca aat gat gtt ccc cat     768
Asp Leu Arg Glu Glu Gly Asp Glu Glu Thr Thr Asn Asp Val Pro His
                245                 250                 255
```

```
atc cag tgt gga gat ggc tgt gac ccc caa gga ctc agg gac aac agt    816
Ile Gln Cys Gly Asp Gly Cys Asp Pro Gln Gly Leu Arg Asp Asn Ser
        260                 265                 270 cag ttc tgc ttg caa agg atc cac cag ggt ctg att ttt tat gag aag    864
Gln Phe Cys Leu Gln Arg Ile His Gln Gly Leu Ile Phe Tyr Glu Lys
            275                 280                 285 ctg cta gga tcg gat att ttc aca ggg gag cct tct ctg ctc cct gat    912
Leu Leu Gly Ser Asp Ile Phe Thr Gly Glu Pro Ser Leu Leu Pro Asp
        290                 295                 300 agc cct gtg gcg cag ctt cat gcc tcc cta ctg ggc ctc agc caa ctc    960
Ser Pro Val Ala Gln Leu His Ala Ser Leu Leu Gly Leu Ser Gln Leu
305                 310                 315                 320 ctg cag cct gag ggt cac cac tgg gag act cag cag att cca agc ctc   1008
Leu Gln Pro Glu Gly His His Trp Glu Thr Gln Gln Ile Pro Ser Leu
                325                 330                 335 agt ccc agc cag cca tgg cag cgt ctc ctt ctc cgc ttc aaa atc ctt   1056
Ser Pro Ser Gln Pro Trp Gln Arg Leu Leu Leu Arg Phe Lys Ile Leu
            340                 345                 350 cgc agc ctc cag gcc ttt gtg gct gta gcc gcc cgg gtc ttt gcc cat   1104
Arg Ser Leu Gln Ala Phe Val Ala Val Ala Ala Arg Val Phe Ala His
        355                 360                 365 gga gca gca acc ctg agt ccc taa                                   1128
Gly Ala Ala Thr Leu Ser Pro *
    370                 375

<210> SEQ ID NO 66
<211> LENGTH: 375
<212> TYPE: PRT
<213> ORGANISM: Artificial Sequence
<220> FEATURE:
<223> OTHER INFORMATION: zcyto33f2NHis

<400> SEQUENCE: 66

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg His His His His His His Gly Ser Gly Pro Lys Arg
        35                  40                  45

Ser Ser Ser Leu Pro Leu Asn Pro Val Leu Gln Thr Ser Leu Glu Glu
    50                  55                  60

Val Glu Leu Leu Tyr Glu Phe Leu Leu Ala Glu Leu Glu Ile Ser Pro
65                  70                  75                  80

Asp Leu Gln Ile Ser Ile Lys Asp Glu Glu Leu Ala Ser Leu Arg Lys
                85                  90                  95

Ala Ser Asp Phe Arg Thr Val Cys Asn Asn Val Ile Pro Lys Ser Ile
            100                 105                 110

Pro Asp Ile Arg Arg Leu Ser Ala Ser Leu Ser Ser His Pro Gly Ile
        115                 120                 125

Leu Lys Lys Glu Asp Phe Glu Arg Thr Val Leu Thr Leu Ala Tyr Thr
    130                 135                 140

Ala Tyr Arg Thr Ala Leu Ser His Gly His Gln Lys Asp Ile Trp Ala
145                 150                 155                 160

Gln Ser Leu Val Ser Leu Phe Gln Ala Leu Arg His Asp Leu Met Arg
                165                 170                 175

Ser Ser Gln Pro Gly Val Pro Pro Gly Ser Gly Ser Ser Arg Gly Gly
            180                 185                 190

Ser Gly Ser Gly Gly Ser Gly Gly Ala Gly Ser Lys Leu Arg Ala Val
```

```
              195                 200                 205
Pro Gly Gly Ser Ser Pro Ala Trp Thr Gln Cys Gln Gln Leu Ser Gln
    210                 215                 220

Lys Leu Cys Thr Leu Ala Trp Ser Ala His Pro Leu Val Gly His Met
225                 230                 235                 240

Asp Leu Arg Glu Glu Gly Asp Glu Thr Thr Asn Asp Val Pro His
                245                 250                 255

Ile Gln Cys Gly Asp Gly Cys Asp Pro Gln Gly Leu Arg Asp Asn Ser
                260                 265                 270

Gln Phe Cys Leu Gln Arg Ile His Gln Gly Leu Ile Phe Tyr Glu Lys
                275                 280                 285

Leu Leu Gly Ser Asp Ile Phe Thr Gly Glu Pro Ser Leu Leu Pro Asp
    290                 295                 300

Ser Pro Val Ala Gln Leu His Ala Ser Leu Leu Gly Leu Ser Gln Leu
305                 310                 315                 320

Leu Gln Pro Glu Gly His His Trp Glu Thr Gln Gln Ile Pro Ser Leu
                325                 330                 335

Ser Pro Ser Gln Pro Trp Gln Arg Leu Leu Leu Arg Phe Lys Ile Leu
                340                 345                 350

Arg Ser Leu Gln Ala Phe Val Ala Val Ala Ala Arg Val Phe Ala His
                355                 360                 365

Gly Ala Ala Thr Leu Ser Pro
    370                 375

<210> SEQ ID NO 67
<211> LENGTH: 32
<212> TYPE: DNA
<213> ORGANISM: Artificial Sequence
<220> FEATURE:
<223> OTHER INFORMATION: oligonucleotide primer ZC50983

<400> SEQUENCE: 67
gtatacggcc ggccaccatg gatgcaatga ag                             32

<210> SEQ ID NO 68
<211> LENGTH: 32
<212> TYPE: DNA
<213> ORGANISM: Artificial Sequence
<220> FEATURE:
<223> OTHER INFORMATION: oligonucleotide primer ZC50984

<400> SEQUENCE: 68
gttatcggcg cgcctaagct gttggcacta ag                             32

<210> SEQ ID NO 69
<211> LENGTH: 41
<212> TYPE: DNA
<213> ORGANISM: Artificial Sequence
<220> FEATURE:
<223> OTHER INFORMATION: oligonucleotide primer ZC52289

<400> SEQUENCE: 69
cacacaggcc ggccaccatg tgtcaatcac gctacctcct c                   41

<210> SEQ ID NO 70
<211> LENGTH: 41
<212> TYPE: DNA
<213> ORGANISM: Artificial Sequence
```

```
-continued

<220> FEATURE:
<223> OTHER INFORMATION: oligonucleotide primer ZC52290

<400> SEQUENCE: 70
cacacaggcg cgccttatcc accagatccg gatgacacag c                    41
```

HETERODIMERIC FOUR HELIX BUNDLE CYTOKINES

CROSS-REFERENCE TO RELATED APPLICATIONS

This application is a divisional of U.S. patent application Ser. No. 11/486,758, filed Jul. 14, 2006, now U.S. Pat. No. 7,196,172 and claims the benefit of U.S. Provisional Application Ser. No. 60/700,550, filed Jul. 19, 2005, and U.S. Provisional Application Ser. No. 60/699,938, filed Jul. 15, 2005, all of which are herein incorporated by reference.

BACKGROUND OF THE INVENTION

Cytokines are polypeptide hormones that are produced by a cell and affect cell growth or metabolism in either autocrine, paracrine or endocrine fashion. Cytokines are physicochemically diverse, ranging in size from 5 kDa (TGF-α) to 140 kDa (Mullerian-inhibiting substance). Structurally, cytokines include a group distinguished by their four-helix bundle conformation. They include single polypeptide chains, as well as disulfide-linked homodimers and heterodimers.

The IL-12 family of cytokines is involved in immunomodulatory activities. Proteins in the IL-12 family are heterodimers and include IL-12, IL-23 and IL-27. IL-12 is a heterodimer comprising a p35 and p40 subunit (Kobayashi et al., *J. Exp. Med.* 170:827-845, 1989), IL-23 comprises p19 and p40 subunits (Oppman et al., *Immunity* 13:715-725, 2000), and IL-27 heterodimer comprises subunits p28 and Epstein Barr virus-induced protein 3 (EBI3; Pflanz et al., *Immunity* 16:779-790, 2002).

In view of the proven clinical utility of cytokines, there is a need in the art for additional such molecules for use as both therapeutic agents and research tools and reagents. Cytokines are used in the laboratory to study developmental processes, and in laboratory and industry settings as components of cell culture media.

SUMMARY OF THE INVENTION

The present invention provides for fusion proteins comprising at least two polypeptides wherein a first polypeptide comprises a sequence of amino acid residues 1 to 156 as shown in SEQ ID NO: 2 and a second polypeptide comprises a sequence of amino acid residues as shown in SEQ ID NO: 3 or SEQ ID NO: 4.

In another aspect, the present invention provides for fusion proteins comprising at least two polypeptides wherein a first polypeptide comprises a sequence of amino acid residues 6 to 156 as shown in SEQ ID NO: 2 and a second polypeptide comprises a sequence of amino acid residues as shown in SEQ ID NO: 3 or SEQ ID NO: 4.

The present invention also provides for fusion proteins comprising at least two polypeptides wherein a first polypeptide comprises a sequence of amino acid residues 21 to 156 as shown in SEQ ID NO: 2 and a second polypeptide comprises a sequence of amino acid residues as shown in SEQ ID NO: 3 or SEQ ID NO: 4.

In certain embodiments, the fusion proteins will also comprise a peptide linker as shown in SEQ ID NO: 33 or 38 between the first polypeptide and the second polypeptide.

In another aspect, the present invention provides an isolated polypeptide comprising amino acid residues 1 to 361 as shown in SEQ ID NO: 50, an isolated polypeptide comprising amino acid residues 1 to 346 as shown in SEQ ID NO: 52, an isolated polypeptide comprising amino acid residues 1 to 425 as shown in SEQ ID NO: 56, or an isolated polypeptide comprising amino acid residues 1 to 410 as shown in SEQ ID NO: 58.

The present invention provides polynucleotides molecules encoding the polypeptides, including polypeptides comprising fusion proteins disclosed herein. In certain embodiments, the present invention provides expression vector comprising the following operably linked elements, a transcription promoter, a DNA segment encoding the polypeptides, including fusion proteins, and a transcription terminator disclosed herein. Furthermore, the present invention provides cultured cells into the expression vectors have been introduced.

In another aspect, the present invention provides a method of treating an inflammatory disease comprising administering to a subject a therapeutically effective amount of a protein selected from the group consisting of: (a) a sequence of amino acid residues 1 to 156 as shown in SEQ ID NO: 2 and a second polypeptide comprises a sequence of amino acid residues as shown in SEQ ID NO: 3 or SEQ ID NO: 4; (b) a sequence of amino acid residues 6 to 156 as shown in SEQ ID NO: 2 and a second polypeptide comprises a sequence of amino acid residues as shown in SEQ ID NO: 3 or SEQ ID NO: 4; and (c) a sequence of amino acid residues 21 to 156 as shown in SEQ ID NO: 2 and a second polypeptide comprises a sequence of amino acid residues as shown in SEQ ID NO: 3 or SEQ ID NO: 4. In one embodiment, the inflammatory disease is asthma or inflammatory bowel disease (IBD).

In another aspect, the present invention provides a method of treating an autoimmune disease comprising administering to a subject a therapeutically effective amount of a protein selected from the group consisting of: (a) a sequence of amino acid residues 1 to 156 as shown in SEQ ID NO: 2 and a second polypeptide comprises a sequence of amino acid residues as shown in SEQ ID NO: 3 or SEQ ID NO: 4; (b) a sequence of amino acid residues 6 to 156 as shown in SEQ ID NO: 2 and a second polypeptide comprises a sequence of amino acid residues as shown in SEQ ID NO: 3 or SEQ ID NO: 4; and (c) a sequence of amino acid residues 21 to 156 as shown in SEQ ID NO: 2 and a second polypeptide comprises a sequence of amino acid residues as shown in SEQ ID NO: 3 or SEQ ID NO: 4. In one embodiment, the autoimmune disease is selected from the group consisting of muscular sclerosis, diabetes, rheumatoid arthritis and graft versus host disease (GVHD).

In another aspect, the present invention provides a method of stimulating or expanding T regulatory cells in a subject with an autoimmune or inflammatory disease comprising administering a therapeutically effective amount of a protein selected from the group consisting of: (a) a sequence of amino acid residues 1 to 156 as shown in SEQ ID NO: 2 and a second polypeptide comprises a sequence of amino acid residues as shown in SEQ ID NO: 3 or SEQ ID NO: 4; (b) a sequence of amino acid residues 6 to 156 as shown in SEQ ID NO: 2 and a second polypeptide comprises a sequence of amino acid residues as shown in SEQ ID NO: 3 or SEQ ID NO: 4; and (c) a sequence of amino acid residues 21 to 156 as shown in SEQ ID NO: 2 and a second polypeptide comprises a sequence of amino acid residues as shown in SEQ ID NO: 3 or SEQ ID NO: 4. In one embodiment, the autoimmune disease is selected from the group consisting of muscular sclerosis, diabetes, rheumatoid arthritis and graft versus host disease (GVHD). In another embodiment, the inflammatory disease is asthma or inflammatory bowel disease (IBD).

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "cancer" or "cancer cell" is used herein to denote a tissue or cell found in a neoplasm which possesses characteristics which differentiate it from normal tissue or tissue cells. Among such characteristics include but are not limited to: degree of anaplasia, irregularity in shape, indistinctness of cell outline, nuclear size, changes in structure of nucleus or cytoplasm, other phenotypic changes, presence of cellular proteins indicative of a cancerous or pre-cancerous state, increased number of mitoses, and ability to metastasize. Words pertaining to "cancer" include carcinoma, sarcoma, tumor, epithelioma, leukemia, lymphoma, polyp, and scirrus, transformation, neoplasm, and the like.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "level" when referring to immune cells, such as NK cells, T cells, in particular cytotoxic T cells, B cells and the like, an increased level is either increased number of cells or enhanced activity of cell function.

The term "level" when referring to viral infections refers to a change in the level of viral infection and includes, but is not limited to, a change in the level of CTLs or NK cells (as described above), a decrease in viral load, an increase antiviral antibody titer, decrease in serological levels of alanine aminotransferase, or improvement as determined by histological examination of a target tissue or organ. Determination of whether these changes in level are significant differences or changes is well within the skill of one in the art.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e. invasive and metastatic, or benign.

The term "operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "therapeutically effective amount" is defined as an amount of a zcyto33f2 or zcyto35f2 composition, or zcyto33f2 or zcyto35f2 composition in combination with another therapeutical agent, that results in a improvement in a subject having an inflammatory or autoimmune disease. What constitutes an improvement in a disease is well known to clinicians and those skilled in the art and is not limited to the descriptions given herein.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery that a previously identified four helical cytokine, zsig81 can be co-expressed with two separate proteins forming covalently disulfide-linked heterodimeric proteins. Zsig81 protein has been previously described in U.S. Pat. No. 6,531,576, which is incorporated herein by reference. In one aspect of the present invention, zsig81 is co-expressed with p35 (also designated IL-12A), and the resulting heterodimeric protein has been designated as zcyto35f2. In another aspect, the present invention provides co-expression of zsig81 with p19 (also designated IL-23A), and the resulting heterodimeric protein has been designated zcyto33f2. IL-12A and IL-23 are both members of the IL-12 family.

The IL-12 family of cytokines is involved in immunomodulatory activities. Proteins in the IL-12 family are heterodimers and include IL-12, IL-23 and IL-27. IL-12 is a heterodimer comprising a p35 and p40 subunit (Kobayashi et al., *J. Exp. Med.* 170:827-845, 1989), IL-23 comprises p19 and p40 subunits (Oppman et al., *Immunity* 13:715-725, 2000), and IL-27 heterodimer comprises subunits p28 and Epstein Barr virus-induced protein 3 (EBI3; Pflanz et al., *Immunity* 16:779-790, 2002). The genes encoding the respective cytokines must be expressed in the same cell in order to assemble a biologically active, heterodimeric cytokine (Oppman et al., 2000, ibid., Pflanz et al., *Immunity* 16:779-790, 2002, Wolf et al., *J. of Immunology*, 146: 3074, 1991), and for IL-12p40, IL-27p28 and EBI-3 expression is restricted to the cells that produce the biologically active heterodimeric cytokines (Pflanz et al., 2002, ibid.; Oppman et al., 2000 ibid.; D'Andrea et al., *J. Exp. Med*, 176:1387). In contrast, IL12p35 and IL23p19, as well as being expressed in cells that produce biologically active IL-12 or IL-23, are also expressed in cells and tissues that do not express p40, suggesting that another protein pairs with IL12p35 and IL23p19 in these cells and tissues (Maaser et al., *Immunology*, 112:437-445). Zsig81 is also expressed in tissues that express IL12p35 and IL23p19, but not IL12p40.

Human gut epithelial-derived cell lines CaCo2 (ATCC No. HTB-37) and HT-29 (ATCC No. HTB-38) were stimulated with either IL-1α, TNFα, IFNγ or combination thereof, as shown in the following examples. PCR analyses revealed that p19 RNA is present after stimulation with IL-1α and TNFα, and p35 RNA is present after stimulation with IFNγ. Zsig81 RNA was shown to be constitutively expressed in gut epithelial cells, while p40 RNA was not present under any of the conditions tested. P40 has been shown to be expressed in lymphoid tissue, but not epithelial tissue. These data indicate that zsig81 forms heterodimers with p19 and p35 in epithelial cell types, including lung and gut epithelium, under physiological conditions such as inflammation. These heterodimeric cytokines likely play a role in modulating the immune response in these tissues. Further studies were done using zsig81 knock out mice to investigate the role of zsig81 in modulating inflammation in lung tissue, particularly asthma. The localized expression of zsig81, IL23p19 and IL12p35, but not IL12p40 suggest a role for zsig81 in mucosal immunity.

zsig81 KO's show susceptibility to both oxazalone induced IBD and Ova induced asthma. Zcyto33 and cyto35 transgenic animals show a decreased number of mature B-cells, which also have impaired function. Furthermore, the spleens of zcyto35 transgenic animals have a large population of CD4+, CD25+ T regulatory cells.

T regulatory cells have been shown to protect against antigen induced immune-response including: Ova induced airway hyper-reactivity (Kabbur P M, et al. *Cellular Immunol.* 239 (1):67-74, 2006), and IBD (Holmen, N., et al. *Inflammatory Bowel Diseases.* 12 (6):447-456, 2006, Mudter, J., et al. *Current Opinions in Gastroenterology.* 19 (4): 343-349, 2006). In addition, regulatory T-cells have also been shown to play a role in control of autoimmune diseases such as, muscular sclerosis using a murine model of EAE (Zhang X., et al., *Internat. Immunol.* 18 (4):495-503, 2006), type 1 diabetes (Li, Alice, et al., *Vaccine* 24 (3):50036-46, 2006; Bruder, D., et al., *Diabetes* 54 (12):3395-33401, 2005) and rheumatoid arthritis (Cao, D, et al. *Scandinavian J. of Immunol.* 63 (6):444-52, 2006). Finally, induction of regulatory T-cells is protective against the development of GVHD (Karakhanova, S., et al., *J. of Immunotherapy* 29 (3): 336-349, 2006).

From the data generated through the analysis of zsig81 knockout mice and zcyto33 and zcyto35 transgenic mice, these cytokines may be important for dampening the immune system in lung and gut and therefore useful for the treatment of inflammatory diseases such as asthma and inflammatory bowel disease (IBD). Furthermore, enhancement of T regulatory cells number and function by zcyto35 would be useful for treatment of autoimmune disease and for inhibition of graft versus host disease (GVHD).

In general, a DNA sequence encoding a zsig81 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Exemplary expression constructs are described in U.S. Pat. No. 6,531,576 and the example section herein.

Zsig81 is co-expressed with either p35 or p19, particularly in mammalian expression systems. Polynucleotide constructs for co-expressing p19 are made, for example, as taught in Opperman et al. (Immunity 13:715-725, 2000). An exemplary method for preparing p35 expression constructs is taught in Koybayaski et al. (*J. Exp. Med.* 170:827-845, 1989.

Single chain components of the heterodimeric proteins may also be expressed in prokaryotic systems. Tandem, single-chain molecules zcyto33f2 can be expressed as a single-chain fusion protein comprised of the zsig81 (SEQ ID NO: 2) protein fused at the carboxy terminus to a peptide linker (SEQ ID NO: 33) followed by the p19 protein (SEQ ID NO: 4). The opposite orientation may also be expressed, with the p19 protein (SEQ ID NO: 4) fused at the carboxy terminus to a peptide linker (seq I.D. SEQ ID NO: 33) followed by the zsig81 protein (SEQ ID NO: 2). The single-chain fusion protein can be secreted from the cell using the native secretion leader sequence for either zsig81 or p19, or by using a heterologous secretion leader sequence, such as the secretion leader sequence from TPA or HGH. Furthermore, the single-chain fusion protein can be expressed with an affinity tag fused either to the amino terminus or the carboxy terminus.

Zcyto35f2 can be expressed as a single-chain fusion protein comprised of the zsig81 (SEQ ID NO: 2) protein fused at the carboxy terminus to a peptide linker (SEQ ID NO: 33) followed by the p35 protein (SEQ ID NO: 6). The opposite orientation may also be expressed, with the p35 protein (SEQ ID NO: 6) fused at the carboxy terminus to a peptide linker (SEQ ID NO: 33) followed by the zsig81 protein (SEQ ID NO: 2). The fusion protein can be secreted from the cell using the native secretion leader sequence for either zsig81 or p35, or by using a heterologous secretion leader sequence, such as the secretion leader sequence from TPA or HGH. Furthermore, the single chain fusion protein can be expressed with an affinity tag fused either to the amino terminus or the carboxy terminus.

To direct a zsig81 and p19 or p35 polypeptides into the secretory pathway of a host cell, a secretory signal sequence (also known as a leader sequence, prepro sequence or pre sequence) is provided in the expression vector. The secretory signal sequence may the native secretory sequence, i.e. zsig81, p19 or p35, or may be derived from another secreted protein (e.g., t-PA; see, U.S. Pat. No. 5,641,655) or synthesized de novo. The secretory signal sequence is operably linked to the zsig81, p19 or p35 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al, U.S. Pat. No. 4,579,821; and Ringold, U.S. Pat. No. 4,656,134. Suitable cultured mammalian cells include the HEK293T (ATCC No. CRL 11268), COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59-72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Zsig81 and p19 or p35 can be expressed as single chain molecules in prokaryotic expression systems. The polypeptides are then dimerized to form zcyto33f2 or zcyto35f2. A wide variety of suitable recombinant host cells includes, but is not limited to, gram-negative prokaryotic host organisms. Standard techniques for propagating vectors in prokaryotic hosts are well-known to those of skill in the art (see, for example, Ausubel et al. (eds.), *Short Protocols in Molecular Biology*, 3rd Edition (John Wiley & Sons 1995); Wu et al., *Methods in Gene Biotechnology* (CRC Press, Inc. 1997)). Fungal cells, including yeast cells, can also be used within the present invention.

Expressed recombinant zsig81, zcyto33f2 or zcyto35f2 proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

Zsig81, p19 and p35 polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989.

Using methods known in the art, zcyto33f2 and zcyto35f2 proteins are prepared as heterodimers and may be glycosylated or non-glycosylated; pegylated or non-pegylated; and may or may not include an initial methionine amino acid residue.

Target cells for use in zcyto33f2 and zcyto35f2 activity assays include, without limitation, vascular cells (especially endothelial cells and smooth muscle cells), hematopoietic (myeloid, erythroid and lymphoid) cells, liver cells (including hepatocytes, fenestrated endothelial cells, Kupffer cells, and Ito cells), fibroblasts (including human dermal fibroblasts and lung fibroblasts), fetal lung cells, articular synoviocytes, pericytes, chondrocytes, osteoblasts, and epithelial cells. Endothelial cells and hematopoietic cells are derived from a common ancestral cell, the hemangioblast (Choi et al., *Development* 125:725-732, 1998).

Biological activity of zcyto33f2 and zcyto35f2 proteins are assayed using in vitro or in vivo assays designed to detect cell proliferation, differentiation, migration or adhesion; or changes in cellular metabolism (e.g., production of other growth factors or other macromolecules). Many suitable assays are known in the art, and representative assays are disclosed herein. Assays using cultured cells are most convenient for screening, such as for determining the effects of amino acid substitutions, deletions, or insertions. However, in view of the complexity of developmental processes (e.g., angiogenesis, wound healing, autoimmunity), in vivo assays will generally be employed to confirm and further characterize biological activity. Assays can be conducted using zcyto33f2 and zcyto35f2 proteins alone or in combination with other growth factors, such as members of the VEGF family or hematopoietic cytokines (e.g., EPO, TPO, G-CSF, stem cell factor). Representative assays are disclosed below.

Activity of zcyto33f2 and zcyto35f2 proteins can be measured in vitro using cultured cells or in vivo by administering molecules of the claimed invention to an appropriate animal model. Assays measuring cell proliferation or differentiation are well known in the art. For example, assays measuring proliferation include such assays as chemosensitivity to neutral red dye (Cavanaugh et al., *Investigational New Drugs* 8:347-354, 1990), incorporation of radiolabelled nucleotides (as disclosed by, e.g., Raines and Ross, *Methods Enzymol.* 109:749-773, 1985; Wahl et al., *Mol. Cell Biol.* 8:5016-5025, 1988; and Cook et al., *Analytical Biochem.* 179:1-7, 1989), incorporation of 5-bromo-2'-deoxyuridine (BrdU) in the DNA of proliferating cells (Porstmann et al., *J. Immunol. Methods* 82:169-179, 1985), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988). Differentiation can be assayed using suitable precursor cells that can be induced to differentiate into a more mature phenotype. Assays measuring differentiation include, for example, measuring cell-surface markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses,* 161-171, 1989).

Zcyto33f2 or zcyto35f2 activity may also be detected using assays designed to measure Zcyto33f2- or zcyto35f2-induced production of one or more additional growth factors or other macromolecules. Preferred such assays include those for determining the presence of hepatocyte growth factor (HGF), epidermal growth factor (EGF), transforming growth factor alpha (TGF☐), interleukin-6 (IL-6), VEGF, acidic fibroblast growth factor (aFGF), angiogenin, and other macromolecules produced by the liver. Suitable assays include mitogenesis assays using target cells responsive to the macromolecule of interest, receptor-binding assays, competition binding assays, immunological assays (e.g., ELISA), and other formats known in the art. Metalloprotease secretion is measured from treated primary human dermal fibroblasts, synoviocytes and chondrocytes. The relative levels of collagenase, gelatinase and stromalysin produced in response to culturing in the presence of a Zcyto33f2 or zcyto35f2 protein is measured using zymogram gels (Loita and Stetler-Stevenson, *Cancer Biology* 1:96-106, 1990). Procollagen/collagen synthesis by dermal fibroblasts and chondrocytes in response to a test protein is measured using 3H-proline incorporation into nascent secreted collagen. $^3$H-labeled collagen is visualized by SDS-PAGE followed by autoradiography (Unemori and Amento, *J. Biol. Chem.* 265: 10681-10685, 1990). Glycosaminoglycan (GAG) secretion from dermal fibroblasts and chondrocytes is measured using a 1,9-dimethylmethylene blue dye binding assay (Famdale et al., *Biochim. Biophys. Acta* 883:173-177, 1986). Collagen and GAG assays are also carried out in the presence of IL-1α or TGF-α to examine the ability of zcyto33f2 or zcyto35f2 protein to modify the established responses to these cytokines.

Monocyte activation assays are carried out (1) to look for the ability of zcyto33f2 or zcyto35f2 proteins to further stimulate monocyte activation, and (2) to examine the ability of zcyto33f2 or zcyto35f2 proteins to modulate attachment-induced or endotoxin-induced monocyte activation (Fuhlbrigge et al., J. Immunol. 138: 3799-3802, 1987). IL-1α and TNFα levels produced in response to activation are measured by ELISA (Biosource, Inc. Camarillo, Calif.). Monocyte/macrophage cells, by virtue of CD14 (LPS receptor), are exquisitely sensitive to endotoxin, and proteins with moderate levels of endotoxin-like activity will activate these cells.

Hematopoietic activity of zcyto33f2 or zcyto35f2 proteins can be assayed on various hematopoietic cells in culture. Preferred assays include primary bone marrow colony assays and later stage lineage-restricted colony assays, which are known in the art (e.g., Holly et al., WIPO Publication WO 95/21920). Marrow cells plated on a suitable semi-solid medium (e.g., 50% methylcellulose containing 15% fetal bovine serum, 10% bovine serum albumin, and 0.6% PSN antibiotic mix) are incubated in the presence of test polypeptide, then examined microscopically for colony formation. Known hematopoietic factors are used as controls. Mitogenic activity of zcyto33f2 or zcyto35f2 polypeptides on hematopoietic cell lines can be measured as disclosed above.

Cell migration is assayed essentially as disclosed by Kähler et al. (*Arteriosclerosis, Thrombosis, and Vascular Biology* 17:932-939, 1997). A protein is considered to be chemotactic if it induces migration of cells from an area of low protein concentration to an area of high protein concentration. A typical assay is performed using modified Boyden chambers with a polystryrene membrane separating the two chambers (Transwell; Corning Costar Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then extracted with 10% acetic acid and absorbance is measured at 600 nm. Migration is then calculated from a standard calibration curve. Cell migration can also be measured using the matrigel method of Grant et al. ("Angiogenesis as a component of epithelial-mesenchymal interactions" in Goldberg and Rosen, *Epithe-lial-Mesenchymal Interaction in Cancer*, Birkhäuser Verlag, 1995, 235-248; Baatout, *Anticancer Research* 17:451-456, 1997).

Cell adhesion activity is assayed essentially as disclosed by LaFleur et al. (*J. Biol. Chem.* 272:32798-32803, 1997). Briefly, microtiter plates are coated with the test protein, non-specific sites are blocked with BSA, and cells (such as smooth muscle cells, leukocytes, or endothelial cells) are plated at a density of approximately $10^4$-$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

Transgenic mice, engineered to express a zsig81 gene, zcyto33f2 or zcyto35f2 single chain sequence and mice that exhibit a complete absence of zsig81 gene function, referred to as "knockout mice" (Snouwaert et al., *Science* 257:1083, 1992), can also be generated (Lowell et al., *Nature* 366:740-742, 1993). These mice can be employed to study the zsig81 gene and the protein encoded thereby in an in vivo system. Transgenic mice are particularly useful for investigating the role of zsig81 proteins in early development in that they allow the identification of developmental abnormalities or blocks resulting from the over- or underexpression of a specific factor. See also, Maisonpierre et al., *Science* 277:55-60, 1997 and Hanahan, *Science* 277:48-50, 1997. Preferred promoters for transgenic expression include promoters from metallothionein and albumin genes.

Another approach uses a hydrodynamic push for in vivo transient expression. Proteins can also be expressed in vivo by systemic delivery a DNA plasmid encoding the protein of choice (Liu et al, *Gene Therapy*, 6:1258-66, 1999; Wang G et al., *Cancer Research*, 63:9016-22, 2003).

The DNA plasmid is delivered intravenously (i.v.) in blood-compatible buffer, usually saline. In mice, the optimal volume is approximately 0.6-0.9 times the blood volume (typically 1.5-2.0 mL) and is given by injection through the tail vein. When delivered i.v. in the tail vein in mice, the quasi-totality (>90%) of the circulating protein is produced by plasmid that is expressed in the liver, while smaller quantities are produced by plasmid in the heart, kidney, lungs and the spleen (Liu et al. ibid. 1999). It is conceivable that manipulating the promoter and enhancer regions of the plasmid DNA one can influence the strength and duration of protein expression.

Similarly, direct measurement of zsig81 polypeptide, or its loss of expression in a tissue can be determined in a tissue or cells as they undergo tumor progression. Increases in invasiveness and motility of cells, or the gain or loss of expression of zsig81 in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to zsig81 expression. For example, appearance or disappearance of polypeptides that regulate cell motility can be used to aid diagnosis and prognosis of prostate cancer (Banyard, J. and Zetter, B. R., *Cancer and Metast. Rev.* 17:449-458, 1999). As an effector of cell motility, or as a liver-specific marker, zsig81 gain or loss of expression may serve as a diagnostic for liver, neuroblastoma, endothelial, brain, and other cancers.

Moreover, the activity and effect of zcyto33f2 or zcyto35f2 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315-328,1994). For general reference see, O'Reilly M S, et al. *Cell* 79:315-328, 1994; and Rusciano D, et al. *Murine Models of Liver Metastasis. Invasion Metastasis* 14:349-361, 1995.

Zsig81 activity is expected to have a variety of therapeutic applications, particularly in tissues where p19 or p35 are expressed, such as mucosal epithelium. These therapeutic applications include treatment of diseases which require immune regulation, including autoimmune diseases such as rheumatoid arthritis, multiple sclerosis, myasthenia gravis, systemic lupus erythematosis, IBD, and diabetes, as well as asthma and lung hyperresponsiveness.

Zcyto33f2 or zcyto35f2 heteromultimeric proteins may be used either alone or in combination with other cytokines such as IL-3, G-CSF, GM-CSF, IL-4, M-CSF, IL-12, stem cell factor, IFN-$\alpha$ or IFN-$\gamma$ to modulate immune responses.

Administration of a zcyto33f2 or zcyto35f2 multimeric proteins to a subject can be topical, inhalant, intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). In general, pharmaceutical formulations will include a zcyto33f2 or zcyto35f2 polypeptide in combination with a pharmaceutically acceptable vehicle, such as saline, buffered saline, 5% dextrose in water, or the like. Other suitable vehicles are well-known to those in the art. A formulation is said to be a "pharmaceutically acceptable vehicle" if its administration can be tolerated by a recipient patient. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. Zcyto33f2 or zcyto35f2 will preferably be used in a concentration of about 10 to 100 µg/ml of total volume, although concentrations in the range of 1 ng/ml to 1000 µg/ml may be used. Determination of dose is within the level of ordinary skill in the art. Dosing is daily or intermittently over the period of treatment. Intravenous administration will be by bolus injection or infusion over a typical period of one to several hours. Sustained release formulations can also be employed. In general, a "therapeutically effective amount" of zcyto33f2 or zcyto35f2 multimeric proteins is an amount sufficient to produce a clinically significant change in the treated condition, such as a clinically significant change in hematopoietic or immune function, a significant reduction in morbidity, or a significantly increased histological score.

A pharmaceutical formulation comprising zcyto33f2 or zcyto35f2 multimeric proteins can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Polynucleotides encoding zcyto33f2 or zcyto35f2 multimeric proteins are useful within gene therapy applications where it is desired to increase or inhibit zcyto33f2 or zcyto35f2 multimeric protein activity. If a mammal has a mutated or absent zsig81 gene, a zsig81 gene can be introduced into the cells of the mammal.

Zcyto33f2 or zcyto35f2 multimeric proteins can be directly or indirectly conjugated to drugs, toxins, radionuclides and the like, and these conjugates used for in vivo diagnostic or therapeutic applications. For instance, polypeptides or antibodies of the present invention may be used to identify or treat tissues or organs that express a corresponding anti-complementary molecule (receptor or antigen, respectively, for instance). More specifically, zcyto33f2 or zcyto35f2 multimeric proteins, or bioactive fragments or portions thereof, can be coupled to detectable or cytotoxic molecules and delivered to a mammal having cells, tissues, or organs that express the anti-complementary molecule.

Suitable detectable molecules can be directly or indirectly attached to the polypeptide or antibody, and include radionuclides, enzymes, substrates, cofactors, inhibitors, fluorescent markers, chemiluminescent markers, magnetic particles, and the like. Suitable cytotoxic molecules can be directly or indirectly attached to the polypeptide or antibody, and include bacterial or plant toxins (for instance, *diphtheria* toxin, *Pseudomonas* exotoxin, ricin, abrin, saporin, and the like), as well as therapeutic radionuclides, such as iodine-131, rhenium-188 or yttrium-90. These can be either directly attached to the polypeptide or antibody, or indirectly attached according to known methods, such as through a chelating moiety. Polypeptides or antibodies can also be conjugated to cytotoxic drugs, such as adriamycin. For indirect attachment of a detectable or cytotoxic molecule, the detectable or cytotoxic molecule may be conjugated with a member of a complementary/anticomplementary pair, where the other member is bound to the polypeptide or antibody portion. For these purposes, biotin/streptavidin is an exemplary complementary/anticomplementary pair.

The invention is further illustrated by the following non-limiting examples.

EXAMPLES

Example 1

Expression Constructs

A. zsig81 Constructs

Constructs for the expression of zsig81 (SEQ ID NO: 2) were made in either pzMP41zeo or pZMP21. The pZMP41zeo is derived from plasmid pZMP40, where the zeocin resistance gene has been substituted for the DHFR gene and the CD8 gene was replaced with CD4. pZMP40 was cut with BglII, was used in a three-way recombination with both of the PCR insert fragments. Plasmid pZMP40 is a mammalian expression vector containing an expression cassette having the MPSV promoter, and multiple restriction sites for insertion of coding sequences; an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae. Plasmid pZMP40 was constructed from pZMP21 (deposited at the American Type Culture Collection, 10801 University Boulevard, Manassas, Va. 20110-2209, and designated No. PTA-5266) by addition of several restriction enzyme sites to the polylinker.

Furthermore, constructs for the expression zsig81 with either a C-terminal FLAG tag (SEQ ID NO:63) or a C-terminal 6×His tag (SEQ ID NO:64) were prepared. Using the cDNA encoding zsig81 as a template, PCR-amplified cDNAs for zsig81-Cflag or C-His were prepared using the oligonucleotides zc50071 (SEQ ID NO: 7) and zc50076 (SEQ ID NO: 8), or zc50071 (SEQ ID NO:7) and zc50156 (SEQ ID NO:9) as primers. Following agarose gel purification the cDNAs were inserted into EcoRI/BglII cut pzmp41zeo or pZMP21 by homologous recombination in yeast. Plasmid DNA was prepared in E. coli, DH10B (InVitrogen, Carlsbad, Calif.) and purified using QIAFILTER Maxi-prep kit (Qiagen, Valencia, Calif.) as described by manufacturer. All constructs were sequence verified.

B. Tandem Constructs 1. zcyto33f2NHis

Constructs for the expression of zcyto33f2 (which is zsig81 and p19 expressed as a single chain construct) were prepared in the expression vector pZMP21. Plasmid pZMP21 is a mammalian expression vector containing an expression cassette having the MPSV promoter, and multiple restriction sites for insertion of coding sequences; a TPA leader sequence, an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae, (deposited at the American Type Culture Collection, 10801 University Boulevard, Manassas, Va. 20110-2209, and designated No. PTA-5266).

Furthermore, constructs for the expression of zcyto33f2 with a N-terminal 6×His tag (SEQ ID NO:10) were prepared. Using the cDNA encoding zsig81 as a template, PCR-amplified cDNAs for zsig81 were prepared using the oligonucleotides zc50131 (SEQ ID NO: 28) and zc50080 (SEQ ID NO: 29) as primers. These cDNAs encode zsig81, beginning at P35 (shown as residue 18 of SEQ ID NO: 2), a 5' extension encoding an amino-terminal 6×his tag, and a 3' extension encoding a carboxy-terminal linker (SEQ ID NO: 32) Using cDNA encoding p19 as a template, PCR-amplified cDNAs for p19 were prepared using the oligonucleotides zc50085 (SEQ ID NO: 30) and zc50082 (SEQ ID NO: 31) as primers. These cDNAs encode p19, beginning at R20 (as shown in SEQ ID NO: 4), a 5' extension complementary to the 3' extension on the zsig81 cDNAs, encoding an amino-terminal linker. Following agarose gel purification the cDNAs were inserted into BglII cut pzmp21 by three-way yeast recombination in vivo. Yeast DNA was isolated and transformed into E. coli for amplification. Plasmid DNA was prepared in E. coli, DH10B and purified using QIAFILTER Maxi-prep kit (Qiagen, Valencia, Calif.) as described by manufacturer. All constructs were sequence verified.

2. zcyto33f2CHis

Constructs for the expression of zcyto33f2 were prepared in the expression vector pZMP21. Plasmid pZMP21 is a mammalian expression vector containing an expression cassette having the MPSV promoter, and multiple restriction sites for insertion of coding sequences; an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae, (deposited at the American Type Culture Collection, 10801 University Boulevard, Manassas, Va. 20110-2209, and designated No. PTA-5266).

Furthermore, constructs for the expression of zcyto33f2 with a C-terminal 6×His tag (SEQ ID NO:64) were prepared. Using the cDNA encoding zsig81 as a template, PCR-amplified cDNAs for zsig81 were prepared using the oligonucleotides zc50765 (SEQ ID NO: 34) and zc50768 (SEQ ID NO: 36), or zc50766 (SEQ ID NO: 35) and zc50768 (SEQ ID NO: 36) as primers. These cDNAs encode zsig81, beginning at W23 (shown as residue 6 in SEQ ID NO: 2) or S38 (shown as residue 21 in SEQ ID NO: 2), a 5' extension encoding an amino-terminal linker (SEQ ID NO: 37), and a 3' extension encoding a carboxy-terminal histidine tag. Using cDNA encoding p19 as a template, PCR-amplified cDNAs for p19 were prepared using the oligonucleotides zc50767 (SEQ ID NO: 39) and zc50769 (SEQ ID NO: 40) as primers. These cDNAs encode p19, beginning at M1 (as shown in SEQ ID NO: 4), a 3' extension complementary to the 5' extension on the zsig81 cDNAs, encoding a carboxy-terminal linker. Following agarose gel purification the cDNAs were inserted into EcoRI/BglII cut pzmp21 by three-way yeast recombination in vivo. Yeast DNA was isolated and transformed into E. coli for amplification. Plasmid DNA was prepared in E. coli, DH10B and purified using QIAFILTER Maxi-prep kit (Qiagen, Valencia, Calif.) as described by manufacturer. All constructs were sequence verified.

3. Murine zcyto33f2CHis

Constructs for the expression of murine zcyto33f2 were prepared in the expression vector pZMP21. Plasmid pZMP21 is a mammalian expression vector containing an expression cassette having the MPSV promoter, and multiple restriction sites for insertion of coding sequences; a TPA leader sequence, an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae, (deposited at the American Type Culture Collection, 10801 University Boulevard, Manassas, Va. 20110-2209, and designated No. PTA-5266).

Furthermore, constructs for the expression of murine zcyto33f2 a C-terminal 6×His tag (SEQ ID NO:64) were prepared. Using the cDNA encoding zsig81 as a template, PCR-amplified cDNAs for murine zsig81 were prepared using the oligonucleotides zc50660 (SEQ ID NO: 41) and zc50658 (SEQ ID NO: 42) as primers. These cDNAs encode zsig81, beginning at P35, a 3' extension encoding a carboxy-terminal linker (SEQ ID NO: 32 ). Using cDNA encoding murine p19 as a template, PCR-amplified cDNAs for murine p19 were prepared using the oligonucleotides zc50659 (SEQ ID NO: 43) and zc50657 (SEQ ID NO: 44) as primers. These cDNAs encode murine p19, beginning at R20, a 5' extension complementary to the 3' extension on the zsig81 cDNAs, encoding an amino-terminal linker, and a 3' extension encoding a 6×his tag. Following agarose gel purification the cDNAs were inserted into BglII cut pzmp21 by three-way yeast recombination in vivo. Yeast DNA was isolated and transformed into E. coli for amplification. Plasmid DNA was prepared in E. coli, DH10B and purified using QIAFILTER Maxi-prep kit (Qiagen, Valencia, Calif.) as described by manufacturer. All constructs were sequence verified.

4. Zcyto35CHis

Constructs for the expression of zcyto35f2 (which is zsig81 and p35 expressed as a single chain construct) were prepared in the expression vector pZMP21. Plasmid pZMP21 is a mammalian expression vector containing an expression cassette having the MPSV promoter, and multiple restriction sites for insertion of coding sequences; an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae, (deposited at the American Type Culture Collection, 10801 University Boulevard, Manassas, Va. 20110-2209, and designated No. PTA-5266).

Furthermore, constructs for the expression of zcyto35f2 with a C-terminal 6×His tag (SEQ ID NO:64) were prepared. Using the cDNA encoding zsig81 as a template, PCR-amplified cDNAs for zsig81 were prepared using the oligonucleotides zc50765 (SEQ ID NO: 34) and zc50768 (SEQ ID NO: 36), or zc50766 (SEQ ID NO: 35) and zc50768 (SEQ ID NO: 36) as primers. These cDNAs encode zsig81, beginning at W23 (shown as residue 6 of SEQ ID NO: 2) or S38 (shown as residue 21 of SEQ ID NO: 2), a 5' extension encoding an amino-terminal linker and a 3' extension encoding a carboxy-terminal histidine tag. Using cDNA encoding p35 as a template, PCR-amplified cDNAs for p35 (SEQ ID NO: 5) were prepared using the oligonucleotides zc51016 (SEQ ID NO: 45) and zc51017 (SEQ ID NO: 46) as primers. These cDNAs encode p35, beginning at M1 (SEQ ID NO: 6), a 3' extension complementary to the 5' extension on the zsig81 cDNAs, encoding an carboxy-terminal linker (SEQ ID NO: 32). Following agarose gel purification the cDNAs were inserted into EcoRI/BglII cut pzmp21 by three-way yeast recombination in vivo. Yeast DNA was isolated and transformed into E. coli for amplification. Plasmid DNA was prepared in E. coli DH10B and purified using QIAFILTER Maxi-prep kit (Qiagen, Valencia, Calif.) as described by manufacturer. All constructs were sequence verified.

5. Murine zcyto35f2CHis

Constructs for the expression of murine zcyto35f2 were prepared in the expression vector pZMP21. Plasmid pZMP21 is a mammalian expression vector containing an expression cassette having the MPSV promoter, and multiple restriction sites for insertion of coding sequences; a TPA leader sequence, an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae, (deposited at the American Type Culture Collection, 10801 University Boulevard, Manassas, Va. 20110-2209, and designated No. PTA-5266).

Furthermore, constructs for the expression of murine zcyto35f2 (SEQ ID NO: 59) with a C-terminal 6×His tag (SEQ ID NO:6) were prepared. Using the cDNA encoding zsig81 as a template, PCR-amplified cDNAs for murine zsig81 were prepared using the oligonucleotides zc51754 (SEQ ID NO: 47) and zc51759 (SEQ ID NO: 48) as primers. These cDNAs encode zsig81, beginning at R22, a 5' extension encoding a carboxy-terminal linker (SEQ ID NO: 32 ), and a 3' extension encoding a C-terminal 6×his tag. Using cDNA encoding murine p35 as a template, PCR-amplified cDNAs for murine p35 were prepared using the oligonucleotides zc50659 (SEQ ID NO: 43) and zc50657 (SEQ ID NO: 44) as primers. These cDNAs encode murine p35, beginning at M1, and a 5' extension complementary to the 3' extension on the zsig81 cDNAs, encoding an amino-terminal linker. Following agarose gel purification the cDNAs were inserted into BglII cut pzmp21 by three-way yeast recombination in vivo. Yeast DNA was isolated and transformed into E. coli for amplification. Plasmid DNA was prepared in E. coli DH10B and purified using QIAFILTER Maxi-prep kit (Qiagen, Valencia, Calif.) as described by manufacturer. All constructs were sequence verified.

C. Expression in HEK293T Cells 1. zsig81

HEK293T cells (ATCC No. CRL 11268) were transfected with expression constructs for zsig81 M1-Cflag or zsig81CHis. Lipofectamine 2000 (12 µL) was combined with 3 µg of construct DNA and allowed to complex at 25° C. for 20 min. 2×10$^6$ 293T cells were added to the Lipofectamine 2000 complex and incubated at 37° C. for 30 min. Transfected cells were then plated into 6-well collagen coated plates for 24 hrs. Cells were then switched to serum-free media and incubated for an additional 48 hrs. The conditioned media (CM) was collected (5 mL) and spun down to remove debris. The transfected cells were lysed in 1.5 RIPA lysis buffer (20 mM Tris:HCL, pH 7.4, 150 mM NaCl, 2 mM EGTA, 1% TX-100, and complete protease inhibitors (Roche Diagnostics, Mannheim, Germany)) and spun down to remove debris. The CM was incubated overnight at 4° C. with either 50 µl Anti-FlagM2-Agarose (Sigma Chemical Co., St. Louis, Mo.) or 50 µl NiNTA (Qiagen, Valencia, Calif.). The affinity resin was collected, washed with PBS and the bound proteins were eluted in 50 µl 2× reducing loading buffer (InVitrogen, Carlsbad, Calif.) at 80° C. The samples were then analyzed by western blot using Anti-FlagM2 antibody (Sigma Chemical Co., St. Louis, Mo.) or Anti-His antibody (R&D Systems, Minneapolis, Minn.). All of the zsig81-Cflag or zsig81-Chis protein expressed in HEK293T cells that were transfected with the respective expression vectors, was cell associated, and no zsig81X1M1-Cflag or zsig81-Chis protein was found in the CM.

2. zcyto33f2 and zcyto35f2

HEK293T cells (ATCC No. CRL 11268) were transfected with expression constructs for human zcyto33f2Chis, human zcyto33Nhis, murine zcyto33f2Chis, human zcyto35f2Chis, and murine zcyto35f2Chis. Lipofectamine 2000 (12 µL) was combined with 3 µg of construct DNA and allowed to complex at 25° C. for 20 min. 2×10$^6$ 293T cells were added to the Lipofectamine 2000 complex and incubated at 37° C. for 30 min. Transfected cells were then plated, in serum free medium, into 35 mm tissue culture plates (Costar) for 48 hrs. The conditioned media (CM) was collected (5 mLs) and spun down to remove debris. The transfected cells were lysed in 1.5

RIPA lysis buffer (20 mM Tris:HCL, pH 7.4, 150 mM NaCl, 2mM EGTA, 1% TX-100, and complete protease inhibitors (Roche Diagnostics, Mannheim, Germany)) and spun down to remove debris. The CM was incubated overnight at 4° C. with either 50 µl NiNTA (Qiagen, Valencia, Calif.). The affinity resin was collected, washed with PBS and the bound proteins were eluted in 50 µl 2× reducing loading buffer (InVitrogen, Carlsbad, Calif.) at 80° C. The samples were then analyzed by western blot using Anti-His antibody (R&D Systems, Minneapolis, Minn.). All of the His-tagged protein expressed in HEK293T cells, transfected with the respective expression vectors, was found in the CM.

Example 2

Co-Expression with IL-6 and IL-12 Family Members

Expression constructs for zsig81-Cflag or zsig81-Chis were transfected in combination with expression constructs for IL23A (Oppman et al., *Immunity* 13:715-725, 2000), IL-12p35, IL12p40 (Koybayaski et al., *J. Exp. Med.* 170:827-845, 1989), EBI3 (Pflanz et al., *Immunity* 16:779-790, 2002), soluble IL-6 receptor (IL-6Sr; Lust, et al., *Cytokine*, 4 (2):, 96-100, 1992), Ciliary Neurotrophic Factor Receptor (CNTFR; Panayotaros, et. al,. *Biochemistry*, 33 (19): 5813-5818, 1994), Cardiotrophin-Like Cytokine or CLF—Cytokine-Like Factor. (CLC and CLF; Elson, et. al, *Nature Neuroscience*, 3 (9): 867-872, 2000), or LIF (SEQ ID NO:10) into HEK293T cells. Lipofectamine 2000 (InVitrogen, Carlsbad, Calif.) was combined with 3 ug of each construct DNA and allowed to complex at 25° C. for 20 min. 2×10$^6$ HEK293T cells were added to the Lipofectamine 2000 (Invitrogen, Carlsbad, Calif.) complex and incubated at 37° C. for 30 min. Transfected cells were then plated into 6-well collagen coated plates for 24 hrs. Culture medium was removed and replaced with serum-free media, and the cell were incubated for and additional 48 hrs. After 48 hrs., the conditioned media was collected and cleared of cell debris by centrifuge. The cells were lysed with RIPA lysis buffer (1.5 mLs) and the lysate was cleared of cell debris by centrifuge. Both conditioned media and whole cell lysates were combined with 50 µl Ni NTA-agarose (Qiagen, Valencia, Calif.). Conditioned medium and lysate from the cells transfected with zsig81 alone were combined with 50 µl of anti-FLAG agarose (Sigma Chemical Co., St. Louis, Mo.). Following an overnight incubation, the resins from the immunoprecipitation reactions were pelleted and washed once with PBS and then analyzed by SDS-PAGE and western blot. Blots were incubated with an anti-FLAG-bio M2 antibody (1:3000) overnight at 4° C. with agitation. Blots were then washed and then avidin-HRP (1:5000) was added for 1 hr. at 25° C. After a final wash, ECL was used to visualize the Western blots. The western blots show that when zsig81-Cflag or zsig81-Chis are expressed alone, the majority of the zsig81-Cflag or zsig81-Chis protein is retained in the whole cell lysate fraction. Co-expression of zsig81-Cflag or zsig81-Chis with IL23A-C-His or IL23A-CFlag, resulted in the secretion of both zsig81-CTag and IL-23A-Ctag. Furthermore, Co-expression of zsig81-Cflag or zsig81-Chis with IL12p35-C-his or IL12p35-Cflag, resulted in the secretion of both zsig81-Ctag and IL12p35-Ctag In contrast, co-expression of zsig81-Cflag or zsig81-Chis with the other members of the IL-6 and IL-12 family members did not lead to secretion of either zsig81-Cflag or zsig81-Chis. These data show that IL23A and IL12p35, but none of the other proteins tested, could stimulate the secretion of zsig81-Cflag or zsig81-Chis.

In a subsequent experiment when zsig81-Cflag and IL23A-Chis were co-expressed in the same cell, either Ni NTA-agarose (Qiagen, Valencia, Calif.) or an anti-Flag antibody (Sigma Chemical Co., St Louis, Mo.) were able to immunoprecipitate zsig81-Cflag from 293T conditioned media. In addition, anti-FLAG-agarose (Sigma Chemical Co., St Louis, Mo.) was able to capture IL23A-Chis from the same conditioned medium. Additional experiments showed that when zsig81Cflag and IL12p35Chis were co-expressed in the same cell, either Ni NTA-agarose (Qiagen, Valencia, Calif.) or an anti-Flag antibody (sigma Chemical Co., St Louis, Mo.)+Ni NTA-agarose were able to immunoprecipitate zsig81Cflag from 293T conditioned media. In addition, anti-FLAG-agarose (Sigma Chemical Co., St Louis, Mo.) was able to capture IL12p35Chis from the same conditioned medium. These data demonstrate a close association zsig81Cflag with both IL12p35Chis and p19Chis.

The results of these experiments show that secretion of zsig81-Cflag is dependent on the co-expression of either IL12p35CHis or p19CHis, illustrated by the lack of secretion of zsig81Cflag when paired with other proteins of the 11-6 or IL12 family and the robust secretion in the presence of IL12p35Chis or p19Chis. Furthermore, the immunoprecipitation experiments showed that there is a close association of zsi81Cflag, and IL12p35Chis or p19Chis.

Example 3

Isolation of RNA Samples for Expression Profiling

Total RNA was purified from resting and stimulated cell lines grown in-house and purified using an acid-phenol purification protocol (Chomczynski and Sacchi, Analytical Biochemistry, 162:156-9, 1987). The quality of the RNA was assessed by running an aliquot on an Agilent Bioanalyzer according to the manufacturer's instructions. The total RNA was DNAsed using DNA-free reagents (Ambion, Inc, Austin, Tex.) according to the manufacturer's instructions. Presence of contaminating genomic DNA was assessed by a PCR assay on an aliquot of the RNA with zc41011 (SEQ ID NO: 11) and zc41012 (SEQ ID NO: 12), primers that amplify a single site of intergenic genomic DNA. The PCR conditions for the contaminating genomic DNA assay were as follows: 2.5 ul 10× buffer and 0.5 µl ADVANTAGE 2 cDNA polymerase mix (BD Biosciences Clontech, Palo Alto, Calif.), 2 µl 2.5 mM dNTP mix (Applied Biosystems, Foster City, Calif.), 2.5 µl 10× Rediload (Invitrogen, Carlsbad, Calif.), and 0.5 µl 20 uM zc41011 (SEQ ID NO: 11) and zc41012 (SEQ ID NO: 12), in a final volume of 25 µl. Cycling parameters were 94° C. 2', 40 cycles of 94° C. 15" 67° C. 50" and one cycle of 72° C. 5'. 10 µl of each reaction was subjected to agarose gel electrophoresis and gels were examined for presence of a PCR product from contaminating genomic DNA. If contaminating genomic DNA was observed, the total RNA was DNAsed using DNA-free reagents (Ambion, Inc, Austin, Tex.) according to the manufacturer's instructions, then retested as described above. Only RNAs which appeared to be free of contaminating genomic DNA were used for subsequent creation of first strand cDNA.

Example 4

1st Strand cDNA Production

10 µg total RNA from human cell lines were each brought to 47 µl with H$_2$O in duplicate, to create a plus Reverse Transcriptase (RT) sample and a corresponding negative control minus RT sample for each cell line. Reagents for first strand cDNA synthesis were added (Invitrogen First Strand cDNA Synthesis System, Carlsbad, Calif.): 20 µl 25 mM MgCl2, 10 µl 10× RT buffer, 10 µl 0.1 M DTT, 5 µl 10 mM dNTP mix, 2 ul Random hexamers (for CaCo2 cells), 2 µl oligo dT, 2 µl RNAseOut. Then, to one aliquot from each cell line 2 µl Superscript II Reverse Transcriptase was added, and to the corresponding cell line aliquot 2 µl H₂O was added to make a minus RT negative control. All samples were incubated as follows: 25° C. 10', 42° C. 50', 70° C. 15'. Quality of the first strand cDNA for each sample was assessed by a multiplex PCR assay using 1 µl of sample and primers to two widely expressed, but only moderately abundant genes, CLTC (clathrin) and TFRC (transferrin receptor C). 1.0 µl (20 pmol/µl) each of Clathrin primers zc42901 (SEQ ID NO: 13), zc42902 (SEQ ID NO: 14), and TFRC primers zc42599 (SEQ ID NO: 15), zc42600 (SEQ ID NO: 16), were mixed with 2.5 µl 10× buffer and 0.5 µl ADVANTAGE 2 cDNA polymerase mix (BD Biosciences Clontech, Palo Alto, Calif.), 2 µl 2.5 mM dNTP mix (Applied Biosystems, Foster City, Calif.), 2.5 µl 10× Rediload (Invitrogen, Carlsbad, Calif.), and added to 1st strand sample. Cycling parameters were as follows: 94° C. 2.0", 35 cycles of 94° C. 30", 61° C. 30", 72° C.30", and one cycle of 72° C. 5'. 10 ul of each reaction was subjected to agarose gel electrophoresis and gels were scored for the presence of a robust PCR product for each gene specific to the +RT sample for each cell line. First strand cDNAs passing the quality assesment were then diluted 1:5 in TE, 5 µl of which are representative of first strand CDNA resulting from 100 ng starting total RNA.

Example 5

A. 1st Strand PCR Experiment for p35

A set of 1st strand cDNAs from resting and stimulated human cell lines was screened for p35 expression using PCR. The samples were generated in-house as described in example 2 and contained first strand cDNA samples from 12 resting and stimulated human cell lines, along with their respective minus reverse transcriptase negative controls. The panel was set up in a 96-well format that included 1 positive control sample, human genomic DNA (BD Bioscience Clontech, Palo Alto, Calif.). A dilution series of the samples was created. Each well contained either 5 µl of cDNA and 10.5 µl of water, 1 µl of cDNA and 14.5 µl of water or 1 µl of a 1:5 dilution of cDNA and 14.5 µl water. Expression of the DNA in the resting and stimulated human cell lines samples for p35 was assayed by PCR with sense oligo zc16909 (SEQ ID NO: 15) and antisense oligo zc45224 (SEQ ID NO: 16) under these PCR conditions per sample: 2.5 µl 10× buffer and 0.5 µl ADVANTAGE 2 cDNA polymerase mix (BD Biosciences Clontech, Palo Alto, Calif.), 2 µl 2.5 mM dNTP mix (Applied Biosystems, Foster City, Calif.), 2.5 µl 10× Rediload (Invitrogen, Carlsbad, Calif.), and 1.0 µl 20 µM each sense and antisense primer. Cycling conditions were 94° C. for 2 minutes, 35 cycles of 94° C. for 30 seconds, 62.0° C. for 30 seconds, 72° C. for 1 minute and one cycle of 72° C. for 5 minutes. 10 µl of each reaction was subjected to agarose gel electrophoresis and gels were scored for positive or negative expression of p35. The expected PCR products with these oligonucleotides are 280 bp from cDNA and 1272 bp from genomic DNA. See tables 1 and 2 below listing the cell line samples that were assayed for p35 mRNA and the results.

TABLE 1

| cDNA's | | P35 |
|---|---|---|
| CaCo2 stimulated with IL1a | +RT | YES |
| CaCo2 stimulated with TNFa | +RT | YES |
| CaCo2 stimulated with INFg | +RT | YES |

TABLE 1-continued

| cDNA's | | P35 |
|---|---|---|
| CaCo2 stimulated with IL1a and IFNg | +RT | YES |
| CaCo2 stimulated with TNFa and INFg | +RT | YES |
| CaCo2 | +RT | YES |
| HT-29 stimulated with IL1a | +RT | NO |
| HT-29 stimulated with TNFa | +RT | YES |
| HT-29 stimulated with INFg | +RT | YES |
| HT-29 stimulated with IL1a and IFNg | +RT | YES |
| HT-29 stimulated with TNFa and INFg | +RT | YES |
| HT-29 | +RT | NO |
| CaCo2 stimulated with IL1a | −RT | NO |
| CaCo2 stimulated with TNFa | −RT | NO |
| CaCo2 stimulated with INFg | −RT | NO |
| CaCo2 stimulated with IL1a and IFNg | −RT | NO |
| CaCo2 stimulated with TNFa and INFg | −RT | NO |
| CaCo2 | −RT | NO |
| HT-29 stimulated with IL1a | −RT | NO |
| HT-29 stimulated with TNFa | −RT | NO |
| HT-29 stimulated with INFg | −RT | NO |
| HT-29 stimulated with IL1a and IFNg | −RT | NO |
| HT-29 stimulated with TNFa and INFg | −RT | NO |
| HT-29 | −RT | NO |

TABLE 2

| cDNA's | | P35 |
|---|---|---|
| SKLU-1 | +RT | YES |
| SKLU-1 stimulated with TNF | +RT | YES |
| SKLU-1 stimulated with LPS | +RT | YES |
| SKLU-1 stimulated with IFNg | +RT | YES |
| SKLU-1 stimulated with IL-4 | +RT | YES |
| SKLU-1 stimulated with IL-13 | +RT | YES |
| SKLU-1 stimulated with IL-17A | +RT | YES |
| SKLU-1 stimulated with IL-1b | +RT | YES |
| SKLU-1 | −RT | NO |
| SKLU-1 stimulated with TNF | −RT | NO |
| SKLU-1 stimulated with LPS | −RT | NO |
| SKLU-1 stimulated with IFNg | −RT | NO |
| SKLU-1 stimulated with IL-4 | −RT | NO |
| SKLU-1 stimulated with IL-13 | −RT | NO |
| SKLU-1 stimulated with IL-17A | −RT | NO |
| SKLU-1 stimulated with IL-1b | −RT | NO |

B. 1st Strand PCR Experiment for p40

A set of 1st strand cDNAs from resting and stimulated human cell lines was screened for p40 expression using PCR. The samples were generated as described in example 3A and contained first strand cDNA samples from 12 resting and stimulated human cell lines, along with their respective minus reverse transcriptase negative controls. The panel was set up in a 96-well format that included one positive control sample, human genomic DNA (BD Bioscience Clontech, Palo Alto, Calif.). A dilution series of the samples was created. Each well contained either 5 µl of cDNA and 10.5 µl of water, 1 µl of cDNA and 14.5 µl of water or 1 µl of a 1:5 dilution of cDNA and 14.5 µl water. Expression of the DNA in the resting and stimulated human cell lines samples for p40 was assayed by PCR with sense oligo zc49543 (SEQ ID NO: 17) and antisense oligo zc49544 (SEQ ID NO: 18) under these PCR conditions per sample: 2.5 µl 10× buffer and 0.5 µl ADVANTAGE 2™ cDNA polymerase mix (BD Biosciences Clontech, Palo Alto, Calif.), 2 µl 2.5 mM dNTP mix (Applied Biosystems, Foster City, Calif.), 2.5 ul 10× Rediload (Invitrogen, Carlsbad, Calif.), and 1.0 µl 20 µM each sense and antisense primer. Cycling conditions were 94° C. for 2 minutes, 35 cycles of 94° C. for 30 seconds, 70° C. for 30 seconds, 72° C. for 45 seconds and one cycle of 72° C. for 5 minutes. 10 µl of each reaction was subjected to agarose gel electrophoresis and gels were scored for positive or negative expression of p40. The expected PCR products with these oligonucleotides are 180 bp from cDNA and 723 bp from genomic DNA. See tables 3 and 4 below listing the cell line samples that were assayed for p40 mRNA and the results.

TABLE 3

| cDNA's | | P40 |
|---|---|---|
| CaCo2 stimulated with IL1a | +RT | NO |
| CaCo2 stimulated with TNFa | +RT | NO |
| CaCo2 stimulated with INFg | +RT | NO |
| CaCo2 stimulated with IL1a and IFNg | +RT | NO |
| CaCo2 stimulated with TNFa and INFg | +RT | NO |
| CaCo2 | +RT | NO |
| HT-29 stimulated with IL1a | +RT | NO |
| HT-29 stimulated with TNFa | +RT | NO |
| HT-29 stimulated with INFg | +RT | NO |
| HT-29 stimulated with IL1a and IFNg | +RT | NO |
| HT-29 stimulated with TNFa and INFg | +RT | NO |
| HT-29 | +RT | NO |
| CaCo2 stimulated with IL1a | −RT | NO |
| CaCo2 stimulated with TNFa | −RT | NO |
| CaCo2 stimulated with INFg | −RT | NO |
| CaCo2 stimulated with IL1a and IFNg | −RT | NO |
| CaCo2 stimulated with TNFa and INFg | −RT | NO |
| CaCo2 | −RT | NO |
| HT-29 stimulated with IL1a | −RT | NO |
| HT-29 stimulated with TNFa | −RT | NO |
| HT-29 stimulated with INFg | −RT | NO |
| HT-29 stimulated with IL1a and IFNg | −RT | NO |
| HT-29 stimulated with TNFa and INFg | −RT | NO |
| HT-29 | −RT | NO |

TABLE 4

| cDNA's | | P40 |
|---|---|---|
| SKLU-1 | +RT | NO |
| SKLU-1 stimulated with TNF | +RT | NO |
| SKLU-1 stimulated with LPS | +RT | NO |
| SKLU-1 stimulated with IFNg | +RT | NO |
| SKLU-1 stimulated with IL-4 | +RT | NO |
| SKLU-1 stimulated with IL-13 | +RT | NO |
| SKLU-1 stimulated with IL-17A | +RT | NO |
| SKLU-1 stimulated with IL-1b | +RT | NO |
| SKLU-1 | −RT | NO |
| SKLU-1 stimulated with TNF | −RT | NO |
| SKLU-1 stimulated with LPS | −RT | NO |
| SKLU-1 stimulated with IFNg | −RT | NO |
| SKLU-1 stimulated with IL-4 | −RT | NO |
| SKLU-1 stimulated with IL-13 | −RT | NO |
| SKLU-1 stimulated with IL-17A | −RT | NO |
| SKLU-1 stimulated with IL-1b | −RT | NO |

C. 1st Strand PCR Experiment for p19

A set of 1st strand cDNAs from resting and stimulated human cell lines was screened for p19 expression using PCR. The samples were generated in-house as described in example 3A and contained first strand cDNA samples from 12 resting and stimulated human cell lines, along with their respective minus reverse transcriptase negative controls. The panel was set up in a 96-well format that included one positive control sample, human genomic DNA (BD Bioscience Clontech, Palo Alto, Calif.). A dilution series of the samples was created. Each well contained either 5 µl of cDNA and 10.5 µl of water, 1 µl of cDNA and 14.5 µl of water or 1 µl of a 1:5 dilution of cDNA and 14.5 µl water. Expression of the DNA in the resting and stimulated human cell lines samples for p19 was assayed by PCR with sense oligo zc49302 (SEQ ID NO: 19) and antisense oligo zc49303 (SEQ ID NO: 20) under these PCR conditions per sample: 2.5 µl 10× buffer and 0.5 µl ADVANTAGE 2™ cDNA polymerase mix (BD Biosciences Clontech, Palo Alto, Calif.), 2 µl 2.5 mM dNTP mix (Applied Biosystems, Foster City, Calif.), 2.5 µl 10× Rediload (Invitrogen, Carlsbad, Calif.), and 1.0 µl 20 µM each sense and antisense primer. Cycling conditions were 94° C. for 2 minutes, 35 cycles of 94° C. for 30 seconds, 68° C. for 30 seconds, 72° C. for 30 seconds and one cycle of 72° C. for 5 minutes. 10 µl of each reaction was subjected to agarose gel electrophoresis and gels were scored for positive or negative expression of p19. The expected PCR products with these oligonucleotides are 344 bp from cDNA and 614 bp from genomic DNA. See tables 5 and 6 below listing the cell line samples that were assayed for p19 mRNA and the results.

TABLE 5

| cDNA's | | P19 |
|---|---|---|
| CaCo2 stimulated with IL1a | +RT | YES |
| CaCo2 stimulated with TNFa | +RT | YES |
| CaCo2 stimulated with INFg | +RT | YES |
| CaCo2 stimulated with IL1a and IFNg | +RT | YES |
| CaCo2 stimulated with TNFa and INFg | +RT | NO |
| CaCo2 | +RT | NO |
| HT-29 stimulated with IL1a | +RT | YES |
| HT-29 stimulated with TNFa | +RT | YES |
| HT-29 stimulated with INFg | +RT | NO |
| HT-29 stimulated with IL1a and IFNg | +RT | YES |
| HT-29 stimulated with TNFa and INFg | +RT | YES |
| HT-29 | +RT | YES |
| CaCo2 stimulated with IL1a | −RT | NO |
| CaCo2 stimulated with TNFa | −RT | NO |
| CaCo2 stimulated with INFg | −RT | NO |
| CaCo2 stimulated with IL1a and IFNg | −RT | NO |
| CaCo2 stimulated with TNFa and INFg | −RT | NO |
| CaCo2 | −RT | NO |
| HT-29 stimulated with IL1a | −RT | NO |
| HT-29 stimulated with TNFa | −RT | NO |
| HT-29 stimulated with INFg | −RT | NO |
| HT-29 stimulated with IL1a and IFNg | −RT | NO |
| HT-29 stimulated with TNFa and INFg | −RT | NO |
| HT-29 | −RT | NO |

TABLE 6

| cDNA's | | P19 |
|---|---|---|
| SKLU-1 | +RT | MAYBE |
| SKLU-1 stimulated with TNF | +RT | YES |
| SKLU-1 stimulated with LPS | +RT | YES |
| SKLU-1 stimulated with IFNg | +RT | YES |
| SKLU-1 stimulated with IL-4 | +RT | YES |
| SKLU-1 stimulated with IL-13 | +RT | YES |
| SKLU-1 stimulated with IL-17A | +RT | YES |
| SKLU-1 stimulated with IL-1b | +RT | YES |
| SKLU-1 | −RT | NO |
| SKLU-1 stimulated with TNF | −RT | NO |
| SKLU-1 stimulated with LPS | −RT | NO |
| SKLU-1 stimulated with IFNg | −RT | NO |
| SKLU-1 stimulated with IL-4 | −RT | NO |
| SKLU-1 stimulated with IL-13 | −RT | NO |
| SKLU-1 stimulated with IL-17A | −RT | NO |
| SKLU-1 stimulated with IL-1b | −RT | NO |

D. 1st Strand PCR Experiment for EBI-3

A set of 1st strand cDNAs from resting and stimulated human cell lines was screened for EBI-3 expression using PCR. The samples were generated in-house as described in example 3A and contained first strand cDNA samples from 12 resting and stimulated human cell lines, along with their respective minus reverse transcriptase negative controls. The panel was set up in a 96-well format that included one positive control sample, human placenta Marathon cDNA (BD Bioscience Clontech, Palo Alto, Calif.). A dilution series of the samples was created. Each well contained either 5 µl of cDNA and 10.5 µl of water, 1 µl of cDNA and 14.5 µl of water or 1 µl of a 1:5 dilution of cDNA and 14.5 µl water. Expression of the DNA in the resting and stimulated human cell lines samples for EBI-3 was assayed by PCR with sense oligo zc16908 (SEQ ID NO: 21) and antisense oligo zc44196 (SEQ ID NO: 22) under these PCR conditions per sample: 2.5 µl 10× buffer and 0.5 µl ADVANTAGE 2™ cDNA polymerase mix (BD Biosciences Clontech, Palo Alto, Calif.), 2 µl 2.5 mM dNTP mix (Applied Biosystems, Foster City, Calif.), 2.5 µl 10× Rediload (Invitrogen, Carlsbad, Calif.), and 1.0 µl 20 uM each sense and antisense primer. Cycling conditions were 94° C. for 2 minutes, 35 cycles of 94° C. for 30 seconds, 68° C. for 30 seconds, 72° C. for 30 seconds and one cycle of 72° C. for 5 minutes. 10 µl of each reaction was subjected to agarose gel electrophoresis and gels were scored for positive or negative expression of EBI-3. The expected PCR products with these oligonucleotides are 328 bp from cDNA. See tables 7 and 8 below listing the cell line samples that were assayed for EBI-3 mRNA and the results.

TABLE 7

| cDNA's | | EBI-3 |
|---|---|---|
| CaCo2 stimulated with IL1a | +RT | NO |
| CaCo2 stimulated with TNFa | +RT | NO |
| CaCo2 stimulated with INFg | +RT | NO |
| CaCo2 stimulated with IL1a and IFNg | +RT | YES |
| CaCo2 stimulated with TNFa and INFg | +RT | NO |
| CaCo2 | +RT | YES |
| HT-29 stimulated with IL1a | +RT | NO |
| HT-29 stimulated with TNFa | +RT | NO |
| HT-29 stimulated with INFg | +RT | NO |
| HT-29 stimulated with IL1a and IFNg | +RT | MAYBE |
| HT-29 stimulated with TNFa and INFg | +RT | YES |
| HT-29 | +RT | YES |
| CaCo2 stimulated with IL1a | −RT | NO |
| CaCo2 stimulated with TNFa | −RT | NO |
| CaCo2 stimulated with INFg | −RT | NO |
| CaCo2 stimulated with IL1a and IFNg | −RT | NO |
| CaCo2 stimulated with TNFa and INFg | −RT | NO |
| CaCo2 | −RT | NO |
| HT-29 stimulated with IL1a | −RT | NO |
| HT-29 stimulated with TNFa | −RT | NO |
| HT-29 stimulated with INFg | −RT | NO |
| HT-29 stimulated with IL1a and IFNg | −RT | NO |
| HT-29 stimulated with TNFa and INFg | −RT | NO |
| HT-29 | −RT | NO |

TABLE 8

| cDNA's | | EBI-3 |
|---|---|---|
| SKLU-1 | +RT | NO |
| SKLU-1 stimulated with TNF | +RT | YES |
| SKLU-1 stimulated with LPS | +RT | YES |
| SKLU-1 stimulated with IFNg | +RT | YES |
| SKLU-1 stimulated with IL-4 | +RT | NO |
| SKLU-1 stimulated with IL-13 | +RT | YES |
| SKLU-1 stimulated with IL-17A | +RT | YES |
| SKLU-1 stimulated with IL-1b | +RT | YES |
| SKLU-1 | −RT | NO |
| SKLU-1 stimulated with TNF | −RT | NO |
| SKLU-1 stimulated with LPS | −RT | NO |
| SKLU-1 stimulated with IFNg | −RT | NO |
| SKLU-1 stimulated with IL-4 | −RT | NO |
| SKLU-1 stimulated with IL-13 | −RT | NO |
| SKLU-1 stimulated with IL-17A | −RT | NO |
| SKLU-1 stimulated with IL-1b | −RT | NO |

E. 1st Strand PCR Experiment for Zsig81

A set of 1st strand cDNAs from resting and stimulated human cell lines was screened for zsig81 expression using PCR. The samples were generated in-house as described in example 3A and contained first strand cDNA samples from 12 resting and stimulated human cell lines, along with their respective minus reverse transcriptase negative controls. The panel was set up in a 96-well format that included 1 positive control sample, human colon 1st strand cDNA (BD Bioscience Clontech, Palo Alto, Calif.). A dilution series of the samples was created. Each well contained either 5 µl of cDNA and 10.5 µl of water, 1 µl of cDNA and 14.5 µl of water or 1 µl of a 1:5 dilution of cDNA and 14.5 µl water. Expression of the DNA in the resting and stimulated human cell lines samples for zsig81 was assayed by PCR with sense oligo zc50352 (SEQ ID NO: 23) and antisense oligo zc50354 (SEQ ID NO: 24) under these PCR conditions per sample: 2.5 µl 10× buffer and 0.5 µl ADVANTAGE 2™ cDNA polymerase mix (BD Biosciences Clontech, Palo Alto, Calif.), 2 µl 2.5 mM dNTP mix (Applied Biosystems, Foster City, Calif.), 2.5 µl 10× Rediload (Invitrogen, Carlsbad, Calif.), and 1.0 µl 20 µM each sense and antisense primer. Cycling conditions were 94° C. for 2 minutes, 35 cycles of 94° C. for 30 seconds, 68° C. for 30 seconds, 72° C. for 30 seconds and one cycle of 72° C. for 5 minutes. 10 µl of each reaction was subjected to agarose gel electrophoresis and gels were scored for positive or negative expression of zsig81. The expected PCR products with these oligonucleotides are 250 bp from cDNA. See tables 9 and 10 below listing the cell line samples that were assayed for zsig81 mRNA and the results.

TABLE 9

| cDNA's | | ZSIG81 |
|---|---|---|
| CaCo2 stimulated with IL1a | +RT | YES |
| CaCo2 stimulated with TNFa | +RT | YES |
| CaCo2 stimulated with INFg | +RT | YES |
| CaCo2 stimulated with IL1a and IFNg | +RT | YES |
| CaCo2 stimulated with TNFa and INFg | +RT | YES |
| CaCo2 | +RT | YES |
| HT-29 stimulated with IL1a | +RT | YES |
| HT-29 stimulated with TNFa | +RT | YES |
| HT-29 stimulated with INFg | +RT | YES |
| HT-29 stimulated with IL1a and IFNg | +RT | YES |
| HT-29 stimulated with TNFa and INFg | +RT | YES |
| HT-29 | +RT | YES |
| CaCo2 stimulated with IL1a | −RT | NO |
| CaCo2 stimulated with TNFa | −RT | NO |
| CaCo2 stimulated with INFg | −RT | NO |
| CaCo2 stimulated with IL1a and IFNg | −RT | NO |
| CaCo2 stimulated with TNFa and INFg | −RT | NO |
| CaCo2 | −RT | NO |
| HT-29 stimulated with IL1a | −RT | NO |
| HT-29 stimulated with TNFa | −RT | NO |
| HT-29 stimulated with INFg | −RT | NO |
| HT-29 stimulated with IL1a and IFNg | −RT | NO |
| HT-29 stimulated with TNFa and INFg | −RT | NO |
| HT-29 | −RT | NO |

TABLE 10

| cDNA's | | Zsig81 |
|---|---|---|
| SKLU-1 | +RT | YES |
| SKLU-1 stimulated with TNF | +RT | YES |
| SKLU-1 stimulated with LPS | +RT | YES |
| SKLU-1 stimulated with IFNg | +RT | YES |
| SKLU-1 stimulated with IL-4 | +RT | YES |
| SKLU-1 stimulated with IL-13 | +RT | YES |
| SKLU-1 stimulated with IL-17A | +RT | YES |
| SKLU-1 stimulated with IL-1b | +RT | YES |
| SKLU-1 | −RT | NO |
| SKLU-1 stimulated with TNF | −RT | NO |
| SKLU-1 stimulated with LPS | −RT | NO |
| SKLU-1 stimulated with IFNg | −RT | NO |
| SKLU-1 stimulated with IL-4 | −RT | NO |

TABLE 10-continued

| cDNA's | | Zsig81 |
|---|---|---|
| SKLU-1 stimulated with IL-13 | –RT | NO |
| SKLU-1 stimulated with IL-17A | –RT | NO |
| SKLU-1 stimulated with IL-1b | –RT | NO |

Example 6

Zsig81 Knockout Mice

A. Generation of Knockout (KO) Construct for Murine zsig81.

To further study biological function of zsig81 in vivo, a mouse Knockout (KO) strain is created to ablate zsig81 expression. First, mouse zsig81 cDNA probes are used to screen a mouse 129/SvJ genomic BAC library. Clones containing zsig81 genomic locus are identified and characterized.

To create a knockout construct for ablation of zsig81, a knockout vector is made by using ET cloning technique (Zhang et al. Nat. Genet. 20:123-8, 1998). Briefly, the KO vector contains a 1.5 kb 5' arm (short arm), an IRES-LacZ/MC1neo selectable marker, and a 9.0 Kb 3' arm (long arm) of zsig81 gene. In the KO vector, majority of exons 2 and 3, as well as intron 2 of zsig81 genomic sequence are replaced by the IRES-LacZ/MC1neo selectable marker so that a deletion of about 2.0 Kb is generated by homologous recombination in ES cells.

After linearization of the KO vector by restriction enzyme PmeI, it is electroporated into 129/SvJ ES cells. Selection of homologous recombination events, as well as identification of recombinant ES clones are performed as described in Robertson, E. J. et al. *Teratocarcinomas and Embryonic Stem Cells: A Practical Approach,* 2nd ed., IRL Press Limited, Oxford, 1987.

B. Creation and Analysis of Mice with Ablated zsig81 Expression.

Positive ES clones, in which deletion of Exons 2-3 and Introns 2 of zsig81 genomic locus occurs, are expanded. They are injected into balstocysts of C57B1/6j mice. After brief re-expansion of the injected blastocysts, they are introduced into pseudo-pregnant foster mothers to generate chimeras. Blastocyst injection, chimera breeding and subsequent germline transmission of mutated zsig81 are performed as described in Robertson, E. J. et al. ibid., 1987.

The KO mutant mice are identified by PCR genotyping strategy. Three PCR primers, zc28200 (SEQ ID NO: 25), zc28757 (SEQ ID NO: 26), and zc38398 (SEQ ID NO: 27) are used in a multiplex PCR reaction to detect wild-type allele and mutant allele. The wild type allele yields a DNA fragment of 143 bp in length, while the KO allele generates a DNA fragment of 223 bp in length.

The pairing of hemizygote mice produce a normal ratio of homozygote (HOM), heterozygote (Het), and wild type (wt) offspring, as well as a normal sex ratio. Inspecting the mice includes collecting body weight, tissue weight, complete blood count (CBC), clinical chemistry, gross observation, and HistoPathology) and reveals no significant differences between HOM, Het, and wildtype animals.

Example 7

Zsig81 Knockout Mouse Asthma Model

To determine the possible role that zsig81 may play in the development of antigen-induced airway hyper-responsiveness, zsig81 KO mice in a murine model of OVA-induced asthma were tested. Briefly, zsig81 KO and wildtype mice were sensitized to OVa proten via intraperitoneal injection of OVa. in alum adjuvant (10 µg/50% alum) on day 0 and day 7. One week later, mice were challenged intranasally on two consecutive days (day 14 and 15) with OVa protein. Forty-eight hours after the last challenge, serum, bronchoalvolar lavage (BAL) fluid and lung tissue were collected for analysis. In addition, a small cohort of mice were tested for antigen-induced airway hyper-responsiveness via the plethysmograph. These studies have been done twice Results:

(i) Serum. In both studies there was no significant difference in the levels of total IgE or OVA-specific IgE between zsig81 KO and wildtype mice.

(ii) BAL cellular infiltrate. In both studies, there was no significant difference between zsig81 KO or wildtype in the percent of infiltrating cells in the lung or the types of infiltrating cells (ie. lymphocytes, neutrophils, macrophages and eosinophils).

(iii) BAL fluid cytokines. Analysis of BAL fluid cytokines have been completed for only one of the two studies. The data suggest that BAL fluid from zsig81 KO mice had significantly lower levels of IL-5, IL-13 and TNFa compared to wildtype mice and significantly higher levels of IFNg.

(iv) Lung Pathology. Pathology analysis of lungs from wildtype and zsig81 KO mice suggested no obvious differences between groups in the severity or distribution of changes associated with inflammation in these mice. These data need to be repeated.

(iv) Airway hyper-responsiveness as measured by plethysmography. In both studies the zsigKO mice demonstrated significantly increased susceptibility to antigen-induced airway hyper-responsiveness compared to wildtype mice ($p<0.001$).

The analysis of AHR by plethysmography shows that the zsig81 KO mice are more susceptible to antigen-induced hyper-responsiveness even though no increase in antigen-specific IgE levels or cellular infiltrates in the lung were seen. These data suggest that zsig81 KO mice may have structural issues in the lung that promote susceptibility to asthma.

Example 8

A. 1st Strand PCR Experiment for p35

A set of 1st strand cDNAs from resting and stimulated human cell lines was screened for p35 expression using PCR. The samples were generated in-house as described in example 2 and contained first strand cDNA samples from 4 resting and stimulated human cell lines, along with their respective minus reverse transcriptase negative controls. The panel was set up in a 24-well format that included 1 positive control sample, human genomic DNA (BD Bioscience Clontech, Palo Alto, Calif.). Each well contained 1 µl of cDNA and 14.5 µl of water. Expression of the DNA in the resting and stimulated human cell lines samples for p35 was assayed by PCR with sense oligo zc16909 (SEQ ID NO: 15) and anti-sense oligo zc45224 (SEQ ID NO: 16) under these PCR conditions per sample: 2.5 ul 10× buffer and 0.5 ul ADVANTAGE 2 cDNA polymerase mix (BD Biosciences Clontech, Palo Alto, Calif.), 2 µl 2.5 mM dNTP mix (TAKARA bio Inc., Shiga, Japan), 2.5 μl 10× Rediload (Invitrogen, Carlsbad, Calif.), and 1.0 μl 20 uM each sense and antisense primer. Cycling conditions were 94° C. for 2 minutes, 35 cycles of 94° C. for 30 seconds, 62° C. for 30 seconds, 72° C. for 1 minute and one cycle of 72° C. for 5 minutes. 10 ul of each reaction was subjected to agarose gel electrophoresis and gels were scored for positive or negative expression of p35. The expected PCR products with these oligonucleotides are 280 bp from cDNA and 1272 bp from genomic DNA. See table 11 below listing the cell line samples that were assayed for p35 mRNA and the results.

TABLE 11

| cDNA's | | P35 |
|---|---|---|
| NHBE | −RT | NO |
| NHBE stimulated with IFNg | −RT | NO |
| NHBE stimulated with TNFa | −RT | NO |
| NHBE stimulated with IFNg and TNFa | −RT | NO |
| NHBE | +RT | YES |
| NHBE stimulated with IFNg | +RT | YES |
| NHBE stimulated with TNFa | +RT | YES |
| NHBE stimulated with IFNg and TNFa | +RT | YES |

B. 1st Strand PCR Experiment for p40

A set of 1st strand cDNAs from resting and stimulated human cell lines was screened for p40 expression using PCR. The samples were generated in-house as described in example 2 and contained first strand cDNA samples from 4 resting and stimulated human cell lines, along with their respective minus reverse transcriptase negative controls. The panel was set up in a 24-well format that included 1 positive control sample, human genomic DNA (BD Bioscience Clontech, Palo Alto, Calif.). Each well contained 1 μl of cDNA and 14.5 μl of water. Expression of the DNA in the resting and stimulated human cell lines samples for p40 was assayed by PCR with sense oligo zc49543(SEQ ID NO: 17) and antisense oligo zc49544 (SEQ ID NO: 18) under these PCR conditions per sample: 2.5 μl 10× buffer and 0.5 μl ADVANTAGE 2 cDNA polymerase mix (BD Biosciences Clontech, Palo Alto, Calif.), 2 μl 2.5 mM dNTP mix (TAKARA bio Inc., Shiga, Japan), 2.5 μl 10× Rediload (Invitrogen, Carlsbad, Calif.), and 1.0 μl 20 μM each sense and antisense primer. Cycling conditions were 94° C. for 2 minutes, 35 cycles of 94° C. for 30 seconds, 62° C. for 30 seconds, 72° C. for 1 minute and one cycle of 72° C. for 5 minutes. 10 μl of each reaction was subjected to agarose gel electrophoresis and gels were scored for positive or negative expression of p40. The expected PCR products with these oligonucleotides are 180 bp from cDNA and 723 bp from genomic DNA. See table 12 below listing the cell line samples that were assayed for p40 mRNA and the results.

TABLE 12

| cDNA's | | P40 |
|---|---|---|
| NHBE | −RT | NO |
| NHBE stimulated with IFNg | −RT | NO |
| NHBE stimulated with TNFa | −RT | NO |

TABLE 12-continued

| cDNA's | | P40 |
|---|---|---|
| NHBE stimulated with IFNg and TNFa | −RT | NO |
| NHBE | +RT | NO |
| NHBE stimulated with IFNg | +RT | NO |
| NHBE stimulated with TNFa | +RT | NO |
| NHBE stimulated with IFNg and TNFa | +RT | NO |

C. 1st Strand PCR Experiment for p19

A set of 1st strand cDNAs from resting and stimulated human cell lines was screened for p19 expression using PCR. The samples were generated in-house as described in example 2 and contained first strand cDNA samples from 4 resting and stimulated human cell lines, along with their respective minus reverse transcriptase negative controls. The panel was set up in a 24-well format that included 1 positive control sample, human genomic DNA (BD Bioscience Clontech, Palo Alto, Calif.). Each well contained 1 μl of cDNA and 14.5 μl of water. Expression of the DNA in the resting and stimulated human cell lines samples for p19 was assayed by PCR with sense oligo zc49302(SEQ ID NO: 19) and antisense oligo zc49303 (SEQ ID NO: 20) under these PCR conditions per sample: 2.5 μl 10× buffer and 0.5 μl ADVANTAGE 2 cDNA polymerase mix (BD Biosciences Clontech, Palo Alto, Calif.), 2 μl 2.5 mM dNTP mix (TAKARA bio Inc., Shiga, Japan), 2.5 μl 10× Rediload (Invitrogen, Carlsbad, Calif.), and 1.0 μl 20 μM each sense and antisense primer. Cycling conditions were 94° C. for 2 minutes, 35 cycles of 94° C. for 30 seconds, 62.0° C. for 30 seconds, 72° C. for 1 minute and one cycle of 72° C. for 5 minutes. 10 μl of each reaction was subjected to agarose gel electrophoresis and gels were scored for positive or negative expression of p19. The expected PCR products with these oligonucleotides are 344 bp from cDNA and 614 bp from genomic DNA. See table 13 below listing the cell line samples that were assayed for p 19 mRNA and the results.

TABLE 13

| cDNA's | | P19 |
|---|---|---|
| NHBE | −RT | NO |
| NHBE stimulated with IFNg | −RT | NO |
| NHBE stimulated with TNFa | −RT | NO |
| NHBE stimulated with IFNg and TNFa | −RT | NO |
| NHBE | +RT | YES |
| NHBE stimulated with IFNg | +RT | YES |
| NHBE stimulated with TNFa | +RT | YES |
| NHBE stimulated with IFNg and TNFa | +RT | YES |

D. 1st Strand PCR Experiment for EBI-3

A set of 1st strand cDNAs from resting and stimulated human cell lines was screened for EBI-3 expression using PCR. The samples were generated in-house as described in example 2 and contained first strand cDNA samples from 4 resting and stimulated human cell lines, along with their respective minus reverse transcriptase negative controls. The panel was set up in a 24-well format that included 1 positive control sample, human placenta cDNA (in-house). Each well contained 1 µl of cDNA and 14.5 µl of water. Expression of the DNA in the resting and stimulated human cell lines samples for EBI-3 was assayed by PCR with sense oligo zc16908 (SEQ ID NO: 21) and antisense oligo zc44196 (SEQ ID NO: 22) under these PCR conditions per sample: 2.5 pl lOX buffer and 0.5 µl ADVANTAGE 2 cDNA polymerase mix (BD Biosciences Clontech, Palo Alto, Calif.), 2 µl 2.5 mM dNTP mix (TAKARA bio Inc., Shiga, Japan), 2.5 µl 10× Rediload (Invitrogen, Carlsbad, Calif.), and 1.0 µl 20 µM each sense and antisense primer. Cycling conditions were 94° C. for 2 minutes, 35 cycles of 94° C. for 30 seconds, 62.0° C. for 30 seconds, 72° C. for 1 minute and one cycle of 72° C. for 5 minutes. 10 µl of each reaction was subjected to agarose gel electrophoresis and gels were scored for positive or negative expression of EBI-3. The expected PCR products with these oligonucleotides are 328 bp from cDNA. See table 14 below listing the cell line samples that were assayed for EBI-3 mRNA and the results.

TABLE 14

| cDNA's | | EBI-3 |
|---|---|---|
| NHBE | −RT | NO |
| NHBE stimulated with IFNg | −RT | NO |
| NHBE stimulated with TNFa | −RT | NO |
| NHBE stimulated with IFNg and TNFa | −RT | NO |
| NHBE | +RT | NO |
| NHBE stimulated with IFNg | +RT | NO |
| NHBE stimulated with TNFa | +RT | YES |
| NHBE stimulated with IFNg and TNFa | +RT | YES |

E. 1st Strand PCR Experiment for Zsig81

A set of 1st strand cDNAs from resting and stimulated human cell lines was screened for zsig81 expression using PCR. The samples were generated in-house as described in example 2 and contained first strand cDNA samples from 4 resting and stimulated human cell lines, along with their respective minus reverse transcriptase negative controls. The panel was set up in a 24-well format that included one positive control sample, human colon 1st strand cDNA (in-house). Each well contained 1 µl of cDNA and 14.5 µl of water. Expression of the DNA in the resting and stimulated human cell lines samples for zsig81 was assayed by PCR with sense oligo zc50352 (SEQ ID NO: 23) and antisense oligo zc50354 (SEQ ID NO: 24) under these PCR conditions per sample: 22.5 µl 10× buffer and 0.5 µl ADVANTAGE 2 cDNA polymerase mix (BD Biosciences Clontech, Palo Alto, Calif.), 2 µl 2.5 mM dNTP mix (TAKARA bio Inc., Shiga, Japan), 2.5 µl 10× Rediload (Invitrogen, Carlsbad, Calif.), and 1.0 µl 20 µM each sense and antisense primer. Cycling conditions were 94° C. for 2 minutes, 35 cycles of 94° C. for 30 seconds, 62.0° C. for 30 seconds, 72° C. for 1 minute and one cycle of 72° C. for 5 minutes. 10 µl of each reaction was subjected to agarose gel electrophoresis and gels were scored for positive or negative expression of zsig81. The expected PCR products with these oligonucleotides are 250 bp from cDNA. See table 15 below listing the cell line samples that were assayed for zsig81 mRNA and the results.

TABLE 15

| cDNA's | | Zsig81 |
|---|---|---|
| NHBE | −RT | NO |
| NHBE stimulated with IFNg | −RT | NO |
| NHBE stimulated with TNFa | −RT | NO |
| NHBE stimulated with IFNg and TNFa | −RT | NO |
| NHBE | +RT | YES |
| NHBE stimulated with IFNg | +RT | YES |
| NHBE stimulated with TNFa | +RT | YES |
| NHBE stimulated with IFNg and TNFa | +RT | YES |

Example 9

A. Constructs for Generating zcyto33f2 Transgenic Mice

Oligonucleotides are designed to generate a PCR fragment containing a consensus Kozak sequence and the human zcyto33f2 coding region. These oligonucleotides are designed with an FseI site at the 5' end (zc50983; SEQ ID NO: 67) and an AscI site at the 3' end zc50984; SEQ ID NO: 68) to facilitate cloning into pKFO51, a lymphoid-specific transgenic vector.

PCR reactions are carried out with about 200 ng human zcyto33f2 template and above oligonucleotides designed to amplify the full-length portion of the zcyto33f2. A PCR reaction is performed using methods known in the art. The isolated, correct sized DNA fragment is digested with FseI and AscI (Boerhinger-Mannheim), ethanol precipitated and ligated into pKFO51 previously digested with FseI and AscI. The pKFO51 transgenic vector is derived from p 1026× (Iritani, B. M., et al., *EMBO J.* 16:7019-31, 1997) and contains the T cell-specific lck proximal promoter, the B/T cell-specific immunoglobulin µ heavy chain enhancer, a polylinker for the insertion of the desired clone, and a mutated hGH gene that encodes an inactive growth hormone protein (providing 3' introns and a polyadenylation signal).

About one microliter of each ligation reaction is electroporated, plated, clones picked and screened for the human zcyto33f2 insert by restriction digestion as described above. A correct clone of pKFO51-zcyto33f2 is verified by sequencing, and a maxiprep of this clone is performed. A NotI fragment, containing the lck proximal promoter and immunoglobulin µ enhancer (EµLCK), zcyto33f2 cDNA, and the mutated hGH gene is prepared to be used for microinjection into fertilized murine oocytes. Microinjection and production of transgenic mice are produced as described in Hogan, B. et al. *Manipulating the Mouse Embryo,* 2nd ed., Cold Spring Harbor Laboratory Press, NY, 1994.

B. Constructs for Generating zcyto35f2 Transgenic Mice

Oligonucleotides are designed to generate a PCR fragment containing a consensus Kozak sequence and the human zcyto35f2 coding region. These oligonucleotides are designed with an FseI site at the 5' end (zc52289; SEQ ID NO: 69) and an AscI site at the 3' end (zc52290; SEQ ID NO: 70) to facilitate cloning into pKFO51, a lymphoid-specific transgenic vector.

PCR reactions are carried out with about 200 ng human zcyto35f2 template and above oligonucleotides designed to amplify the full-length portion of the zcyto35f2. A PCR reaction is performed using methods known in the art. The isolated, correct sized DNA fragment is digested with FseI and AscI (Boerhinger-Mannheim), ethanol precipitated and ligated into pKFO51 previously digested with FseI and AscI. The pKFO51 transgenic vector is derived from µ 1026× (Iritani, B. M., et al., *EMBO J.* 16:7019-31, 1997) and contains the T cell-specific lck proximal promoter, the B/T cell-specific immunoglobulin µ heavy chain enhancer, a polylinker for the insertion of the desired clone, and a mutated hGH gene that encodes an inactive growth hormone protein (providing 3' introns and a polyadenylation signal).

About one microliter of each ligation reaction is electroporated, plated, clones picked and screened for the human zcyto35f2 insert by restriction digestion as described above. A correct clone of pKFO51-zcyto35f2 is verified by sequencing, and a maxiprep of this clone is performed. A NotI fragment, containing the lck proximal promoter and immunoglobulin µ enhancer (EµLCK), zcyto35f2 cDNA, and the mutated hGH gene is prepared to be used for microinjection into fertilized murine oocytes. Microinjection and production of transgenic mice are produced as described in Hogan, B. et al. *Manipulating the Mouse Embryo,* 2nd ed., Cold Spring Harbor Laboratory Press, NY, 1994.

C. Preparing Transgenic Animals

Splenocytes were collected from animals carrying a zcyto33f2 transgene. The ability of these cells to respond in vitro was measured by stimulating whole populations of splenocytes with T cell mitogenic antibodies (anti-CD3 and anti-CD28) or B cell mitogenic antibodies (anti-IgM). Proliferative responses were then measured by the incorporation of tritiated-thymidine. T cell responses in zcyto33f2 transgenic animals were generally normal. In comparison we observed diminished B cell proliferative responses in IgM stimulated splenocytes from zctyto33f2 transgenic animals. These responses were observed in multiple animals from two independently generated transgenic lines and there was a general correlation with transgene expression level (as measured by expression of transcript from a human growth hormone tag incorporated into the transgene vector). The presence of this phenotype in two independent lines and the correlation with expression level suggest that it is a direct consequence of transgene expression. Exposure to zcyto33f2 thus affects the ability of splenic B cells to productively respond to stimulation through the B-cell receptor. This could be due to a direct effect on B cell activation but could also reflect a developmental abnormality.

Transgenic animals carrying a zcyto35 transgene were generated by microinjection. Spleen biopsies were performed on four individual founder animals using standard survival surgery techniques, and immune development assessed by flow cytometric analysis of cell suspensions generated from these biopsies. Two of four founder animals analysed exhibited alterations in T cell development, with an increase in the percentage of CD4 positive T cells and a decrease in the percentage of CD8+ T cells. Amongst the CD4+ population there was increased expression of CD25, a marker of activated and T regulatory cells. The same two animals also exhibited alterations in B cell development, with an increase in immature B cells and a decrease in mature B cells. Both of these animals expressed the zcyto35 transgene, as measured by expression of transcript from a human growth hormone tag incorporated into the transgene vector. This suggests that zcyto35 is an immunologically active molecule.

Lymphoid organs from zcyto33f2 animals were also examined by flow cytometric analysis and immune development evaluated. Zcyto33f2 transgenic animals exhibited modest but intermittent alterations in T cell and B cell populations in spleen and bone marrow, with a trend towards elevated CD4+ T cells and towards decreased B cells and CD8+ T cells.

Transgenic Histology

Nine male and 10 female high expressing transgenic and 3 male and 4 female cohort wild-type mice ranging in age from 9 to 35 weeks were necropsied and their tissues submitted for histopathology. A full tissue screen (30 tissues) was conducted on 11 transgenic and 3 wild-type mice, and a limited screen (lung, small intestine, and large intestine) was done on 8 transgenic and 4 wild-type mice. The tissues were fixed in 10% neutral buffered formalin, routinely processed into paraffin blocks, sectioned at 5 µm, and stained with hematoxylin and eosin.

Peribronchiolar and perivascular mononuclear inflammatory cell infiltrates were observed in the lungs of 17 of 19 transgenic mice (89%) and in the lungs of 2 wild type mice (29%). Mononuclear infiltrates were also present in the lamina propria of the small intestine of 8 of 19 transgenic mice, in the lamina propria of the large intestine of 3 of 19 transgenics, and in the submucosa or mucosa of the stomach of 5 of 11 transgenics. Additional changes observed in the small intestine of the transgenic animals included crypt dilatation (8 animals; this change was also observed in 1 wild-type mouse) and epithelial hyperplasia (6 animals). Nearly all of the above changes were graded as minimal-to-mild severity. No significant changes beyond normal background findings were observed in other tissues examined.

Mild inflammation appears to be part of the zcyto33f2 phenotype. Mononuclear inflammatory cell infiltrates are common incidental findings in the tissues of mice. However, the incidence of mononuclear infiltrates was high in the lungs and intestinal tracts of the zcyto33f2 transgenics. Mononuclear infiltrates were either not observed in the lung and intestine of wild-type cohorts or were present in these animals at a low incidence. Crypt dilatation and epithelial hyperplasia in the intestine of the transgenic mice are most likely associated with the inflammatory changes observed in this tissue.

Example 10

Primary and Secondary Antigen-Specific Immune Responses in zcyto33f2 Transgenic Mice Zcyto33f2 transgenic and wildtype mice were immunized and challenged with TNP-KLH to determine if there were any differences in antigen-specific responses between mice. Mice from 4 different zcyto33f2 lines; 13370, 13391, 13323, 13334 and wildtype mice were immunized subcutaneously (sc) with 100 µg TNP-KLH in alum on day 0 and boosted IP with 100 µg TNP-KLH on day 22. Serum was collected via retroorbital bleed on days −3, 7, 21 and 29 relative to immunization. TNP-specific IgG1 and IgM responses and total serum IgG1 and IgM were measured by ELISA. At the end of the study animals were euthanized and spleens were collected for FACS and ex vivo stimulation.

TABLE 16

DESIGN

| Group | n | mice | Immunization | Bleeds | Boost | Assays |
|---|---|---|---|---|---|---|
| A | 23 | Zcyto33f2-SC 4 lines 16 × female, 7 × male | 100 ug TNP-KLH 4.5% alum sc in both | Day −3, 7, 21, 28 | 100 ug TNP-KLH ip Day 22 | Anti-TNP IgG1 and IgM Serum cytokines |

TABLE 16-continued

DESIGN

| Group | n | mice | Immunization | Bleeds | Boost | Assays |
|---|---|---|---|---|---|---|
| B | 14 | Non tg<br>7 × female,<br>7 × male | flanks | | | Spleens/BM |

TABLE 17

| Day | Weekday | Date | Procedure |
|---|---|---|---|
| −3 | F | Apr. 14, 2006 | Bleed mice for serum |
| 0 | M | Apr. 17, 2006 | Immunize mice sc with 100 ug TNP-KLH alum in both flanks |
| 7 | M | Apr. 24, 2006 | Bleed mice for serum |
| 21 | M | May 8, 2006 | Bleed mice for serum |
| 22 | Tu | May 9, 2006 | Boost 100 ug TNP-KLH ip |
| 29 | Tu | May 16, 2006 | Sac; splenectomize mice and collect blood via cardiac punch |

Antigen Preparation (1:1) for Immunization:

1. Make 1 mg/ml TNP-KLH (Biosearch Technology Inc., Novato, Calif.) in sterile PBS or saline
2. Vortex Imject (Pierce, Rockford, Ill.) to mix
3. Add antigen by drops with vortexing
4. Rock 30 minutes at room temperature
5. Inject 100 µl sc into both flanks (100 µg/mouse); use tuberculin syringe with 27 gauge needle
6. For Boost: inject 100 µg TNP-KLH in sterile PBS ip Spleens, serum and femurs are harvested when the animals are sacrificed.

Assays

1. Serum anti-TNP IgG1 and IgM levels tested on days −3, 7, 21, 29
2. Serum cytokines are measured.
3. Ex vivo splenocyte proliferation is measured: TNP-KLH (50, 25, 12.5, 6.25, 3.12, 1.56, 0 µg/ml)
4. Ex vivo cytokine production is measured.
5. Bone marrow expansion is measured and phenotyped Mice from transgenic line 13370 had increased antigen-specific and total IgM responses compared to wildtype mice. Their total IgG1 concentrations were slightly reduced. Mice from line 13391 had significantly increased antigen-specific and total IgM secondary responses (post IP boost) and increased antigen-specific and total IgG1 secondary responses (total IgG1 is significant). Mice from line 13323 had significantly less secondary ag-specific responses compared with wildtyp mice. There were no differences in immunoglobulin concentrations between wildtype and transgenic line 13334 mice.

Example 11

Mixed Lymphocyte Reaction (MLR)

Bone marrow was flushed from the femurs of Balb/C mice with PBS; 2% FBS, and passed through a cell strainer. Red blood cells were lysed and intact cells were isolated by centrifugation. Cells were plated at $1\times10^6$ cells/mL in 100 ng/mL Flt2L (R & D Systems, Minneapolis, Minn.), and cultured for seven days. On day 7 dendritic cells were harvested from the culture and treated for 18 hrs with 1 µg/mL mCD40L and 20 ng/mL murine interferonγ.

Splenocytes were isolated from zcyto33f2 transgenic animals (C57B6 background) and C57B6 wild type animals. Splenocytes were suspended in PBS at $1\times10^7$ cells/mL and labeled with CFSE (Molecular Probes, Eugene, Oreg.).

$1\times10^5$ CFSE-labeled splenocytes from transgenic or wild-type mice were mixed with $1\times10^4$ bone marrow derived dendritic cells from Balb/C mice and incubated for 4 days. The cells were then stained for cell surface expression of CD4 and CD8. Following staining, the cells were analyzed, by fluorescence activated cell sorting, for cell surface expression of CD4 or CD8 as well as for proliferation by cell count and by dilution of CFSE intensity.

Both CD4 and CD8 T-cells from zcyto33f2 transgenic animals showed a diminished proliferative response in an MLR assay when compared to T-cells from wild type animals. Taken together, these data along with expression data showing expression in epithelium of gut and lung, suggest that zcyto33f2 can act as a negative regulator of T-cell function to modulate the immune response in lung and gut epithelium.

The suggestion of effects on T-cell response is supported by the observation that zsig81 KO animals are more susceptible to lung hypersensitivity and to gut inflammation in the oxazalone model of IBD (T-cell dependent model).

Example 12

Colitis Induction Model

A study was done to determine if colitis could be induced using oxazolone in zcyto33f2 or zsig81KO mice. Both lines were on a C57BL/6 background that has been found to be resistant to experimentally induced colitis.

Day 0 Animals were lightly anesthetized, had their lower abdomen shaved, and painted with 200 µL 3% solution of oxazolone in 100% ethanol.

Day 6 Animals were fasted overnight to facilitate the rectal application of material.

Day 7 Animals were lightly anesthetized and 150 µL of 6% oxazolone emulsified in cornflower oil was applied rectally using 1.5" PE50 tubing on a 23 g needle.

Day 9 Stools from all animals were collected and assessed for blood and diarrhea like symptoms.

Day 11 Animals were killed and colons were inspected for signs of inflammation.

Groups:

1. zcyto33f2, n=3, (control, just rectal corn oil)
2. zcyto33f2, n=3, (rectal 6% oxazolone in corn oil)
3. zsig81KO, n=4, (control, just rectal corn oil)
4. zsig81KO, n=5, (rectal 6% oxazolone in corn oil)

Measurements: Body weights—Day 7-11; blood in stools and watery stools—Day 9, 11; colon appearance—at sacrifice on day 11; The data were analyzed using two-way repeated measures ANOVA with Bonferroni posttests.

The raw body weights are given in Table 18. Body weights were expressed relative to the starting weight for each animal and then averaged for each group. The oxazolone treated zcyto33f2 mice had significantly lower body weights than control mice on Days 9 and 10. The zsig81KO mice showed different profiles following the fast and treatment with oxazolone. The oxazolone treated animals gained little weight following the fast while the corn oil only controls regained most of their body weight. These differences were significant for each of the days following the fast. Blood was not found in any of the stools and there was no evidence of diarrhea. At autopsy, all of the colons appeared free from inflammation.

Oxazolone induced colitis has been shown to work in C57BL/6 mice. In the present study, differences in weight gain characteristic of this model were observed in the zsig81KO mice but not in the zcyto33f2 mice. None of the mice developed colitis as defined by blood in the stool or water stools. Colons at autopsy were not overtly inflamed and were similar in length between the groups.

TABLE 18

Body weights.

| ID | Gender | Type | Tx | BW d0 | BW d7 | BW d8 | BW d9 | BW d10 | BW d11 |
|---|---|---|---|---|---|---|---|---|---|
| 48107 | m | zcyto33f2 | ox | 24.1 | 19.7 | 22.1 | 23.3 | 22.9 | 24.4 |
| 48108 | m | zcyto33f2 | ox | 25.8 | 20.6 | 24.0 | 24.4 | 25.3 | 26.1 |
| 48575 | f | zcyto33f2 | ox | 21.1 | 17.0 | 19.9 | 20.1 | 19.4 | 21.5 |
| 47926 | m | zcyto33f2 | co | 28.7 | 22.4 | 26.7 | 27.6 | 29.0 | 29.4 |
| 58578 | m | zcyto33f2 | co | 25.4 | 20.3 | 23.8 | 25.4 | 26.2 | 26.5 |
| 58580 | m | zcyto33f2 | co | 24.4 | 19.3 | 23.9 | 25.1 | 25.1 | 25.8 |
| 53293 | f | zsig81KO | ox | 25.0 | 20.3 | 21.1 | 21.7 | 21.4 | 22.6 |
| 53294 | f | zsig81KO | ox | 29.6 | 22.8 | 24.2 | 22.9 | 22.3 | 23.8 |
| 53296 | m | zsig81KO | ox | 35.9 | 31.3 | 31.0 | 30.8 | 31.0 | 31.6 |
| 53297 | m | zsig81KO | ox | 33.8 | 29.8 | 29.2 | 28.4 | 26.5 | 27.0 |
| 53295 | f | zsig81KO | co | 26.4 | 20.3 | 23.2 | 24.2 | 24.2 | 24.5 |
| 53298 | m | zsig81KO | co | 31.8 | 27.6 | 30.6 | 31.3 | 30.6 | 30.5 |
| 53299 | m | zsig81KO | co | 38.6 | 34.6 | 36.3 | 35.8 | 35.1 | 34.8 |
| 53300 | m | zsig81KO | co | 28.2 | 23.5 | 26.3 | 27.8 | 27.7 | 27.8 |

What is claimed is:

1. A method of treating asthma comprising administering to a subject a therapeutically effective amount of a fusion protein selected from the group consisting of:
   (a) a first polypeptide comprising amino acid residues 1 to 156 of SEQ ID NO: 2 and a second polypeptide comprising amino acid residues of SEQ ID NO: 3 or SEQ ID NO: 4;
   (b) a first polypeptide comprising amino acid residues 6 to 156 of SEQ ID NO: 2 and a second polypeptide comprising amino acid residues of SEQ ID NO: 3 or SEQ ID NO: 4; and
   (c) a first polypeptide comprising amino acid residues 21 to 156 of SEQ ID NO: 2 and a second polypeptide comprising amino acid residues of SEQ ID NO: 3 or SEQ ID NO: 4.

2. A method of stimulating or expanding T regulatory cells in a subject with asthma comprising administering a therapeutically effective amount of a fusion protein selected from the group consisting of:
   (a) a first polypeptide comprising amino acid residues 1 to 156 of SEQ ID NO: 2 and a second polypeptide comprising amino acid residues of SEQ ID NO: 3 or SEQ ID NO: 4;
   (b) a first polypeptide comprising amino acid residues 6 to 156 of SEQ ID NO: 2 and a second polypeptide comprising amino acid residues of SEQ ID NO: 3 or SEQ ID NO: 4; and
   (c) a first polypeptide comprising amino acid residues 21 to 156 of SEQ ID NO: 2 and a second polypeptide comprising amino acid residues of SEQ ID NO: 3 or SEQ ID NO: 4.

* * * * *